(12) United States Patent
Varner et al.

(10) Patent No.: US 11,679,100 B2
(45) Date of Patent: Jun. 20, 2023

(54) METHODS OF ENHANCING IMMUNITY

(71) Applicant: The Regents of the University of California, Oakland, CA (US)

(72) Inventors: Judith Varner, La Jolla, CA (US); Michael C. Schmid, West Kirby (GB)

(73) Assignee: The Regents of the University of California, Oakland, CA (US)

( * ) Notice: Subject to any disclaimer, the term of this patent is extended or adjusted under 35 U.S.C. 154(b) by 98 days.

(21) Appl. No.: 17/058,605

(22) PCT Filed: May 30, 2019

(86) PCT No.: PCT/US2019/034525
§ 371 (c)(1),
(2) Date: Nov. 24, 2020

(87) PCT Pub. No.: WO2019/232132
PCT Pub. Date: Dec. 5, 2019

(65) Prior Publication Data
US 2021/0212997 A1     Jul. 15, 2021

Related U.S. Application Data

(60) Provisional application No. 62/678,134, filed on May 30, 2018.

(51) Int. Cl.
| | | |
|---|---|---|
| *A61K 31/427* | (2006.01) | |
| *A61P 35/00* | (2006.01) | |
| *A61K 31/7068* | (2006.01) | |
| *A61K 39/395* | (2006.01) | |
| *A61K 49/00* | (2006.01) | |
| *C12N 15/113* | (2010.01) | |
| *C12Q 1/6886* | (2018.01) | |

(52) U.S. Cl.
CPC ........ *A61K 31/427* (2013.01); *A61K 31/7068* (2013.01); *A61K 39/3955* (2013.01); *A61K 49/0008* (2013.01); *A61P 35/00* (2018.01); *C12N 15/1138* (2013.01); *C12Q 1/6886* (2013.01); *C12N 2310/141* (2013.01); *C12N 2320/31* (2013.01); *C12Q 2600/106* (2013.01); *C12Q 2600/158* (2013.01)

(58) Field of Classification Search
CPC .................................................... A61K 31/427
USPC ....................................................... 424/133.1
See application file for complete search history.

(56) References Cited

U.S. PATENT DOCUMENTS

| | | |
|---|---|---|
| 2009/0023226 A1 | 1/2009 | Arnaout et al. |
| 2010/0004320 A1 | 1/2010 | Elmen et al. |

FOREIGN PATENT DOCUMENTS

| | | |
|---|---|---|
| WO | WO-2008/073922 A2 | 6/2008 |
| WO | WO-2016/197974 A1 | 12/2016 |
| WO | WO-2017/127602 A1 | 7/2017 |

OTHER PUBLICATIONS

Maiguel et al (Science Signaling, 2011, 4(189)(ra57): 1-14).*
Trang et al (Oncogene, 2010, 29(11): 1580-1587).*
Meng et al. (JBC, 2007, 282(11): 8256-8264).*
Heo et al (PLOS One, 2015, 10(6)(e0129853): 1-18).*
Grigg et al. (Journal of Clinical Oncology, 2017, Abstract 9082).*
Soe et al. (American Journal of Gastroenterology, 2016, 111, p. S1262, Abstract 2474).*
Celik, et al., "Agonist Leukadherin-1 Increases CD11b/CD18-Dependent Adhesion via Membrane Tethers", Biophysical Journal, Dec. 3, 2013, vol. 105, pp. 2517-2527.
Ding, et al., "C-Myc functions as a competing endogenous RNA in acute promyelocytic leukemia" Oncotarget, Jul. 28, 2016, vol. 7, No. 35, pp. 56422-56430.
International Search Report and Written Opinion dated Aug. 30, 2019, from application No. PCT/US2019/034525.

* cited by examiner

*Primary Examiner* — Sean E Aeder
(74) *Attorney, Agent, or Firm* — Foley & Lardner LLP

(57) ABSTRACT

The present invention is based on the finding that CD11b signaling inhibits immune suppression, modulates neovascularization and promotes anti-tumor immune responses in models of murine and human cancer. As such, provided herein are methods of treating cancer using an antibody, protein or small molecule that modulates CD11b activity or expression. Also provided are methods of identifying cancer that is amenable to such treatment and/or increasing susceptibility of cancer cells to treatment with a chemotherapeutic agent.

9 Claims, 45 Drawing Sheets
Specification includes a Sequence Listing.

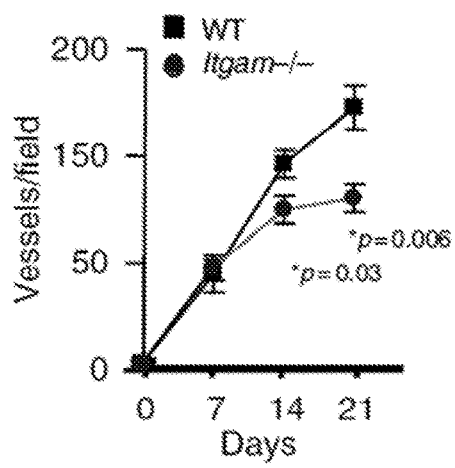
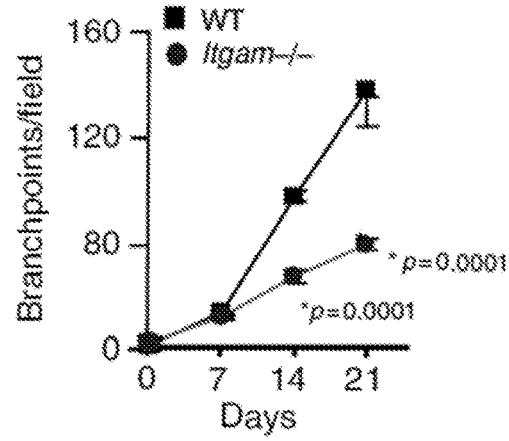
FIG. 2B
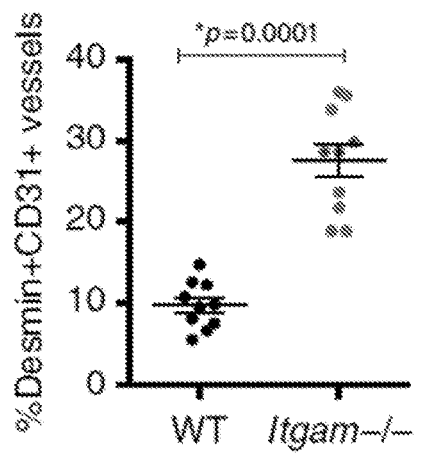
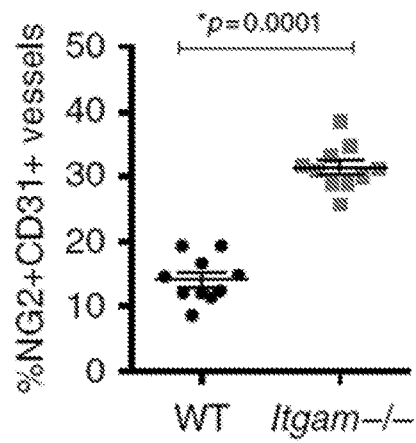
FIG. 2C
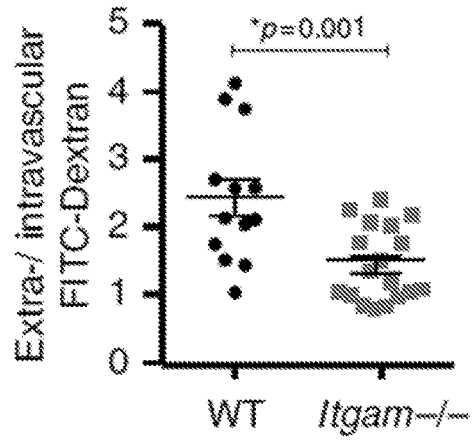
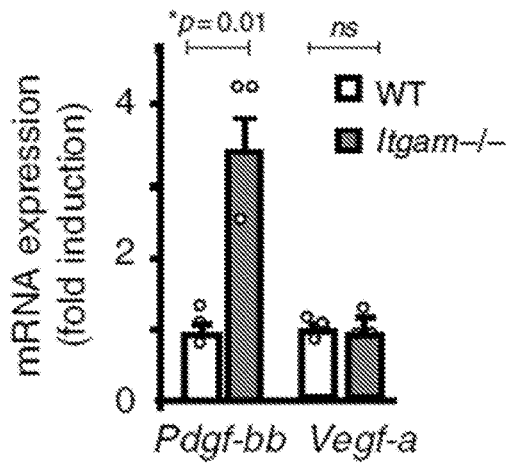
FIG. 2D
FIG. 2E

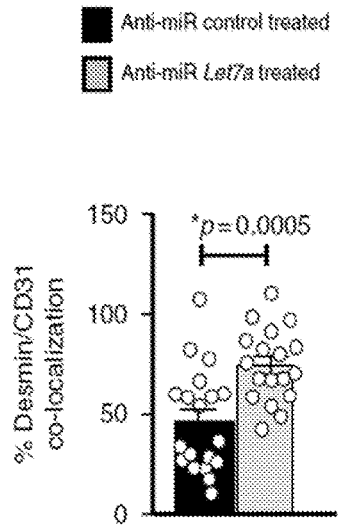
FIG. 4H
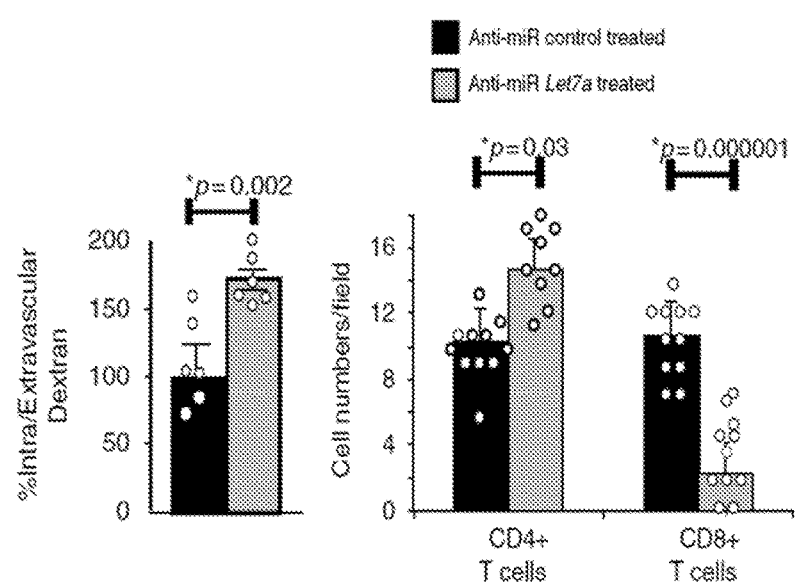
FIG. 4I
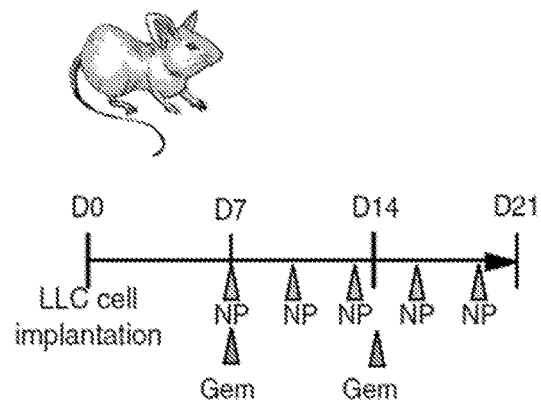
FIG. 4J
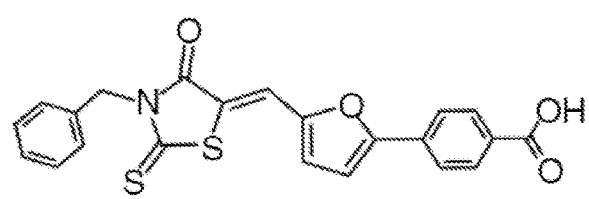
FIG. 5A
FIG. 5B

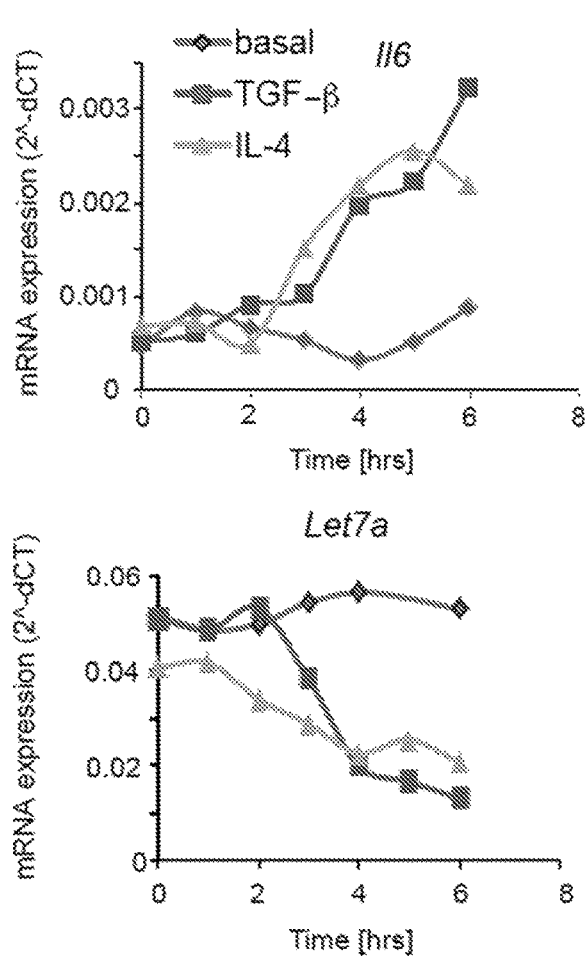
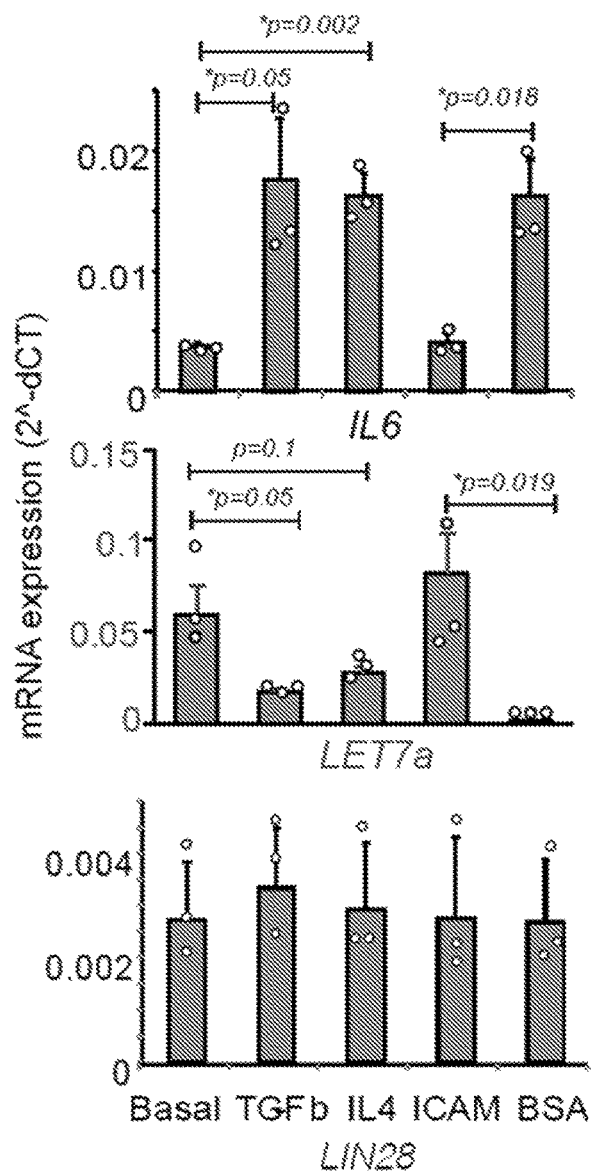
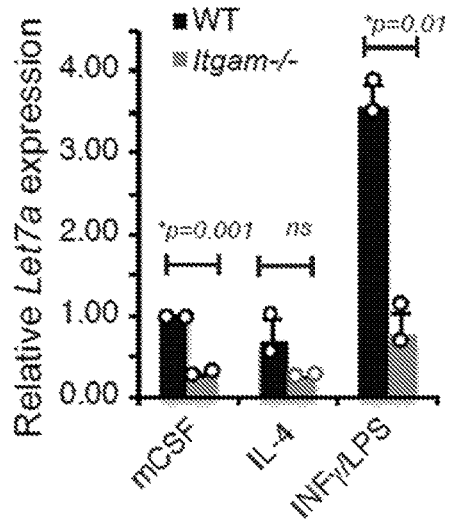
FIG. 11A
FIG. 11B
FIG. 11C

METHODS OF ENHANCING IMMUNITY

CROSS REFERENCE TO RELATED APPLICATION(S)

This application is a national stage application under 35 U.S.C. § 371 of International Application No. PCT/US2019/034525, filed May 30, 2019, which claims the benefit of priority under 35 U.S.C. § 119(e) of U.S. Ser. No. 62/678,134, filed May 30, 2018, the entire content of each of which is incorporated herein by reference in its entirety.

GRANT INFORMATION

This invention was made with government support under CA167426 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 24, 2020, is named 114198-3092 SL.txt and is 10 kilobytes in size.

BACKGROUND OF THE INVENTION

Field of the Invention

The invention relates generally to cancer and more specifically to methods of enhancing immunity by modulating CD11b activity or expression.

Background Information

Macrophages, monocytes, neutrophils, and other myeloid cells play important roles during acute and chronic inflammation. Pro-inflammatory myeloid cells stimulate cytotoxic T cells to suppress infectious disease and tumor growth, while immune suppressive myeloid cells promote tumor progression and wound healing. During acute and chronic inflammation, macrophages express pro-inflammatory cytokines, as well as reactive nitrogen and oxygen species that can kill pathogens as well as normal cells. In contrast, in neoplastic and parasitic diseases, macrophages and immature monocytes and granulocytes (myeloid-derived suppressor cells) express cytokines that induce immune suppression, angiogenesis and cancer progression.

Macrophages isolated from murine and human tumors exhibit an immunosuppressive phenotype that may be induced by cytokines expressed in the tumor microenvironment, such as IL-10 or TGF-β which can induce M2-like macrophage polarization in vitro. The cytokine profile of the tumor microenvironment is therefore extremely important to the phenotype of the local macrophage. Macrophage Colony Stimulating Factor (mCSF) and its receptor CSF1R play important roles in macrophage and monocyte survival in vitro and in vivo, and CSF1R inhibitors are currently in clinical development for cancer therapy.

Although it is well established that tumor associated macrophages (TAM) are abundant within the tumor microenvironment and play essential roles in tumor immune suppression and tumor progression, the molecular mechanisms that regulate these tumor-promoting functions of TAMs remain incompletely clear. However, recent studies have shown that signaling pathways regulated by integrins, CSF1R, PI3Kγ and BTK control myeloid cell trafficking into tumors as well as macrophage polarization and inhibitors of these molecules are also in clinical development for cancer therapy.

Myeloid cells as well as lymphocytes rely on cell adhesion receptors for trafficking into inflamed tissues and tumors. Previous studies on tumor inflammation revealed that immune cell adhesion receptors play critical roles during tumor progression. These studies found that myeloid cell integrin, αMβ2 (CD11b/CD18), a receptor for complement fibrinogen, and endothelial cell ICAM-1, is not required for adhesion to endothelium or trafficking into tumors. In contrast, CD11b/CD18 has been shown to mediate macrophage adhesion, migration, chemotaxis and accumulation during inflammation. Accordingly, a need exists for novel methods of treating cancer that focus on the role that integrin CD11b plays during inflammation.

SUMMARY OF THE INVENTION

The present invention is based on the finding that CD11b signaling inhibits immune suppression, modulates neovascularization and promotes anti-tumor immune responses in models of murine and human cancer.

In one aspect, the invention provides a method of treating cancer in a subject. The method includes administering to a subject in need thereof, a therapeutically effective amount of one or more agonists of CD11b expression. In various embodiments, the subject is human, and the cancer is selected from the group consisting of breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In various embodiments, the agonist of CD11b activity or expression is an antibody, protein or small molecule, such as, for example, miRNA Let7a or leukadherin 1 (LA1). In various embodiments, the one or more agonists of CD11b activity or expression are administered in combination with one or more chemotherapeutic agents. In various embodiments, the chemotherapeutic agent is gemcitabine, pembrolizumab, nivolumab, cemiplimab, atezolizumab, avelumab, durvalumab, or ipilimumab.

In yet another aspect, the invention provides a method of treating cancer. The method includes a therapeutically effective amount of anti-miRNA Let7a in combination with one or more chemotherapeutic agents. In various embodiments, the subject is human and the cancer is selected from the group consisting of breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In various embodiments, the subject is human, and the cancer may be breast cancer or lung cancer. In various embodiments, the anti-miRNA Let7a may be administered in combination with an agonist of CD11b activity or expression such as, for example, miRNA Let7a or leukadherin 1 (LA1). In various embodiments, the chemotherapeutic agent is gemcitabine, pembrolizumab, nivolumab, cemiplimab, atezolizumab, avelumab, durvalumab, or ipilimumab.

In yet another aspect, the invention provides a transgenic non-human mammal whose genome comprises a mutation at Ile332 of exon 9 of the ITGAM gene, wherein the transgenic non-human mammal has the phenotype of loss of the Exon-9

Bgl II restriction site. In various embodiments, the transgenic non-human mammal is a mouse and the Ile332 is substituted with Gly. The invention also provides an isolated cell derived from the transgenic non-human mammal.

In yet another aspect, the invention provides a method of enhancing immunity and/or increasing susceptibility of a cancer cell to treatment with a chemotherapeutic agent. The method includes detecting cancer associated myeloid cells in a sample comprising cancer cells from the subject, contacting the sample with an agonist of CD11b or Let7a and detecting increased levels of CD11b or Let7a as compared to the levels of CD11b or Let7a prior to the contacting, thereby enhancing immunity and/or increasing susceptibility of the cancer cells to treatment with a chemotherapeutic agent. In various embodiments, the chemotherapeutic agent is gemcitabine. In various embodiments, the method further includes detecting an increase in expression of one or more of Arg1, Tgfb, Il10, Il6 or Pdgfb after contacting with the agonist of CD11b or Let7a, as compared to expression prior to contacting. In various embodiments, the method further includes detecting a decrease in expression of one or more of Il12, Ifng, Nos2, or Tnfa after contacting with the agonist of CD11b or Let7a, as compared to expression prior to contacting.

In yet another aspect, the invention provides a method of rendering a cancer cell susceptible to chemotherapeutic treatment. The method includes contacting tumor associated macrophages obtained from a sample comprising the cancer cell with an agonist of CD11b or Let7a activity or expression, thereby rendering the cancer cell susceptible to chemotherapeutic treatment. In various embodiments, the agonist of CD11b activity or expression is an antibody, protein or small molecule, such as, for example, miRNA Let7a or leukadherin 1 (LA1).

In another aspect, the invention provides a method of screening for a therapeutic agent for treating cancer. The method includes administering a test agent to the transgenic non-human mammal described herein and evaluating the effect of the test agent on at least one of expression levels of CD11b or Let7a in at least one disease-relevant tissue of the transgenic non-human mammal, wherein at least one of: an increase in the amount of CD11b expression, an increase in the amount of Let7a expression, or increase in the amount of CD11b expression and an increase in the amount of Let7a expression in at least one disease-relevant tissue relative to a similar transgenic non-human mammal that does not receive the test agent indicates the test agent is therapeutic for the cancer. In various embodiments, the method also includes detecting increases in expression of one or more of Il1b, Tnfa, Il12, Nos2 and Ifng in at least one disease-relevant tissue relative to a similar transgenic non-human mammal that does not receive the test agent, thereby confirming that the test agent is therapeutic for the cancer.

BRIEF DESCRIPTION OF THE DRAWINGS

FIG. 1A shows relative mRNA expression of pro- and anti-inflammatory cytokines in bone marrow derived macrophages (BMDM) from WT (white bars) or Itgam–/– mice (n=2-8). FIG. 1B shows relative mRNA expression of pro- and anti-inflammatory cytokines in tumor associated macrophages (TAM) from WT (white bars) and Itgam–/– mice bearing LLC lung carcinoma tumors (n=2-4). FIG. 1C shows relative mRNA expression of pro- and anti-inflammatory cytokines in Itgam–/– and Itgam or non-silencing siRNA transfected macrophages (n=2-4); inset: cell surface expression levels of CD11b in transfected macrophages. FIG. 1D shows relative mRNA expression of WT macrophages in the presence of non-specific (IgG) or anti-CD11b antibodies (n=3). FIG. 1E shows relative mRNA expression of murine adherent to ICAM-1, VCAM-1 or BSA coated plates (Susp) (n=3). FIG. 1F shows relative mRNA expression of human macrophages adherent to ICAM-1, VCAM-1 or BSA coated plates (Susp) (n=3). FIG. 1G shows immunoblotting of phosphoSER536 and total p65 RelA (NFκB) in WT and Itgam–/– macrophages stimulated with IFNγ+LPS; graph depicts quantification of relative pSer536 expression in WT (white bars) and Itgam–/– BMDM. FIGS. 1H-1I show LLC tumor growth in WT and Itgam–/– mice adoptively transferred with bone marrow derived (FIG. 1H) and tumor derived (FIG. 1I) WT or Itgam–/– macrophages. FIG. 1J shows relative mRNA expression cytokines in whole LLC tumors from WT (white bars) and Itgam–/– mice (n=3). FIG. 1K shows LLC lung (n=17), B16 melanoma (n=9) and autochthonous PyMT mammary (n=10-14) tumor weight in WT (black dots) and Itgam–/– (lighter dots) mice. FIG. 1L shows tumor weight and volume of LLC tumors grown in WT (black dots) versus Itgam I332G knockin mice (lighter dots) (n=6-7). Error bars indicate sem. "n" indicates biological replicates. p<0.05 indicates statistical significance determined by Student's t-test for FIGS. 1A-1G and 1J; and by Anova with Tukey post-hoc testing for FIGS. 1H, 1I, 1K and 1L.

FIGS. 2A-2I are graphical and pictorial diagrams showing that CD11b suppresses PDGF-BB-dependent neovascularization and tumor growth. FIG. 2A shows CD31, Desmin, NG2, Smooth muscle actin (SMA) and Dextran immunostaining of blood vessels in LLC tumors from WT (white bars) and Itgam–/– mice (n=10). FIG. 2B shows blood vessel density (vessels/field) and number of vessel branch points/field in LLC tumors from WT (white bars) and Itgam–/– animals (n=10). FIG. 2C shows percent CD31+/SMA+, CD31+/Desmin+, CD31+/NG2+ vessels in tumors from WT (black dots) and Itgam–/– mice (n=5). FIG. 2D shows ratio of extravascular to intravascular FITC-dextran in LLC tumors from WT (black dots) and Itgam–/– mice (n=5). FIGS. 2E-2F show Pdgfb and Vegfa mRNA (FIG. 2E) (n=3) and PDGF-BB protein expression (FIG. 2F) (n=12) in LLC tumors from WT (white bars) and Itgam–/– mice (n=3). FIG. 2G shows (left), FITC-Isolectin staining of whole mount retinas from newborn WT and Itgam–/– mice; and (right), percent neovascularization at P1, P4 and P9 retinas in WT (white bars) and Itgam–/– mice (n=5). FIG. 2H shows Desmin and CD31 immunostaining of LLC tumors from Imatinib and vehicle-treated WT or Itgam–/– mice. FIG. 2I shows tumor weight, number of blood vessels/field and percent Desmin/CD31 vessels per field from FIG. 2H (n=10). Bar on micrographs indicates 50 µm. Error bars indicate sem. "n" indicates biological replicates. p<0.05 indicates statistical significance, as determined by Student's t-test for FIGS. 2B-2G and by Anova with Tukey's post-hoc testing for FIG. 2I.

FIG. 3A shows relative mRNA expression of pro- and anti-inflammatory factors in WT (white bars) and Itgam–/– macrophages incubated with and without the Stat3 inhibitor 5,15 DPP; inset; Stat3 phosphorylation in WT and Itgam–/– macrophages (n=2-3). FIG. 3B shows relative mRNA expression of pro- and anti-inflammatory factors in IL6-stimulated human (white bars) and murine bone marrow-derived macrophages and murine bone marrow derived (BM) myeloid cells (n=3); p<0.05 with these exceptions: mBMM (Ifng, Il12b); mCD11b+(Arg1, Pdgfb, Il12b and Il1b); hBMM (Arg1, Ifng, Il1b). FIG. 3C shows relative mRNA expression of Il6 and Pdgfb in WT and Itgam−/− cells transduced with non-silencing (white bars) or Il6 siRNA (n=3). FIG. 3D shows relative Let7a expression in murine macrophages transduced with non-silencing (white bars) or Itgam siRNAs, macrophages incubated with control IgG (white bars) or neutralizing anti-CD11b antibodies, and WT (white bars) or Itgam−/− macrophages (n=3). FIG. 3E shows time course of Let7a (left) and Il6 (right) expression in WT murine CD11b+ cells seeded on ICAM-1 (solid line) or maintained in suspension (n=3). FIG. 3F shows relative expression of miRNA Let7a and Il6 in human macrophages adherent to ICAM-1 (dark bars) or maintained in suspension (white) (n=3). FIG. 3G shows relative mRNA expression of inflammatory factors in WT and Itgam−/− BMM transduced with control (white bars), pre-miRNA Let7a or anti-miRNA Let7a (n=3). FIG. 3H shows relative Pdgfb and Vegfa expression in WT BMM transduced with control (white bars) or anti-miRNA Let7a (n=3). FIG. 3I shows time course of c-Myc expression in IL-4 or IFNγ+LPS stimulated WT (black lines) or Itgam−/− macrophages (n=3). FIG. 3J shows time course of c-myc protein expression and pSer62 phosphorylation in WT and Itgam−/− macrophages. FIG. 3K shows relative mRNA expression of miRNAs Let7a (white bars), Let7d and Let7f in basal, IL-4, or IL-4+c-myc inhibitor treated WT and Itgam−/− macrophages (n=3). FIG. 3L shows relative mRNA expression of Il6, Arg1, and Pdgfb in IL-4 stimulated WT (white bars) and Itgam−/− macrophages treated with or without (white bars) c-Myc inhibitor 10058-F4. Error bars indicate sem. "n" indicates biological replicates. *p<0.05 indicates statistical significance determined by Student's t-test for FIGS. 3A and 3D-3F, and Anova with Tukey's post-hoc testing for FIGS. 3B, 3G 3K.

FIGS. 4A-4K are graphical and pictorial diagrams showing macrophage microRNA let-7a is required for tumor growth suppression. FIGS. 4A-4B show endothelial cells and vascular smooth muscle cells attached to microcarrier beads were cultured in fibrin gels containing WT or Itgam−/− BMMs transduced with control miRNA, pre-miRNA Let7a, anti-miRNA Let7a or Pdgf-bb siRNA. Images (FIG. 4A) and histograms (FIG. 4B) of CD31+ positive vessel length (mm) (n=10). FIG. 4C shows CD31 and SMA immunostaining of sections from in vivo cultured bFGF-saturated Matrigel plugs containing BMM transduced with control miR (black bars) or anti-miR Let7a; quantification of the percentage of SMA+ vessels per matrigel plug (n=25). FIG. 4D shows schematic and graph of targeted delivery of anti-miR Let7a in animals with LLC tumors; tumor volumes from control anti-miRNA (black line) or anti-miRNA Let-7a treated animals (n=10). FIG. 4E shows Let7a expression in cell populations sorted from peripheral blood and tumors from control (black bars) and anti-miRNA Let7-treated animals from FIG. 4D (n=3). FIG. 4F shows relative mRNA expression of inflammatory factors in sorted macrophages from FIG. 4D (n=3). FIG. 4G shows representative images of CD31/Desmin co-localization and FITC-Dextran localization in treated tumors from FIG. 4D. FIG. 4H shows quantification of the percentage of CD31/Desmin co-localization (n=30) and of FITC-dextran leakage into tissues (n=25). FIG. 4I shows CD4+ and CD8+ cells/field in tumors from control anti-miR (black bars) or anti-miR let-7a transduced animals (n=25) scale bars, 40 μm. FIG. 4J shows a schematic representation of chemotherapeutic treatment in combination with targeted delivery of anti-miR-let7a. FIG. 4K shows volumes and endpoint weights of LLC tumors in animals transduced with control anti-miR (black), anti-miR let-7a, control anti-miR/Gemcitabine, and anti-miR let7a/Gemcitabine (n=10). Bar on micrographs indicates 50 μm. Error bars indicate sem. "n" indicates biological replicates. *p<0.05 indicates statistical significance by Student's t-test for FIGS. 4C-4I and by Anova with Tukey's post-hoc testing for FIG. 4J.

FIGS. 5A-5M are pictorial and graphical diagrams showing that Integrin CD11b agonism suppresses tumor growth and promotes survival in mouse models of cancer. FIG. 5A shows the structure of LA1. FIG. 5B shows adhesion of macrophages in the absence or presence of $Ca^{2+}$ $Mg^{2+}$ (white bars), $Mn^{2+}$ (black bars), LA1 or LA1+neutralizing anti-CD11b (n=3). FIG. 5C shows relative mRNA expression of Let7a, Il16 or Pdgfb in control (black bars) and LA1-treated macrophages (n=3). FIG. 5D shows tumor weights 16 days after implantation of LLC cells mixed 1:1 with control-treated (dots), DMSO-treated (triangles) or LA1-treated (diamonds) tumor-derived macrophages (n=8). FIG. 5E shows tumor growth curves as represented by volumes from FIG. 5D. FIG. 5F shows the effect of LA1 on in vitro proliferation of LLC cells and macrophages (n=4). FIG. 5G shows tumor volumes of orthotopic CL66 breast tumors treated with vehicle (black line), Taxol, LA1 or LA1+Taxol (n=10-15). FIG. 5H shows tumor volumes of orthotopic CL66 tumors treated with vehicle (black line), irradiation (IR, 20 Gy), LA1 (2 mg/kg), or LA1+IR (n=9). Figure SI shows tumor volumes of orthotopic human MDA MB-231 mammary xenografts treated with vehicle (control, black line), Taxol, or LA1 (n=7). FIGS. 5J-5K show mean LLC subcutaneous tumor volumes of WT (black line) (FIG. 5J) and Itgam−/− (FIG. 5K) mice treated with and without LA1 (n=6). FIG. 5L shows images and quantification of SMA/CD31 expression in blood vessels of control (black bars) and LA1 treated animals from FIGS. 5G, 5I and 5J. Bar on micrographs indicates 50 μm. FIG. 5M shows a schematic depicting role of CD11b activation in the control of immune stimulation. Error bars indicate SEM. "n" indicates biological replicates. *p<0.5 indicates statistical significance by Student's t-test FIGS. 5C and 5F; Anova with Tukey post-hoc testing for FIGS. 5D-5E; unpaired t-test FIGS. 5G and 5I; Mann-Whitney t-test FIGS. 5B and 5J-5L; Wilcox test FIG. 5H.

FIG. 7A shows expression of immune cell markers and integrins in BM derived leukocytes from WT (black bars) and Itgam−/− (light bars) mice (n=4). FIGS. 7B and 7C show graphs and FACs profiles indicating proportions of $Gr1^{hi}$ granulocytes and $Gr1^{lo}$ monocytes in bone marrow (FIG. 7B) and peripheral blood (FIG. 7C) in WT (black bars) and Itgam−/− (light bars) mice. FIGS. 7C and 7D shows graphs indicating proportions of $Gr1^{neg}$ $F/480^{hi}$ macrophages, $GR1^{lo}$ $F/480^{i}$ monocytes and $Gr1^{hi}F/480^{neg}$ granulocytes in LLC tumors from WT (black bars) and Itgam−/− mice. FIG. 7E shows mRNA expression of pro- and anti-inflammatory factors in basal, IL-4 and IFNγ/LPS-stimulated WT (black bars) and Itgam−/− in vitro cultured BM macrophages (n=4). FIG. 7F shows concentrations (pg/ml) of IL-6 and TNFα secreted by WT (black bars) and Itgam−/− BMDM. FIG. 7G shows mRNA expression of pro- and anti-inflammatory factors in WT (black bars) and Itgam−/− TAMs from LLC tumors (n=3-4). FIG. 7H shows relative mRNA expression of immune response genes in human macrophages adherent on ICAM-1 or maintained in suspension (n=3). Error bars indicate sem. "n" indicates biological replicates. *p (<0.05) indicates statistical significance by Student's t-test.

FIG. 8A shows representative FACs profiles and quantification of CD4+, CD8+ and CD4+CD25+FoxP3+ T cells in WT (black bars) and Itgam−/− tumors (n=4). FIG. 8B shows images and quantification of CD4 and CD8 immunostaining in LLC tumors from WT (black bars) and Itgam−/− mice (n=10). In images, bar indicates 50 µm. FIG. 8C shows representative FACs profiles of CD11b expression on neutrophils and monocytes from peripheral blood of Itgam−/− (KO) and Itgam I332G knockin (KI) mice; quantification of mean fluorescent intensities of CD11b on neutrophils and monocytes from peripheral blood of WT, Itgam−/− (KO) and Itgam I332G knockin (KI) mice (n=5). FIG. 8D shows absolute numbers of white blood cells, red blood cells, neutrophils, lymphocytes, monocytes, eosinophils and basophils in WT (black bars, n=13) Itgam−/− (KO) (grey bars, n=8) and Itgam I332G knockin (KI) (white bars, n=4) mice. FIG. 8E shows percent adhesion to ICAM-coated surfaces of bone marrow derived macrophages from WT (white bars) and Itgam I332G knockin mice (black bars) in the presence of physiological concentration of Ca' and $Mg^{2+}$ or in the presence of $Mn^{2+}$ (n=4). Bar on micrographs indicates ×50 µm. n=number of biological replicates. *p (<0.05) indicates statistical significance determined by Student's t-test (FIGS. 8A and 8B) and Mann-Whitney t-test (FIGS. 8C-8E).

FIG. 9A shows FACS profile of CD11b expression levels in bone marrow derived macrophages stimulated with LPS/IFNγ, IL-4, or basal media (black lines) (n=3). FIG. 9B shows quantification of CD11b mean fluorescence intensities (MFI) in bone marrow derived macrophages stimulated with LPS/IFNγ, IL-4, or basal (black bars) media (n=3). FIG. 9C shows quantification of CD11b MFI in bone marrow derived macrophages stimulated with MCSF (Control), TGFβ, or IL10 (n=3). FIG. 9D shows Cd11b mRNA expression in WT bone marrow derived macrophages stimulated with TGFβ, IL-4, tumor conditioned medium (TCM), IL-10 or IL-6 (n=3). FIG. 9E shows FACS profiles of CD11b expression levels in bone marrow derived macrophages stimulated with basal media (black lines), TCM (lower panels) or TGFβ (lower panels) in the absence (Control, left panels) or presence (+SB525334, right panels) of the TGFβR1 inhibitor SB525334 (n=3). FIG. 9F shows quantification of CD11b MFI in bone marrow derived macrophages stimulated with MCSF (basal) or TGFβ in the absence (control) or presence of the TGFβR1 inhibitor SB525334 (n=3). FIG. 9G shows relative mRNA expression of WT and Cd11b−/− bone marrow derived macrophages stimulated with mCSF (basal), TGFβ or tumor conditioned medium (TCM) in the presence and absence of the TGFβR1 inhibitor (SB525334) (n=3). Error bars indicate sem. "n" indicates biological replicates. *p (<0.05) indicates statistical significance by Anova with Tukey's post-hoc testing (FIGS. 9B-9G).

FIG. 10A shows images of CD31/DAPI and CD31/SMA immunofluorescence staining of mammary tumors from PyMT WT and Itgam−/− animals. Bar indicates 50 µm. FIG. 10B shows percentage of CD31/SMA+ vessels in WE (black bars) and Itgam−/− tissues from FIG. 10A (n=10). FIG. 10C shows relative mRNA expression of Pdgfb and Vegfa in mammary tumors from WT (black bars) and CD11b−/− PyMT+ animals (n=4). Error bars indicate sem. "n" indicates biological replicates. *p (<0.05) indicates statistical significance by Student's t-test (FIGS. 10B-10C).

FIGS. 11A-11F are pictorial and graphical diagrams showing let7a expression and role in macrophages. FIG. 11A shows time course of expression of Il6 mRNA (upper panel) or miRNA Let7a (lower panel) in mCSF-1 (basal), TGFβ or IL-4 stimulated murine macrophages in vitro (n=2). FIG. 11B shows relative expression levels of IL6, LET7a and LIN28 expression in human bone marrow derived macrophages treated with mCSF (basal), TGFβ or IL-4 or adherent to ICAM-1 vs in suspension (BSA) (n=3). FIG. 11C shows relative expression levels of Let7a in mCSF-1 (basal), IL-4 or IFNγ/LPS stimulated WT (black bars) or Itgam−/− murine bone marrow derived macrophages in vitro (n=2). FIG. 11D shows relative expression levels of Lin28 in total murine bone marrow myeloid cells (BM, black bars) or bone marrow derived murine macrophages (BMM) (n=3). FIG. 11E shows relative expression levels of Lin28 in BMMs that were treated with basal medium, TGFβ or IL-6 (n=3). FIG. 11F shows endothelial cells and vascular smooth muscle cells attached to microcarrier beads were cultured in fibrin gels containing WT or Itgam−/− BMMs transduced with control miRNA, miRNA Let7a, or anti-miRNA Let7a. Left: Images of representative anti-miR Let-7A and control treated cultures. Right: Histograms of the lengths of CD31+ positive vessels in cultures containing WT (black bars) or Itgam−/− BMMs (n=10). Error bars indicate sem. "n" indicate biological replicates. *p (<0.05) indicates statistical significance by Student's t-test for panels (FIGS. 11C-11E). Anova with Tukey post-hoc testing for panel (FIG. 11B).

FIG. 12A shows representative flow cytometric profiles of c control IgG (black line), anti-integrin α4 (right) and anti-integrin β3 (left) immunostained murine peripheral blood CD11b+ myeloid cells. FIG. 12B (left) shows percent integrin β3 (CD61) positive T, B and myeloid cells in circulation in naïve (white bars) and LLC tumor bearing mice (n=3); right shows representative histograms illustrating CD11b expression in these populations. FIG. 12C shows representative BODIPY+ flow cytometric profiles of CD11b+Gr1lo monocytes and CD11b+ Gr1hi granulocytes after in vitro administration of RGD-targeted (black) or non-targeted BODIPY-nanoparticles, compared to untreated cells (filled grey histogram). FIG. 12D shows quantification of mean BODIPY+ fluorescence intensity induced in CD11b+Gr1lo monocytes and CD11b+ Gr1hi granulocytes by incubation with RGD-targeted (black) or non-targeted BODIPY-nanoparticles from FIG. 12C (n=3). FIG. 12E shows representative flow cytometric profiles of BODIPY+CD11b+ and Gr1+ peripheral blood mononuclear cells from tumor-bearing mice 2 h after administration of RGD-targeted or non-targeted BODIPY-nanoparticles (n=3). FIG. 12F shows histograms of relative levels of BODIPY uptake by RGD-targeted (black lines) or non-targeted BODIPY-nanoparticles in circulating CD11b+ Gr1lo monocytes and CD11b+Gr1hi granulocytes from FIG. 12E. FIG. 12G shows mean fluorescence intensity of RGD-targeted (black bars) or non-targeted of BODIPY-nanoparticles in CD11b+Gr1lo monocytes and CD11b+Gr1hi granulocytes from FIG. 12E (n=3). FIG. 12H shows quantification of percent BODIPY+CD11b+ myeloid cells, Gr1+ myeloid cells, T cells and B cells in peripheral blood 2 h after administration of RGD-targeted nanoparticles to naïve (black bars) or tumor bearing animals (n=3). Error bars indicate sem. "n" indicates biological replicates. *p (<0.05) indicates statistical significance by Student's t-test (FIGS. 12D, 12G and 12H).

FIG. 13A shows mRNA expression of inflammatory factors in sorted macrophages from LLC tumor-bearing mice treated with control miRNA (black bars) or anti-miR Let7a (n=3). FIG. 13B shows weight of LLC tumors from WT and Itgam−/− mice treated with or without gemcitabine (n=4-6). Error bars indicate sem. "n" indicates biological replicates. FIG. 13C shows percent perfusion (% intravascular FITC-dextran) in mice from (n=8 fields). *p 0.05) indicates statistical significance by Student's t-test for FIG. 13A and Anova with Tukey's post-hoc testing for FIGS. 13B and 13C.

FIG. 14A shows mRNA expression of inflammatory cytokines in vehicle (dark bars) or LA1 (light bars) treated IFNγ+LPS stimulated bone marrow derived murine macrophages (n=3). FIG. 14B shows the effect of LA1 (left) or taxol (right) on CL66-Luc breast tumor cell survival in vitro (n=3). FIG. 14C shows images and quantification of CD206+F4/80+ and MHC-II+F4/80+ expression in LA1 (gray bars) and vehicle (black bars)-treated LLC tumors (n=5). FIG. 14D shows images and quantification of CD206+F4/80+ and MHC-II+F4/80+ expression in vehicle (black bars), taxol, LA1 and taxol+LA1-treated CL66-Luc tumors (n=5). FIG. 14E shows images and quantification of CD11b, S100A9 and MMP9 expression in LA1 (gray bars) and vehicle (black bars)-treated LLC tumors (n=5). FIG. 14F shows images of and quantification of LA1, taxol, taxol+LA1 and vehicle-treated (black bars) CL66-Luc tumor cryosections immunostained to detect S100A9, MMP9, and Arg1. Error bars indicate sem. "n" indicated biological replicates. *p 0.05) indicates statistical significance determined by Student's t-test for FIGS. 14A, 14C and 14E, and by Anova with Tukey's post-hoc testing for FIGS. 14D and 14F.

FIG. 15A shows FACs gating scheme for analysis of T cells in LA1 treated tumors. FIG. 15B shows representative FACs profiles and quantification of CD4+ and CD8+ T cells in LA1 (n=10) and vehicle (DMSO) treated (black dots, n=10) LLC tumors. FIG. 15C shows images of and quantification of cryosections of CL66-Luc tumors from vehicle-(black bars), taxol, LA1 and LA1+taxol treated tumors that were immunostained to detect CD4 and CD8 (n=8-16). Error bars indicate sem. "n" indicated biological replicates. Bar indicates 50 µm. *p (<0.05) indicates statistical significance as determined by Student's t-test for FIG. 15B and by Anova with Tukey's post-hoc testing for FIG. 15C.

DETAILED DESCRIPTION OF THE INVENTION

Figure 1A:
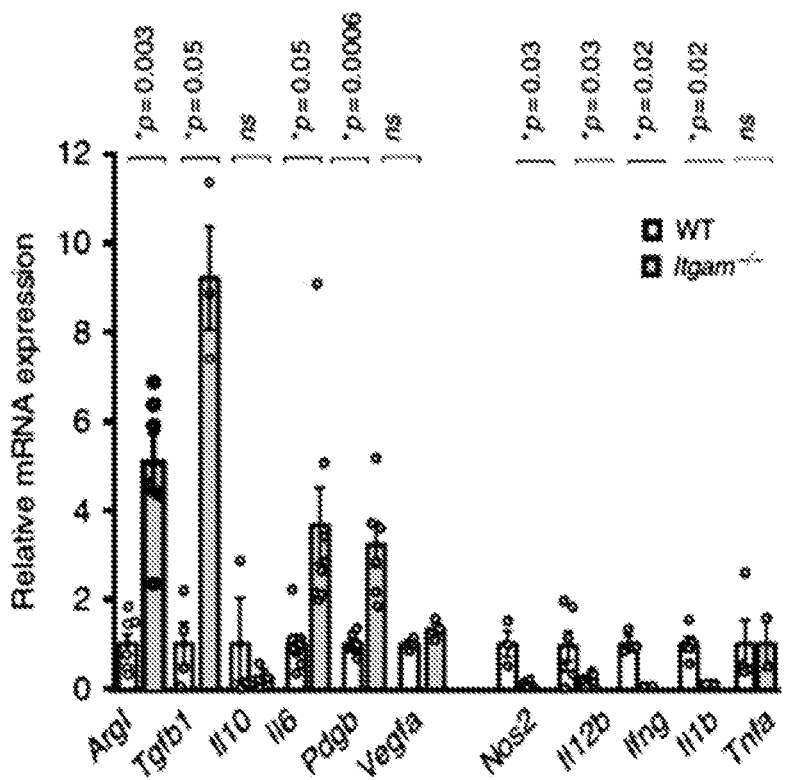
FIGS. 1A-1L are graphical and pictorial diagrams showing CD11b ligation promotes pro-inflammatory macrophage signaling.

The present invention is based on the observation that CD11b signaling in myeloid cells inhibits immune suppression, modulates neovascularization and promotes anti-tumor immune responses in models of murine and human cancer.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present invention include precancerous (e.g., benign), malignant, pre-metastatic, metastatic, and non-metastatic cells. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

The term "biological sample," refers to any sample taken from a participant, including but not limited to cells, blood, tissue, skin, urine, etc.

The term "pharmaceutically acceptable," when used in reference to a carrier, is meant that the carrier, diluent or excipient must be compatible with the other ingredients of the formulation and not deleterious to the recipient thereof.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration or administration via intranasal delivery.

The term "effective amount" or "therapeutically effective amount" refers to the amount of an active agent sufficient to induce a desired biological result. That result may be alleviation of the signs, symptoms, or causes of a disease, or any other desired alteration of a biological system, including inhibition or reduction in cancer cell growth and/or induction of cancer cell death (i.e., apoptosis). Thus, the term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation. In some embodiments, the "effective amount" may be administered before, during, and/or after any treatment regimens for cancer.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For purposes of this invention, beneficial or desired clinical results include, but are not limited to, treatment of cancer, such as breast cancer.

As used herein, "promote" or "increase," or "promoting" or "increasing" are used interchangeably herein. These terms refer to the increase in a measured parameter (e.g., activity, expression, signal transduction, neuron degeneration) in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit," "prevent" or "reduce," or "inhibiting," "preventing" or "reducing" are used interchangeably herein. These terms refer to the decrease in a measured parameter (e.g., activity, expression, signal transduction, neuron degeneration) in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is undetectable (i.e., completely inhibited) in the treated cell in comparison to the untreated cell.

The term "selective inhibition" or "selectively inhibit" as referred to a biologically active agent refers to the agent's ability to preferentially reduce the target signaling activity as compared to off-target signaling activity, via direct or indirect interaction with the target.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, and synthetic nucleic acids. A transcription termination sequence will usually be located 3' to the coding sequence.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process. Thus, in various embodiments, the promoter may be a stem cell-specific promoter that drives transgene expression. For example, constitutive promoters of different strengths can be used. Expression vectors and plasmids in accordance with the present invention may include one or more constitutive promoters, such as viral promoters or promoters from mammalian genes that are generally active in promoting transcription. Exemplary promoters include, but are not limited to, human Elongation Factor 1 alpha promoter (EFS), SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a Rous sarcoma virus (RSV) promoter, synthetic promoters, hybrid promoters, and the like.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, a "regulatory gene" or "regulatory sequence" is a nucleic acid sequence that encodes products (e.g., transcription factors) that control the expression of other genes.

As used herein, the terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatized variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')2 fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

As used herein, "transgenic organism" refers to an animal in which exogenous DNA has been introduced while the animal is still in its embryonic stage. In most cases, the transgenic approach aims at specific modifications of the genome, e.g., by introducing whole transcriptional units into the genome, or by up- or down-regulating or mutating pre-existing cellular genes. The targeted character of certain of these procedures sets transgenic technologies apart from experimental methods in which random mutations are conferred to the germline, such as administration of chemical mutagens or treatment with ionizing solution. A transgenic organism can include an organism which has a gene knock-out or may result for inducing a genetic mutation.

A "genetic knock out" refers to partial or complete suppression of the expression of a protein encoded by an endogenous DNA sequence in a cell. The "knockout" can be affected by targeted deletion of the whole or part of a gene encoding a protein. Alternatively, the transgenic organism can be obtained by the targeted mutation of a functional protein in an embryonic stem cell. As a result, the deletion or mutation may prevent or reduce the expression of the protein in any cell in the whole animal in which it is normally expressed, or results in the expression of a mutant protein having a biological function different than the normal/wild-type protein.

A "genetic knock in" refers to one-for-one substitution of DNA sequence information in a genetic locus or the insertion of sequence information not found within the locus of a cell. Traditionally, knock-in techniques have relied on homologous recombination to drive targeted gene replacement, although other methods using a transposon-mediated system to insert the target gene have been developed. Embryonic stem cells with the modification of interest are implanted into a viable blastocyst, which will grow into a mature chimeric animal with some cells having the original blastocyst cell genetic information and other cells having the modifications introduced to the embryonic stem cells. Subsequent offspring of the chimeric animal will then have the gene knock-in. Other methods of making transgenic animals are also generally known. See, for example, Manipulating the Mouse Embryo, (Cold Spring Harbor Laboratory Press, Cold Spring Harbor, N.Y., 1986).

The term "knockout animal" and "transgenic animal", refer to a transgenic animal wherein a given gene has been suppressed or mutated by recombination with a targeting vector. Similarly, a "knockin animal" refers to a transgenic animal wherein a given gene has been inserted into a specific locus (i.e., targeted insertion) resulting in a gain-of-function mutation. It is to be emphasized that these terms are intended to include all progeny generations. Thus, the founder animal and all F1, F2, F3, and so on, progeny thereof are included.

Animals containing more than one transgenic construct and/or more than one transgene expression construct may be prepared in any of several ways. An exemplary manner of preparation is to generate a series of animals, each containing one of the desired transgenic phenotypes. Such animals are bred together through a series of crosses, backcrosses and selections, to ultimately generate a single animal containing all desired transgenic traits and/or expression constructs, where the animal is otherwise congenic (genetically identical) to the wild type except for the presence of the construct(s) and/or transgene(s).

Accordingly, in one aspect, the invention provides a transgenic non-human mammal such as a mouse whose genome comprises a heterozygous or homozygous replacement of exon 9 of the ITGAM gene in which the Ile332 codon was substituted with Gly, and methods of making the same. In various embodiments, the mouse has the phenotype of loss of the Exon-9 Bgl II restriction site. Also provided is an isolated cell derived from the transgenic non-human mammal.

The amino acid sequences for the *Mus musculus* (mouse) gene is known in the art. See, for example, Accession No. P05555, ITAM_Mouse, which provides the amino acid sequence (SEQ ID NO: 1):

MTLKALLVTALALCHGFNLDTEHPMTFQENAKGFGQNVVQLGGTSVVVA

APQEAKAVNQTGALYQCDYSTSRCHPIPLQVPPEAVNMSLGLSLAVSTV

PQQLLACGPTVHQNCKENTYVNGLCYLFGSNLLRPPQQFPEALRECPQQ

ESDIVFLIDGSGSINNIDFQKMKEFVSTVMEQFKKSKTLFSLMQYSDEF

RIHFTFNDFKRNPSPRSHVSPIKQLNGRTKTASGIRKVVRELFHKTNGA

RENAAKILVVITDGEKFGDPLDYKDVIPEADRAGVIRYVIGVGNAFNKP

QSRRELDTIASKPAGEHVFQVDNFEALNTIQNQLQEKIFAIEGTQTGST

SSFEHEMSQEGFSASITSNGPLLGSVGSFDWAGGAFLYTSKDKVTFINT

TRVDSDMNDAYLGYASAVILRNRVQSLVLGAPRYQHIGLVVMFRENFGT

WEPHTSIKGSQIGSYFGASLCSVDMDADGNTNLILIGAPHYYEKTRGGQ

VSVCPLPRGRARWQCEALLHGDQGHPWGRFGAALTVLGDVNGDKLTDVA

IGAPGEQENQGAVYIFYGASIASLSASHSHRIIGAHFSPGLQYFGQSLS

GGKDLTMDGLMDLAVGAQGHLLLLRAQPVLRLEATMEFSPKKVARSVFA

CQEQVLKNKDAGEVRVCLRVRKNTKDRLREGDIQSTVTYDLALDPVRSR

IRAFFDETKNNTRRRTQVFGLMQKCETLKLILPDCVDDSVSPIILRLNY

TLVGEPLRSFGNLRPVLAMDAQRFFTAMFPFEKNCGNDSICQDDLSITM

SAMGLDTLVVGGPQDFNMSVTLRNDGEDSYGTQVTVYYPSGLSYRKDSA

SQNPLTKKPWFVKPAESSSSSEGHGALKSTTWNINHPIFPANSEVTFNV

TFDVDSHASFGNKLLLKAIVASENNMSRTHKTKFQLELPVKYAIYMIVT

SDESSIRYLNFTASEMTSKVIQHQYQFNNLGQRSLPVSVVFWIPVQINN

VTVWDHPQVIFSQNLSSACHTEQKSPPHSNFRDQLERTPVLNCSVAVCK

RIQCDLPSFNTQEIFNVTLKGNLSFDWYIKTSHGHLLLVSSTEILFNDS

AFALLPGQESYVRSKTETKVEPYEVHNPVPLIVGSSIGGLVLLALITAG

LYKLGFFKRQYKDMMNEAAPQDAPPQ

Macrophages are phagocytes that serve as a first line of defense against pathogenic insults to tissues. These innate immune cells mount proinflammatory responses to pathogens and repair damaged tissues. However, tumor-associated macrophages (TAMs) express cytokines and chemokines that can suppress antitumor immunity and promote tumor progression. Preclinical studies have identified crucial pathways regulating the recruitment, polarization, and metabolism of TAMs during tumor progression.

Figure 7A:
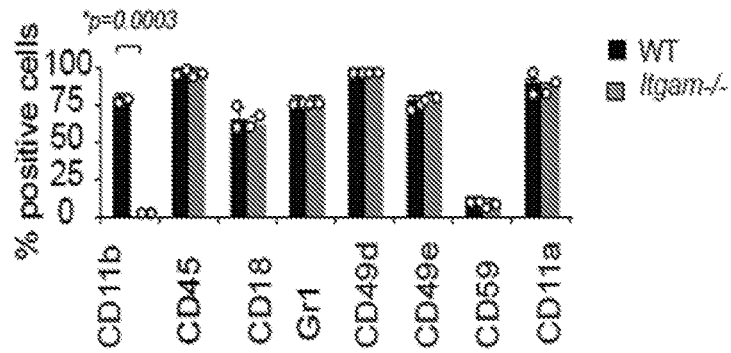
FIGS. 7A-7H are graphical diagrams showing immune profiles of normal and tumor tissues of Itgam−/− mice.
Figure 7B:
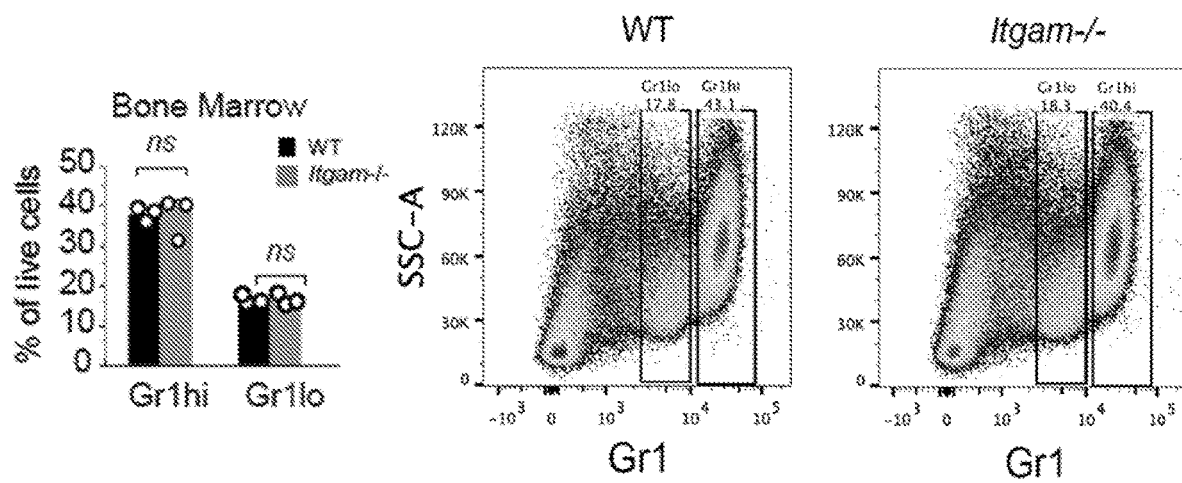
Figure 7C:
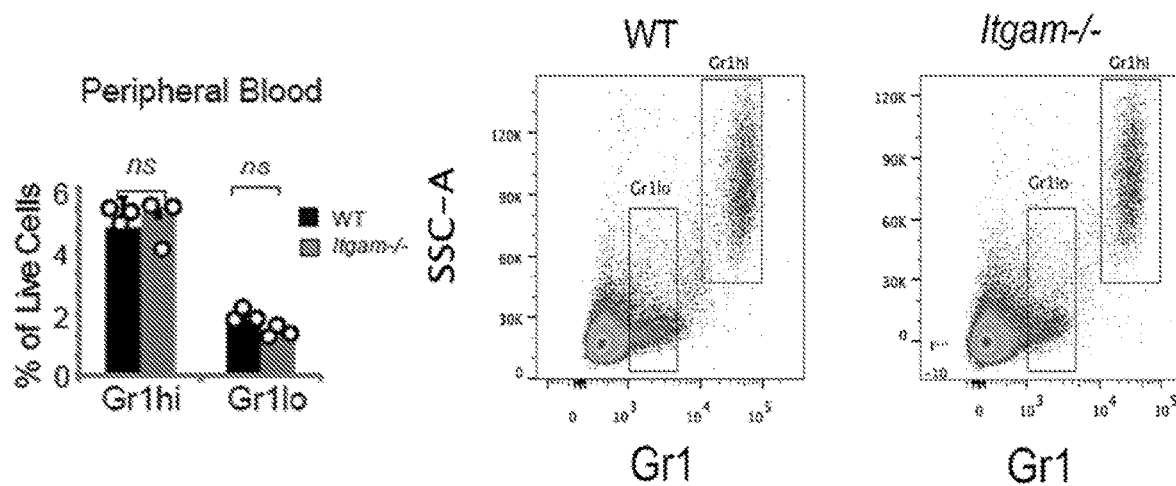
Figure 7D:
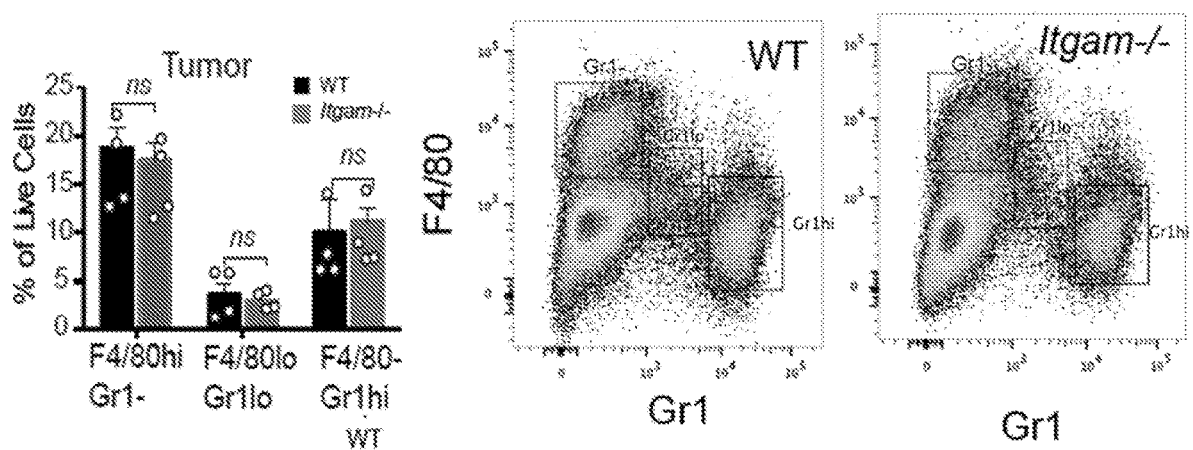
Figure 7F:
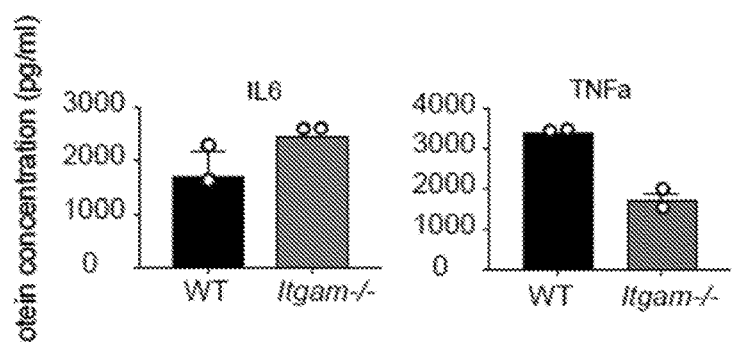
Figure 7E:
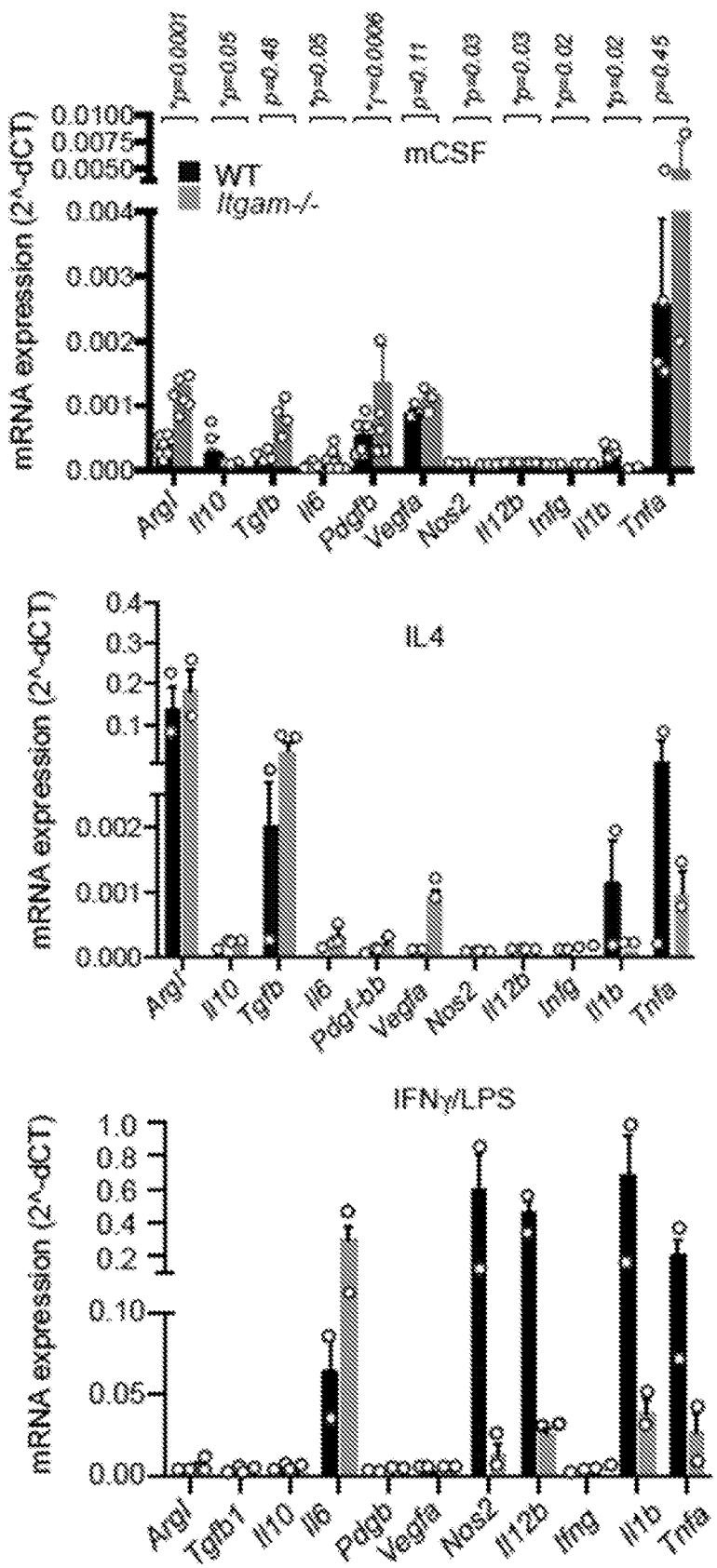

It was previously reported that the VCAM receptor integrin α4β1 promotes myeloid cell recruitment from the bone marrow to the tumor microenvironment, thereby promoting immune suppression, angiogenesis and tumor progression[2,13-15]. In contrast to its role in regulating recruitment of myeloid cells to tissues during acute inflammation[16-18], it was found that CD11b ($\alpha M\beta 2$), a myeloid cell integrin receptor for ICAM-1 and fibrinogen, does not affect myeloid cell recruitment to tumors, as global deletion of CD11b in Itgam-/- mice has no effect on the number of myeloid cells in circulation or in the number of cells recruited to tumors (FIGS. 6 and 7A-7D). Surprisingly, however, it was found that integrin CD11b plays an essential role in regulating macrophage polarization. Itgam-/- macrophages exhibited enhanced immune suppressive gene and protein expression and strongly reduced pro-inflammatory gene and protein expression compared with WT macrophages, whether stimulated under basal, IL-4 or IFNγ/LPS stimulation conditions (FIGS. 1A and 7E-7F).

Figure 1B:
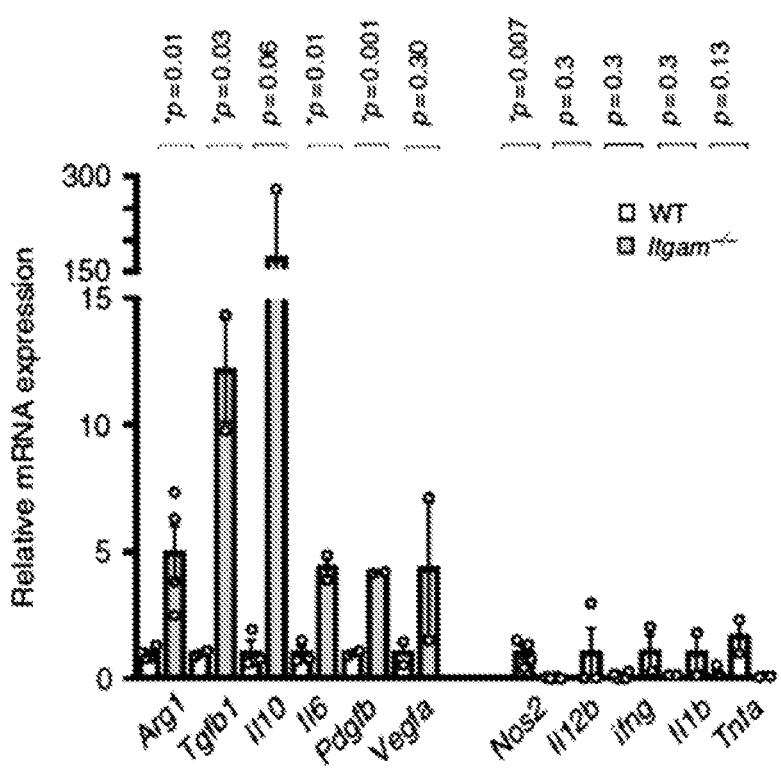
Figure 7G:
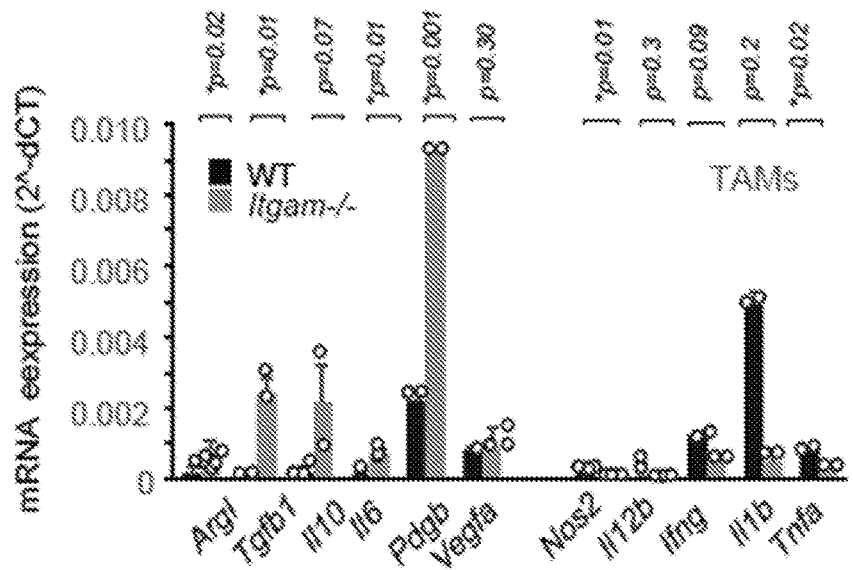
Figure 7H:
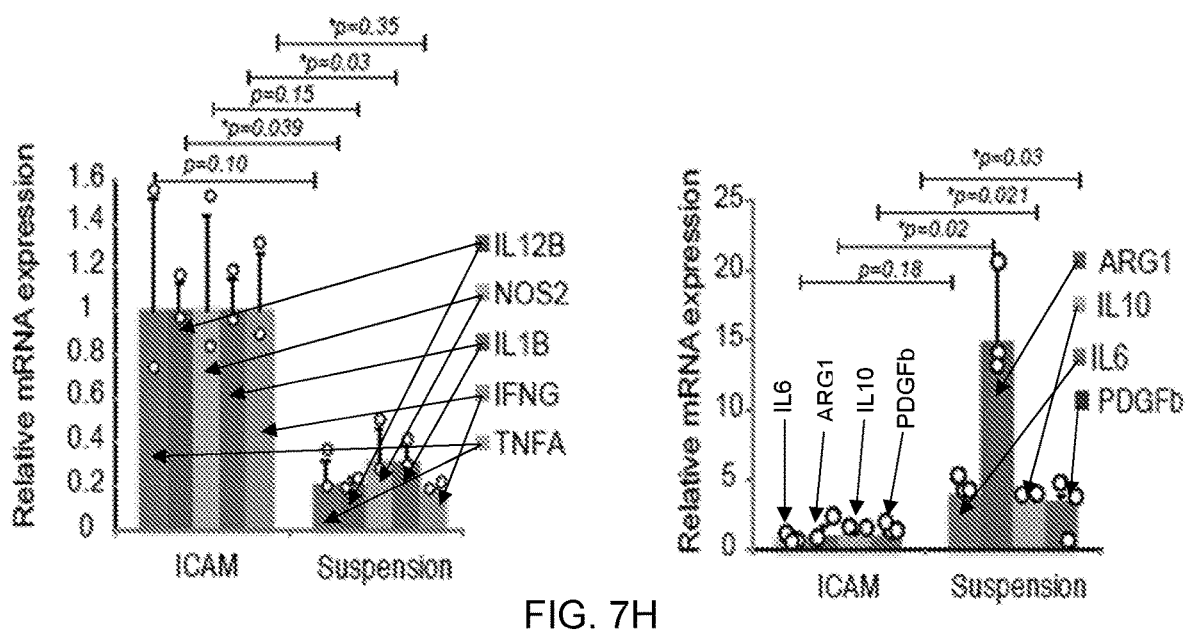

To determine whether CD11b also regulates macrophage polarization in vivo, F4/80+ TAMs from LLC tumors grown in Itgam-/- and WT mice were isolated and characterized. It was found that Itgam-/- TAMs expressed significantly higher levels of mRNAs associated with immune suppression and angiogenesis, such as Arg1, Tgfb, 1110, 116 and Pdgfb, and significantly lower expression of genes associated with immune stimulation, such as Ifng, Nos2, and Tnfa than did WT TAMs (FIGS. 1B and 7G).

Figure 1C:
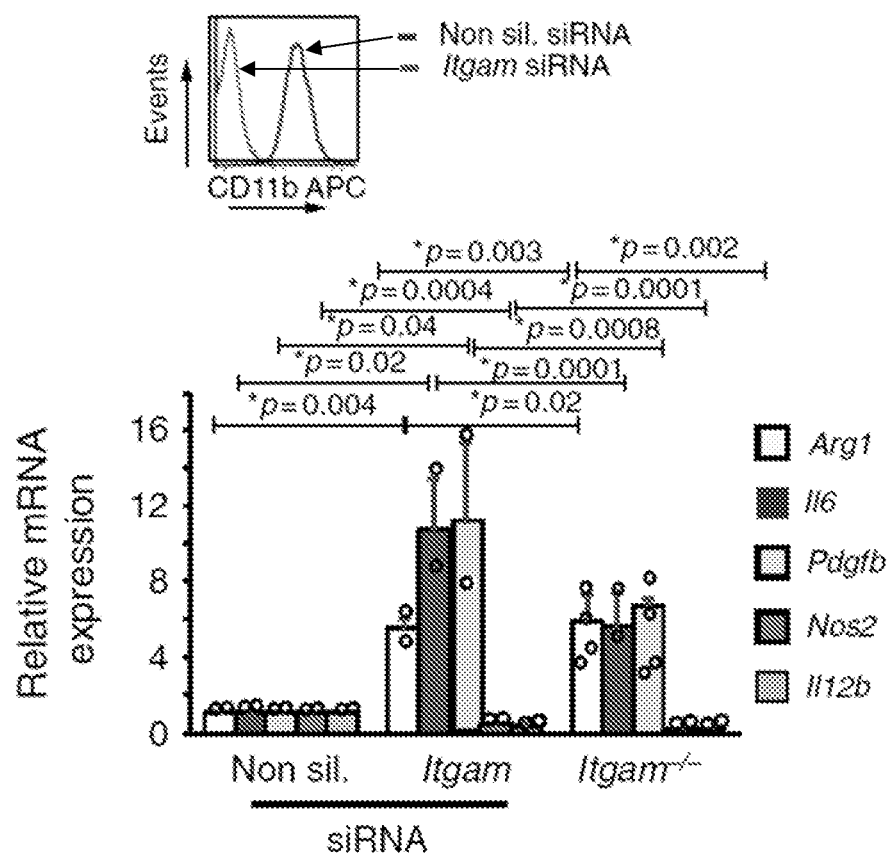
Figure 1D:
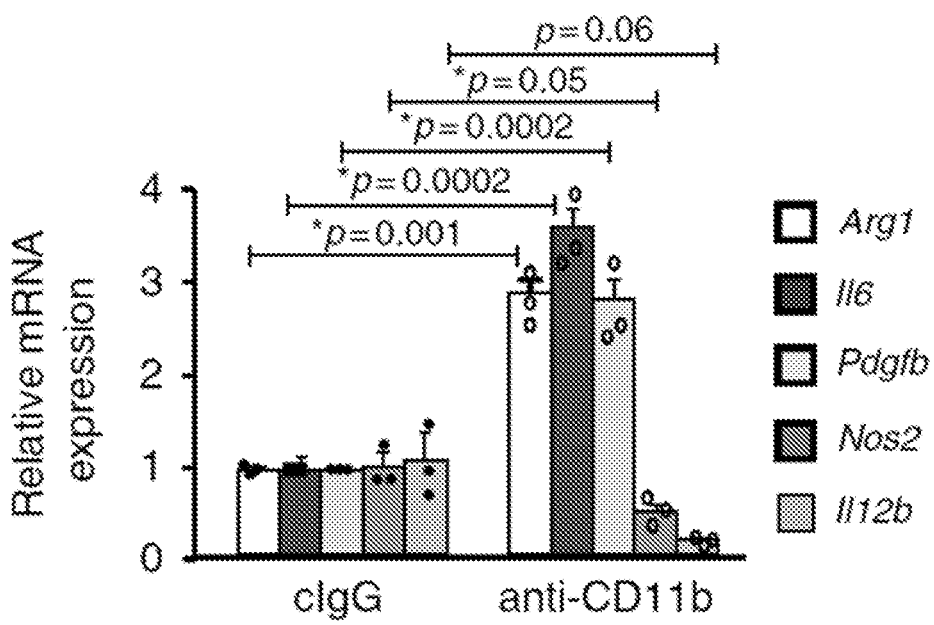
Figure 1E:
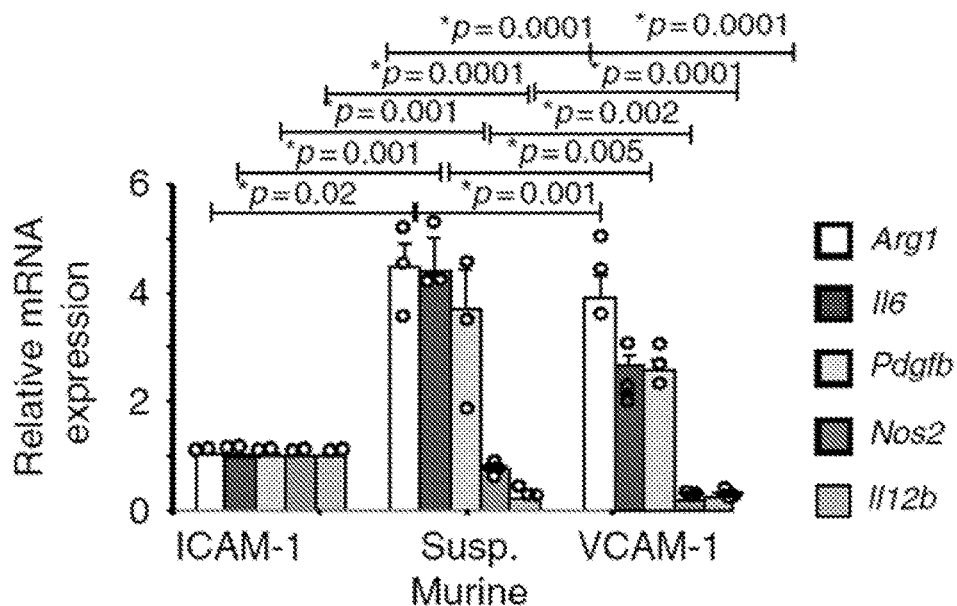
Figure 1F:
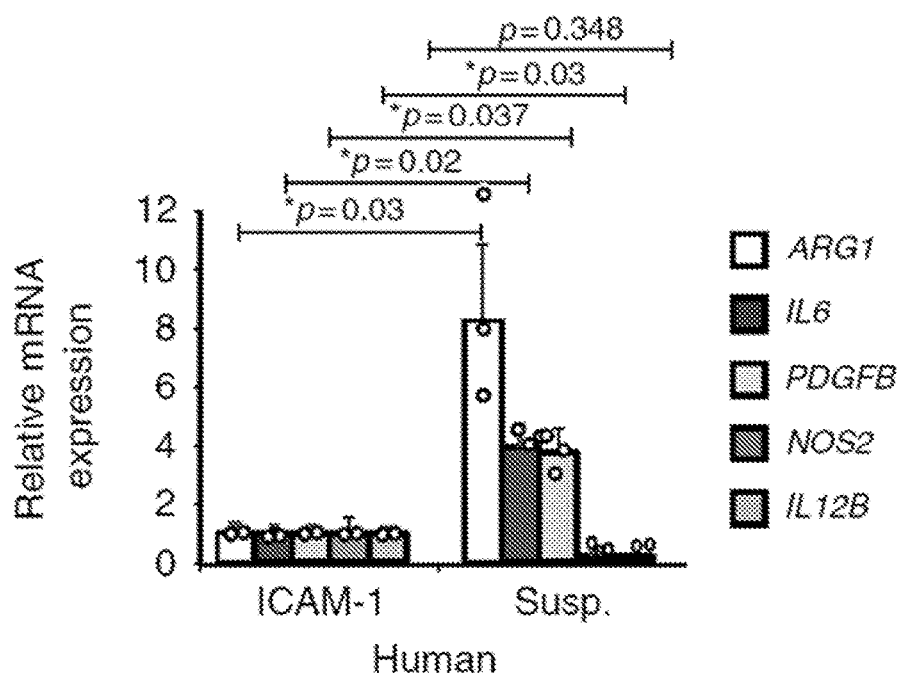

Transient siRNA-mediated knockdown of CD11b in in vitro cultured macrophages elevated immune suppressive gene expression and decreased immune stimulatory gene expression, effects that are comparable to CD11b deletion (FIG. 1C), indicating that even transient loss of CD11b controls macrophage immune suppressive gene expression. To address whether CD11b expression or function controls macrophage gene expression, the effect of inhibitory CD11b antibodies on macrophage mRNA expression was examined. Blockade of murine macrophage CD11b mediated attachment to ICAM-1-coated substrates by anti-CD11b neutralizing antibodies also induced immune suppressive mRNA expression in macrophages (FIG. 1D). Similarly, adhesion of macrophages to the integrin $\alpha 4\beta 1$ substrate VCAM-1 or loss of attachment by suspension culture promoted murine and human immune suppressive transcription, while attachment to ICAM-1 coated surfaces promoted immune stimulatory transcription (FIGS. 1E and 1F), indicating that ligation of CD11b controls immune stimulatory macrophage transcription.

Figure 1G:
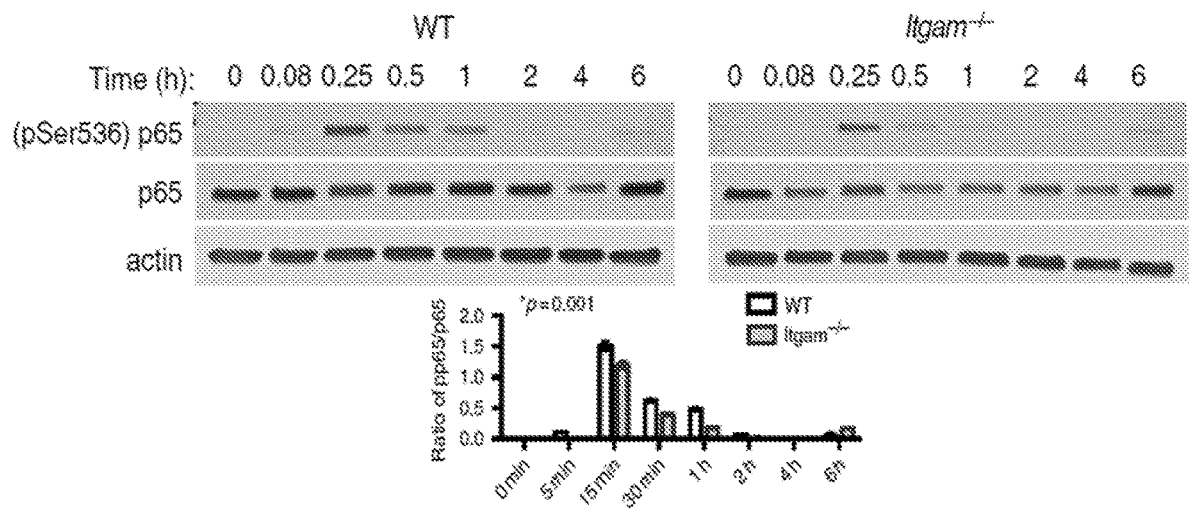

The loss of pro-inflammatory cytokine expression in Itgam-/- macrophages suggested that CD11b may regulate activation of pro-inflammatory transcription factors, such as NFκB. It was found that Itgam-/- macrophages exhibited reduced NFκB serine 536 phosphorylation (an indication of reduced activation[19]) in response to LPS stimulation compared to WT macrophages, suggesting CD11b plays a role in NFκB activation (FIG. 1G). As other studies have implicated CD11b in the promotion of pro-inflammatory responses of monocytes and dendritic cells through direct interactions of LPS with integrin beta2 extracellular domains[20,21], the results provided herein indicate that CD11b activation and signaling play key roles in the regulation of macrophage polarization in vitro and in vivo.

Figure 1H:
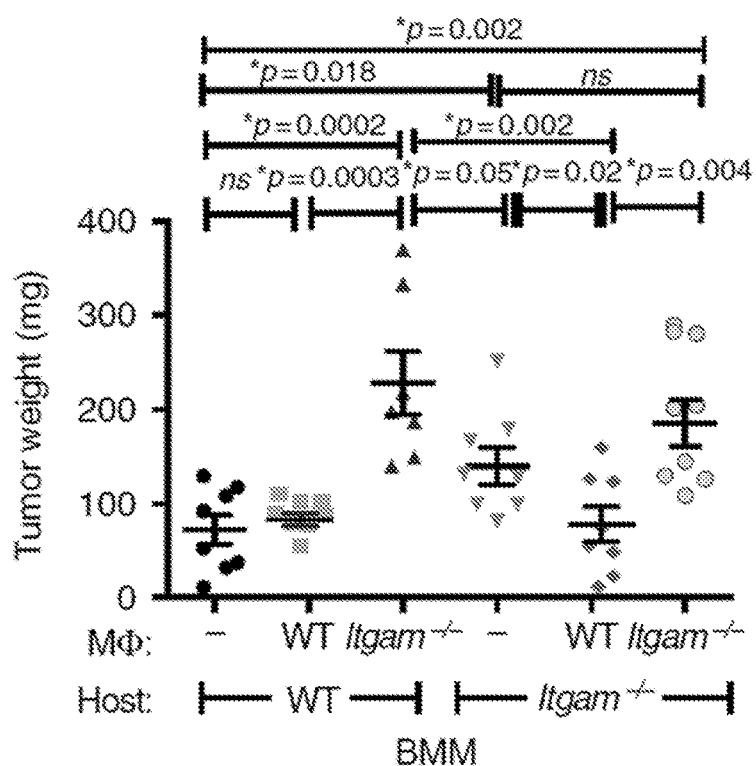
Figure 1I:
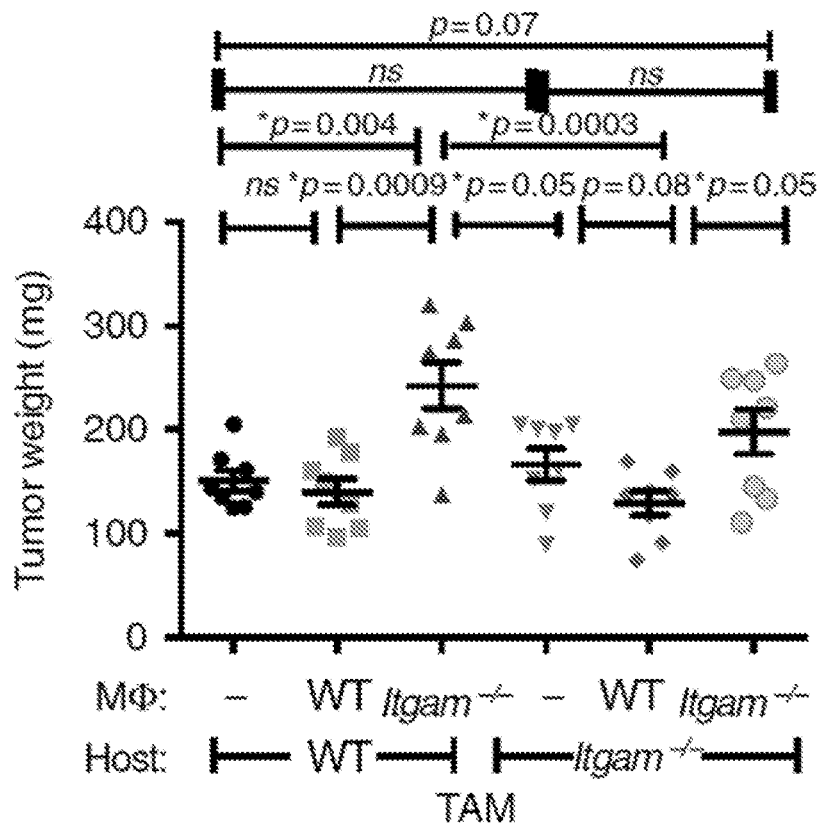
Figure 1J:
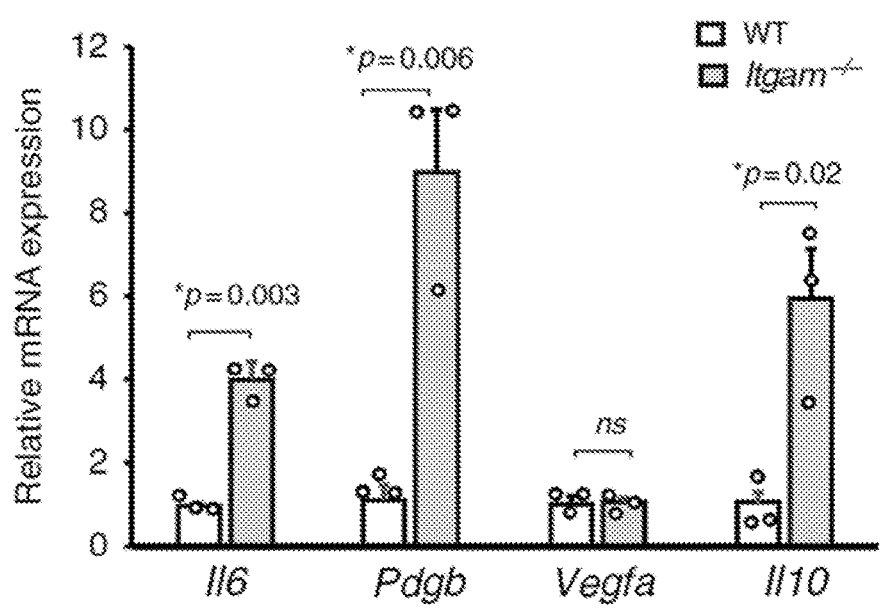

Itgam-/- bone marrow-derived and tumor associate macrophages exhibit more immune suppressive transcriptional profiles than WT macrophages. To determine if this difference affects tumor growth, WT or Itgam-/- bone marrow derived or tumor associated macrophages with tumor cells were adoptively transferred into recipient WT or Itgam-/- mice. It has been previously demonstrated that adoptively transferred, immune suppressive BMDM or TAMs can stimulate tumor growth[9,10]. Remarkably, bone marrow-derived Itgam-/- macrophages (FIG. 1H) as well as tumor-derived Itgam-/- macrophages (FIG. 1I) potently stimulated tumor growth compared with WT macrophages in both WT and Itgam-/- mice. As Itgam-/- macrophages exhibit an immune suppressive transcriptional profile (FIG. 1B), and tumors derived from Itgam-/- mice exhibit an overall immune suppressive transcriptional profile (FIG. 1J), these data suggested that CD11b expression or activation might impact overall tumor growth.

Figure 1K:
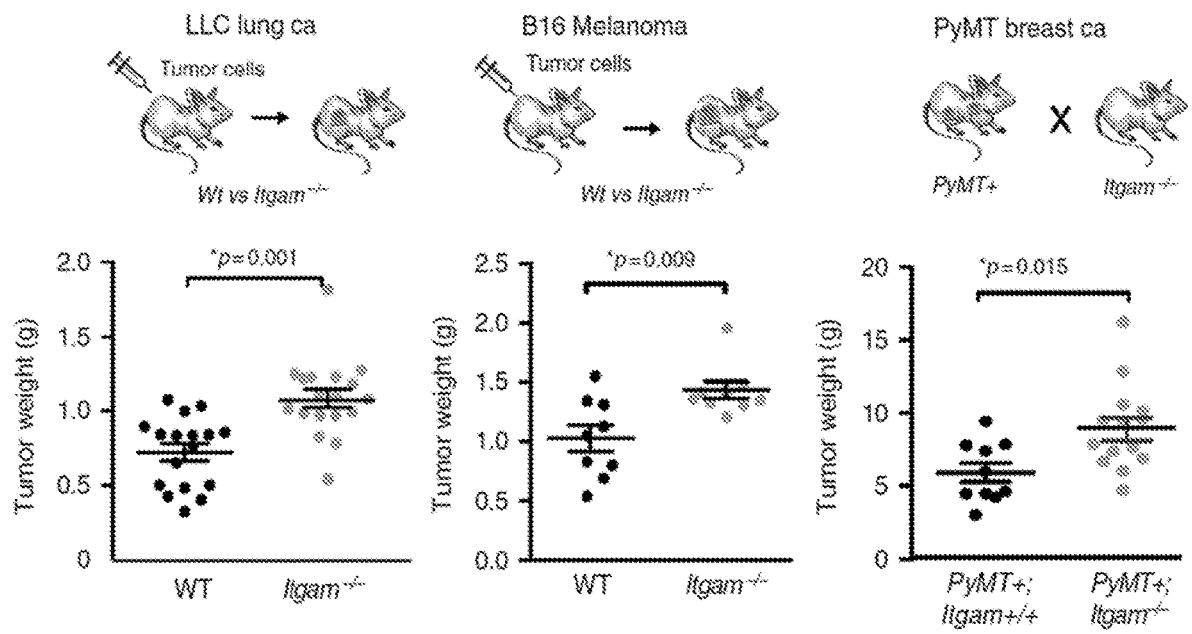
Figure 1L:
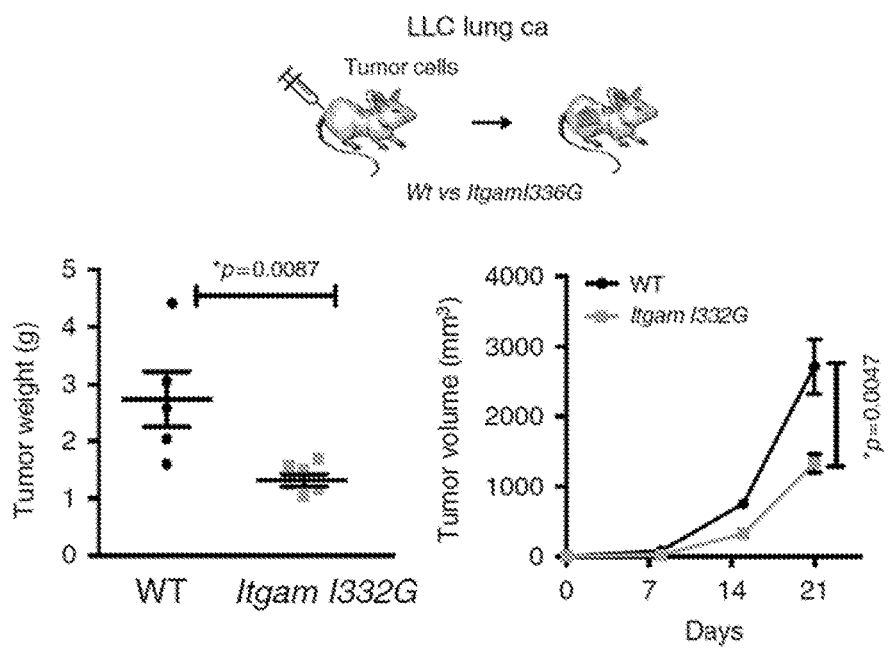
Figure 8A:
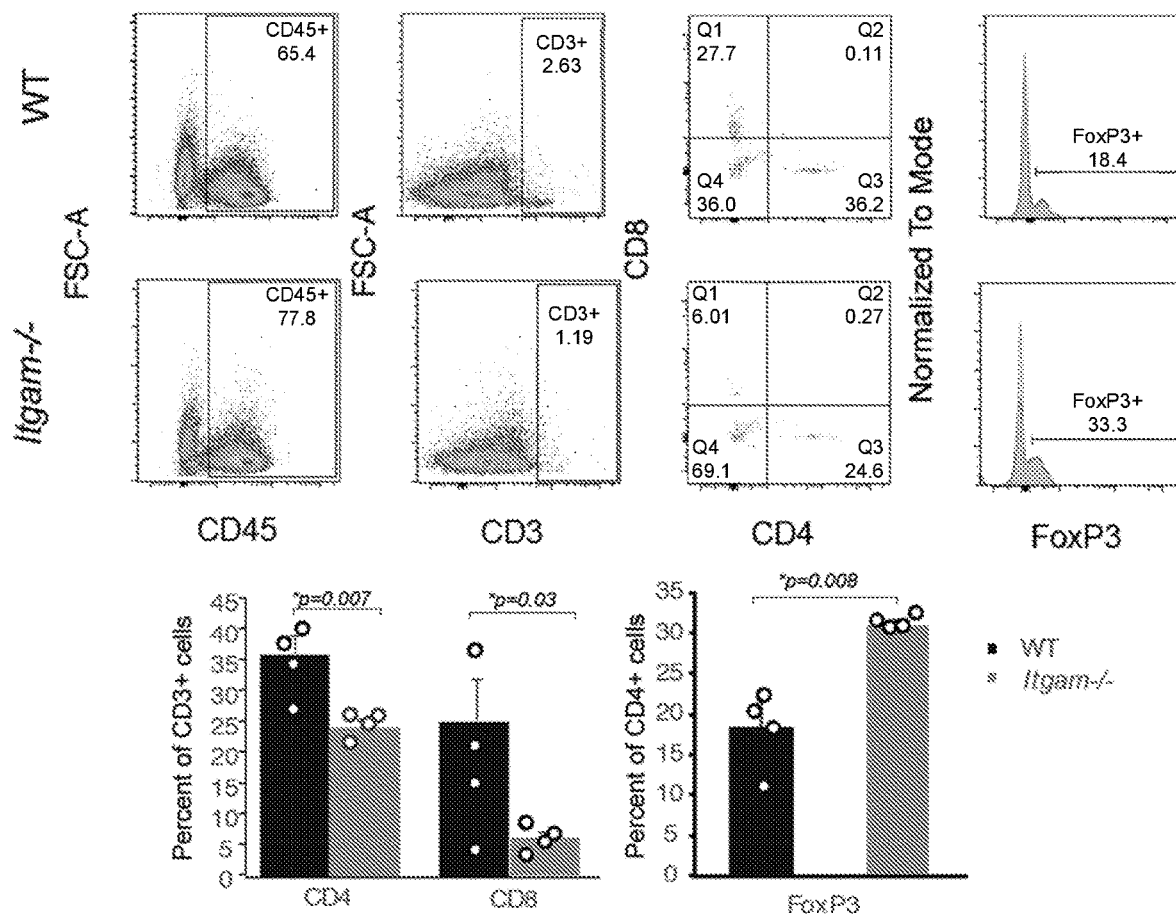
FIGS. 8A-8E are pictorial and graphical diagrams showing that tumor derived cytokines suppress CD11b expression and promote immune suppressive macrophage phenotype.
Figure 8B:
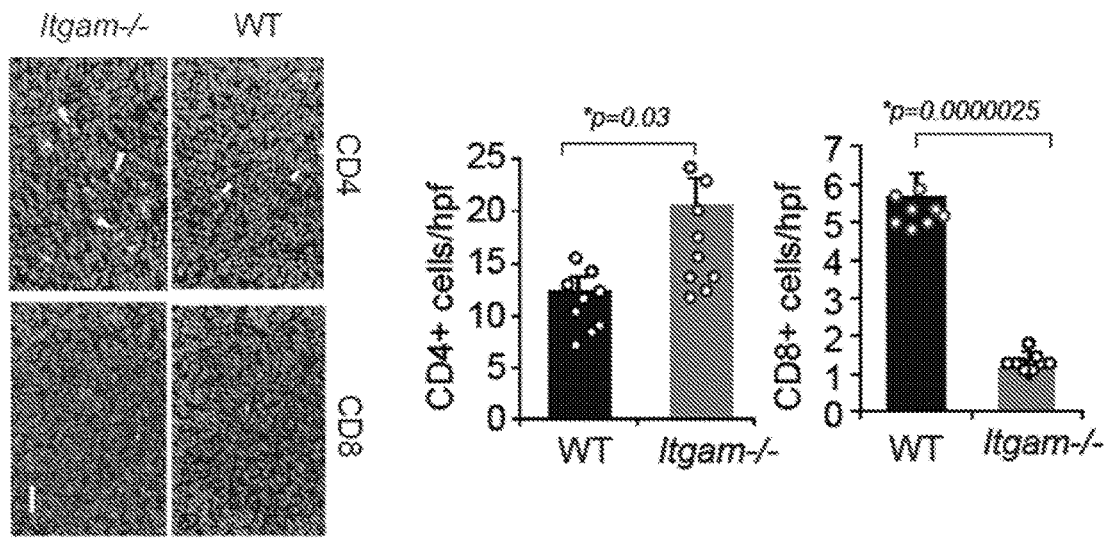

Indeed, it was found that subcutaneous (LLC), orthotopic (melanoma) and autochthonous (PyMT) tumors grew more aggressively in Itgam-/- than in WT mice (FIG. 1K). As Itgam-/- mice exhibited substantially more CD4+Foxp3+ $T_{regs}$ and fewer CD8+ T cells in tumors than WT mice (FIGS. 8A-8B), the present data support the conclusion that CD11b plays a key role in regulating the overall immune response in tumors.

Figure 8C:
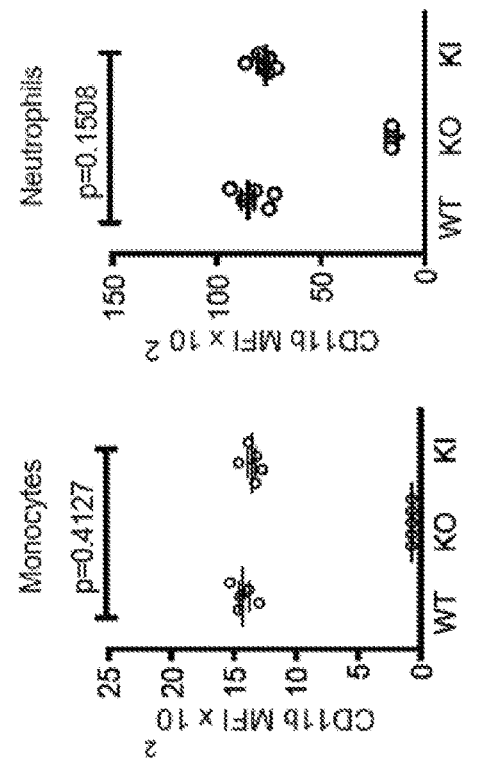
Figure 8D:
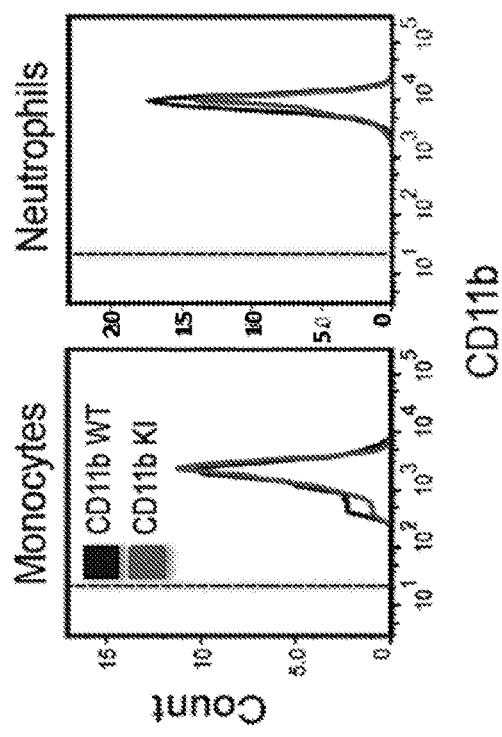
Figure 8E:
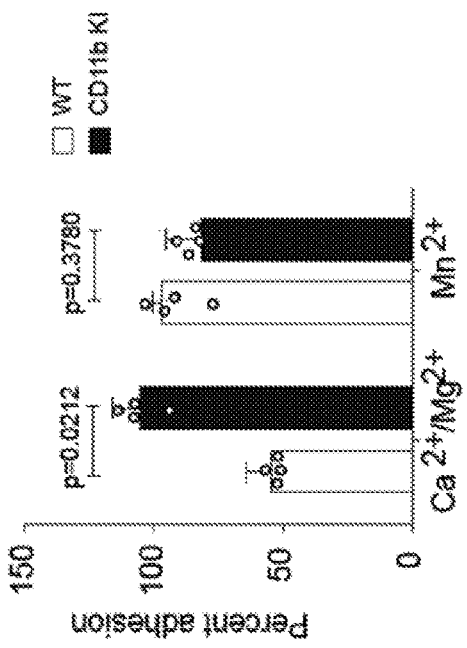
Figure 8E:
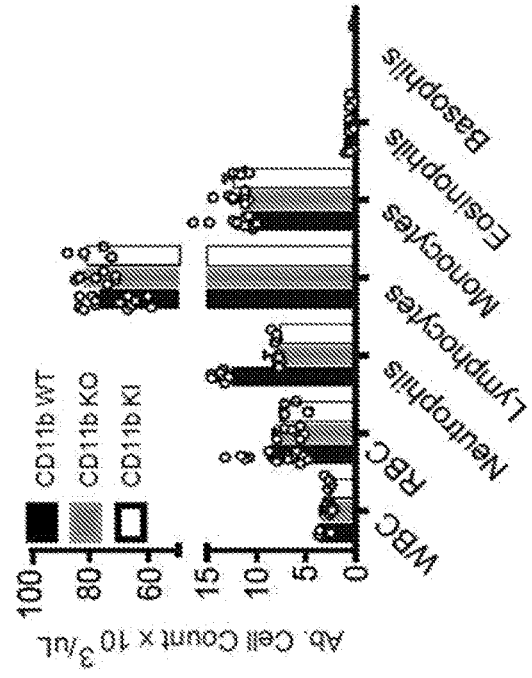

Prior studies have shown that Isoleucine 332 in the CD11b molecule serves as an allosteric switch controlling the adhesion receptor's activation and shape[22]. To determine whether CD11b activation controls tumor development, a constitutively activated CD11b knockin mouse strain (C57BL/6 ITGA-M$^{I332G}$) was generated by introducing an I332G point mutation in the murine Itgam gene. I332G knockin mice express normal levels of cell surface CD11b on both monocytes and granulocytes and exhibit normal levels of all blood cell level (FIGS. 8C-8D). In vitro adhesion assays with bone marrow derived macrophages from these mice showed that I332G cells express constitutively active CD11b (FIG. 8E). Importantly, I332G Itgam knockin mice exhibited significantly reduced LLC tumor growth (FIG. 1K). Thus, while CD11b deletion stimulates anti-inflammatory macrophage polarization, inhibits CD8+ T cell recruitment and promotes tumor growth, CD11b activation potently inhibits tumor growth. These studies indicate that macrophage CD11b plays a critical functional role in controlling tumor growth.

Figure 9A:
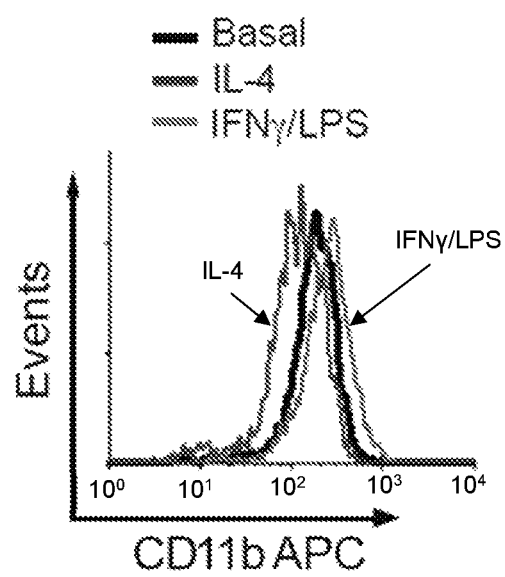
FIGS. 9A-9G show tumor derived cytokines suppress CD11b expression and promote immune suppressive macrophage phenotype.
Figure 9B:
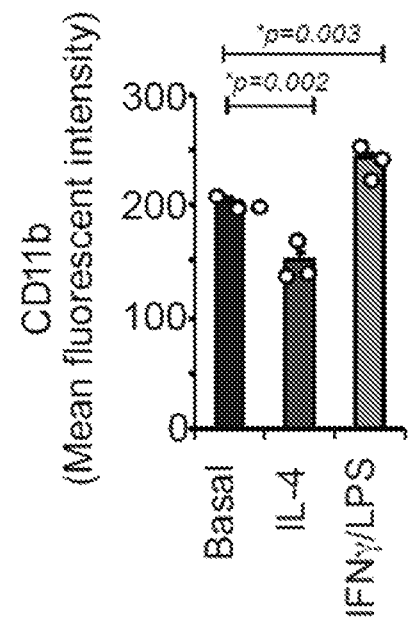
Figure 9C:
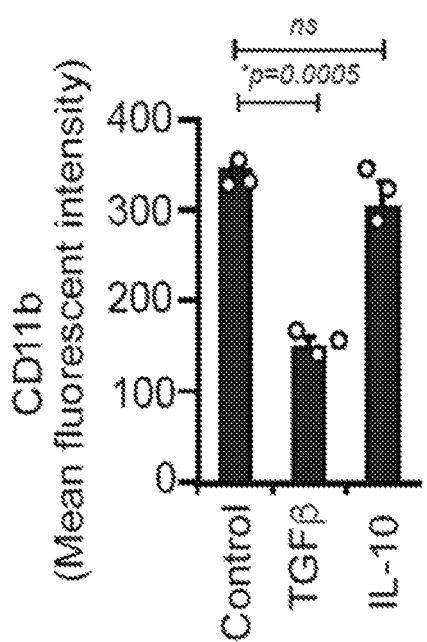
Figure 9D:
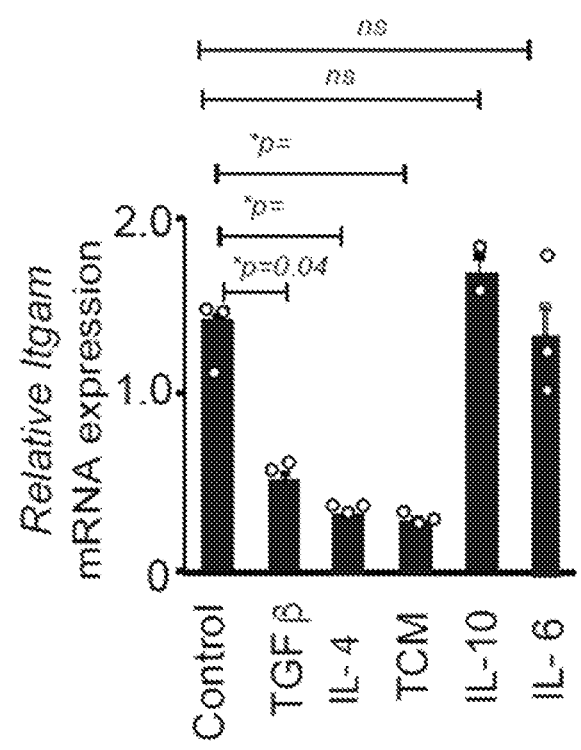
Figure 9E:
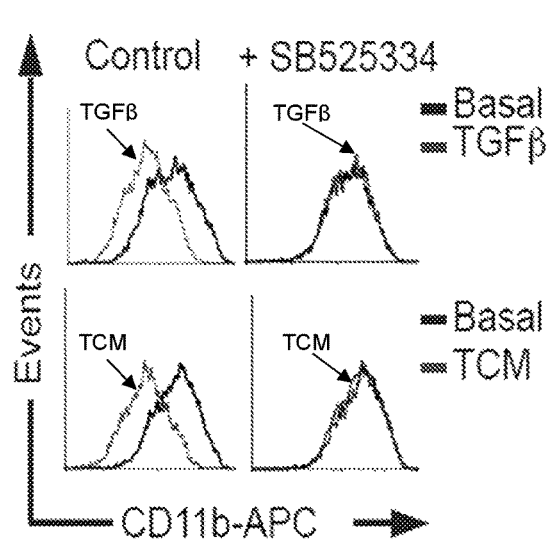
Figure 9F:
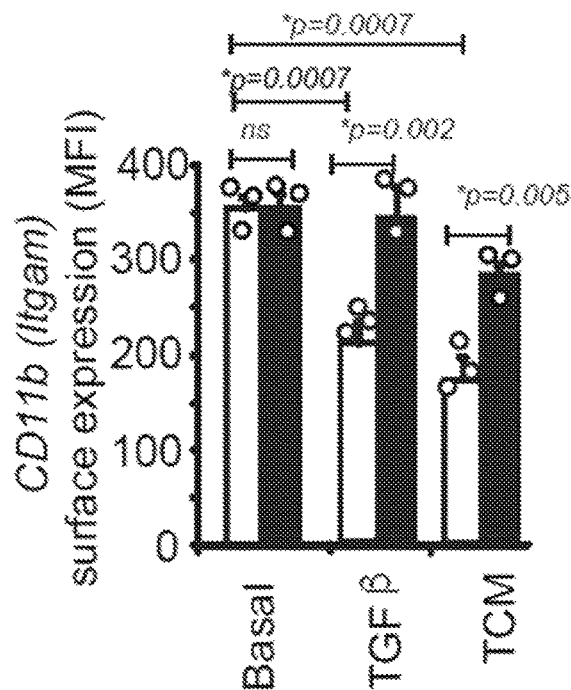
Figure 9G:
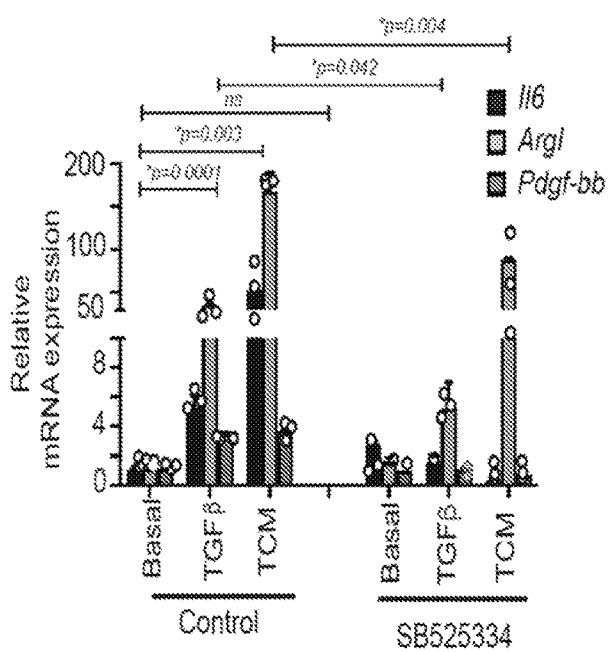
Figure 9G:
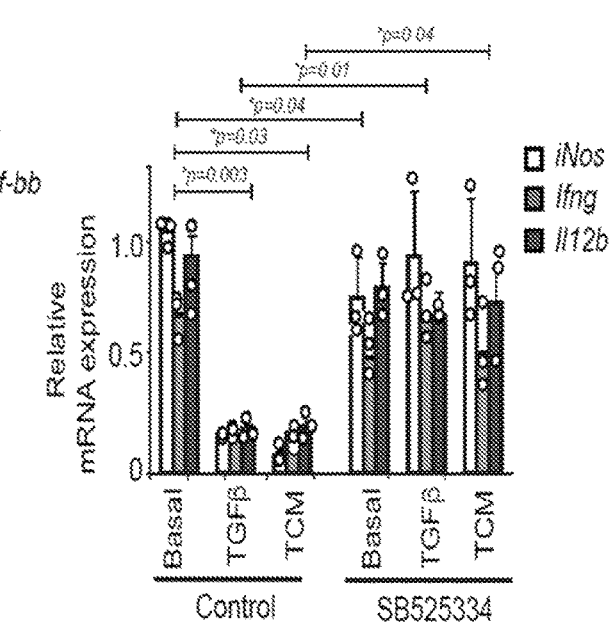

To determine whether signals associated with the tumor microenvironment can alter CD11b expression and subsequently affect myeloid cell polarization, the effect of macrophage media (mCSF-, IL-4- and IFNγ/LPS) on cell surface CD11b expression in bone marrow derived macrophages was evaluated. While the immune suppressive cytokine IL-4 reduced CD11b expression, the pro-inflammatory stimuli IFNγ/LPS enhanced CD11b surface expression compared to levels expressed on mCSF-stimulated macrophages (FIGS. 9A-9B). Additionally, the immune suppressive factor TGFβ, but not IL-10, inhibited CD11b surface expression (FIG. 9C); TGFβ, IL-4 and tumor cell conditioned medium (TCM) each also suppressed Cd11b mRNA expression (FIG. 9D). Importantly, TGFβ and TCM reduced CD11b cell surface expression and stimulated immune suppressive transcription while inhibiting immune stimulatory transcription in a manner that was reversed by the TGFβR1 inhibitor SB525334 (FIGS. 9E-9G). These data indicate that cytokines such as TGFβ in the tumor microenvironment suppress CD11b expression or activation, thereby promoting immune suppressive macrophage polarization.

Figure 2A:
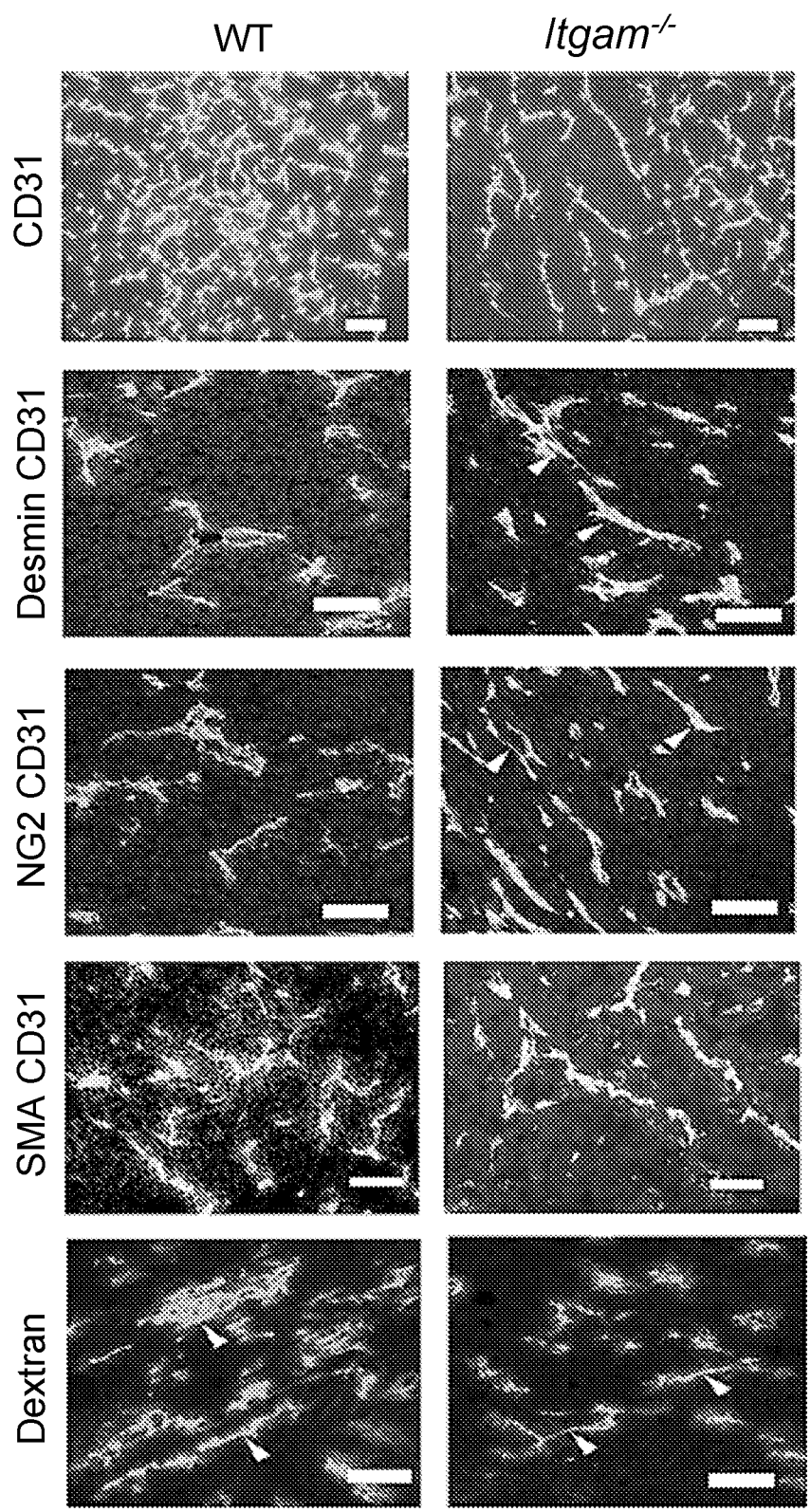
Figure 2F:
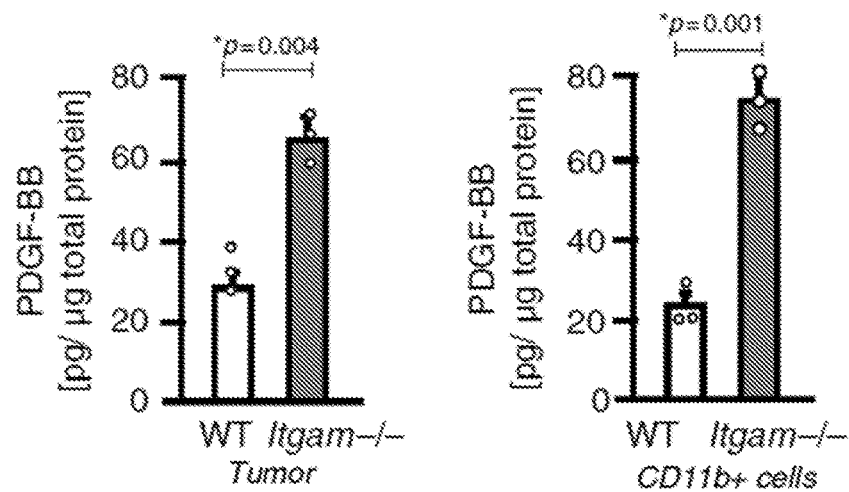
Figure 10A:
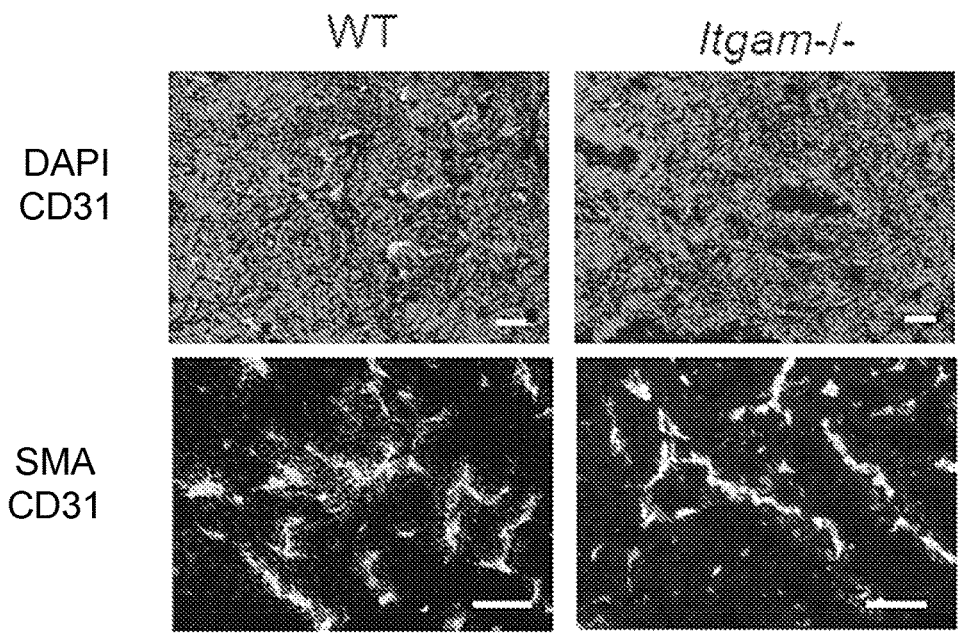
FIGS. 10A-10C show that CD11b loss promotes vascular normalization.
Figure 10B:
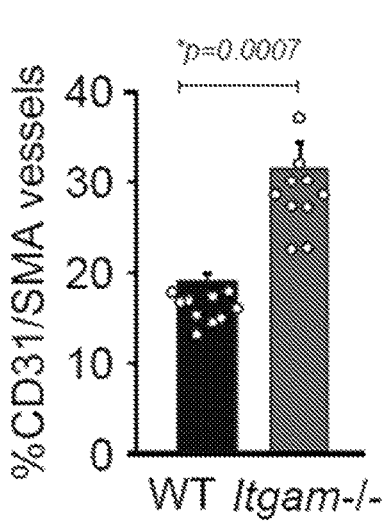

Macrophages not only control immune responses, but also induce angiogenesis and desmoplasia by expressing cytokines such as VEGF-A and PDGF-BB, growth factors that regulate endothelial cell and vascular smooth muscles/pericytes during angiogenesis, respectively[2]. Tumor blood vessels often consist of a single endothelial layer that lacks supporting pericytes or smooth muscle cells; these blood vessels are more numerous in tumors than in normal tissues but are aberrantly formed and poorly perfuse. In contrast, in tumors with high PDGF to VEGF ratios, blood vessels are lined by pericytes, mesenchymal cells that stabilize vessels and promote better tumor perfusion[23-27]. These tumors grow more rapidly than tumors with lower PDGF to VEGF ratios but also respond better to chemotherapy and immune therapy due to better tumor perfusion[24-36]. As Itgam−/− macrophages exhibited high PDGF and low VEGF gene expression (FIGS. 1A and 1B), the patterns of blood vessel development in Itgam−/− and WT tumors were examined. An assessment of vascular patterning in LLC and PyMT tumors from WT and Itgam−/− mice showed that Itgam−/− tumors exhibited fewer, longer blood vessels with wider lumens and fewer branch points/field than WT tumors (FIGS. 2A, 2B and 10A). Itgam−/− tumors had more blood vessels that were lined with Desmin+, NG2+, or SMA+ pericytes/smooth muscle cells than did WT tumors (FIGS. 2A-2C and 10B). Accordingly, these vessels were less permeable in Itgam−/− mice than in WT mice, as less intravascular FITC-dextran leaked into the tumor parenchyma (FIGS. 2A-2D). These data indicate that the integrin CD11b plays a role in controlling blood vessel maturation.

Figure 10C:
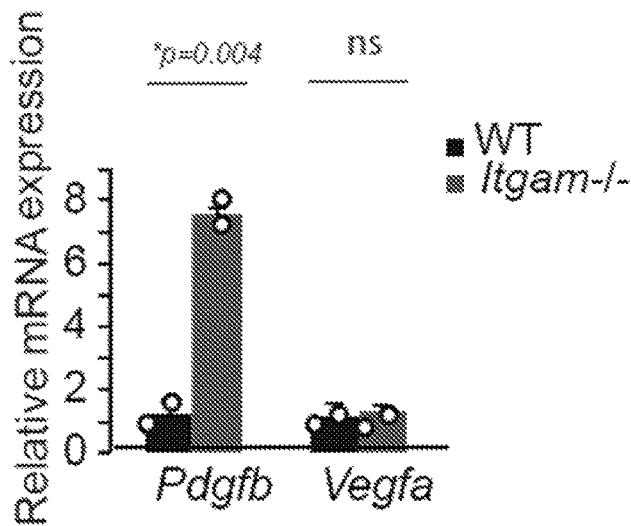

It was found that protein and gene expression of PDGF-BB, but not VEGF-A, was strongly enhanced in tumors (FIGS. 2E and 10C). Importantly, PDGF-BB protein expression was also elevated in Itgam−/− tumors and tumor-derived macrophages compared to WT tumors (FIG. 10F). Together, these data suggest that macrophage CD11b controls tumor vascularization through the constitutive expression of elevated levels of PDGF.

Figure 2G:
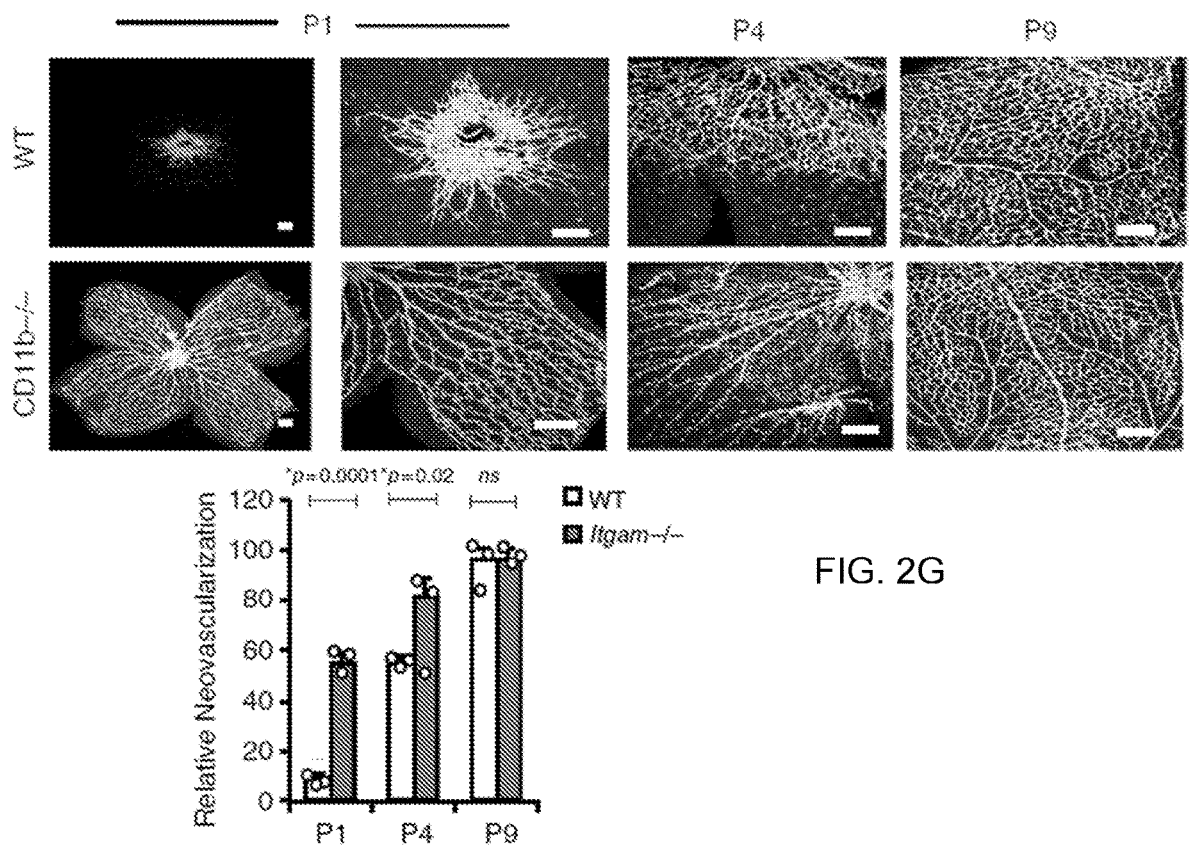

In support of these observations on CD11b roles in neovascularization, it was found that Itgam−/− mice exhibited a well-developed retinal vascular plexus (FIG. 2B; Isolectin B+) at birth (P1) in contrast to WT mice, which exhibit undeveloped retinal vasculature that expands progressively from postnatal day 1 (P1) to P9. The superficial vascular plexus was more developed in Itgam−/− mice than in WT neonates from postnatal day P1 through postnatal day P9 (FIG. 2G). These results indicate that CD11b also controls normal vascular patterning.

Figure 2H:
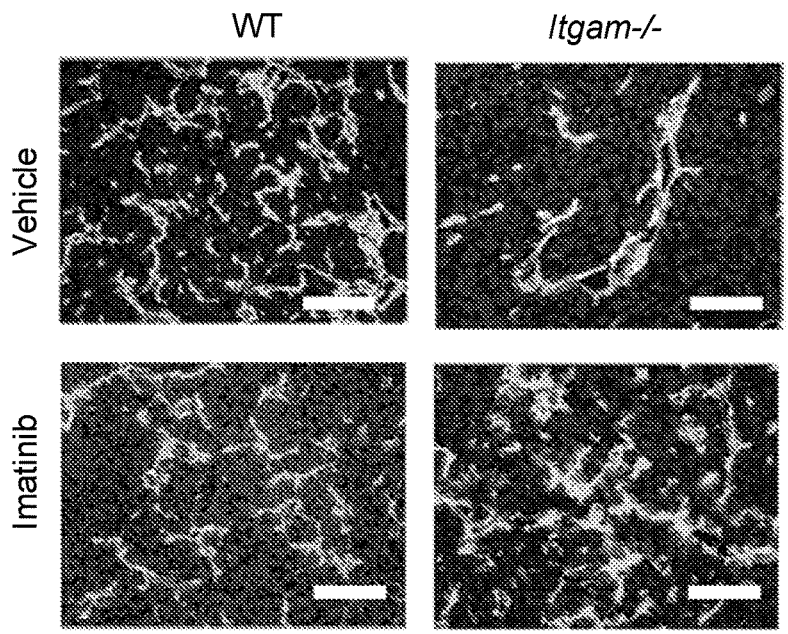
Figure 2I:
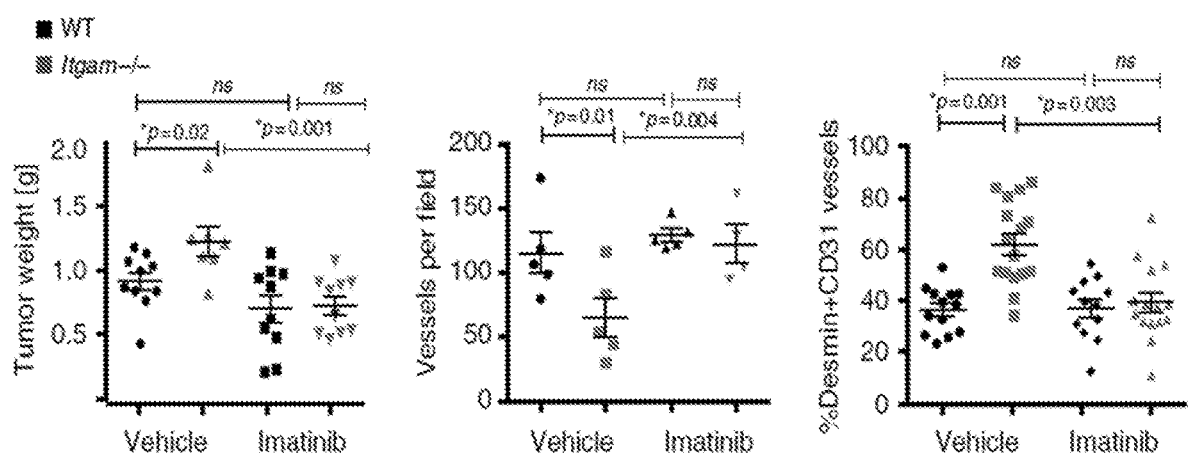

To investigate whether elevated PDGF-BB is responsible for the enhanced vascular maturation and tumor growth in Itgam−/− mice, WT and Itgam−/− mice bearing LLC tumors were treated with imatinib, an inhibitor of the PDGF-BB receptor PDGFR1. Imatinib treatment suppressed the enhanced tumor growth and increased vascular normalization observed in Itgam−/− mice (FIGS. 2H-2I). Together these results indicate that CD11b modulates vascular development through control of PDGF-BB expression.

Figure 3A:
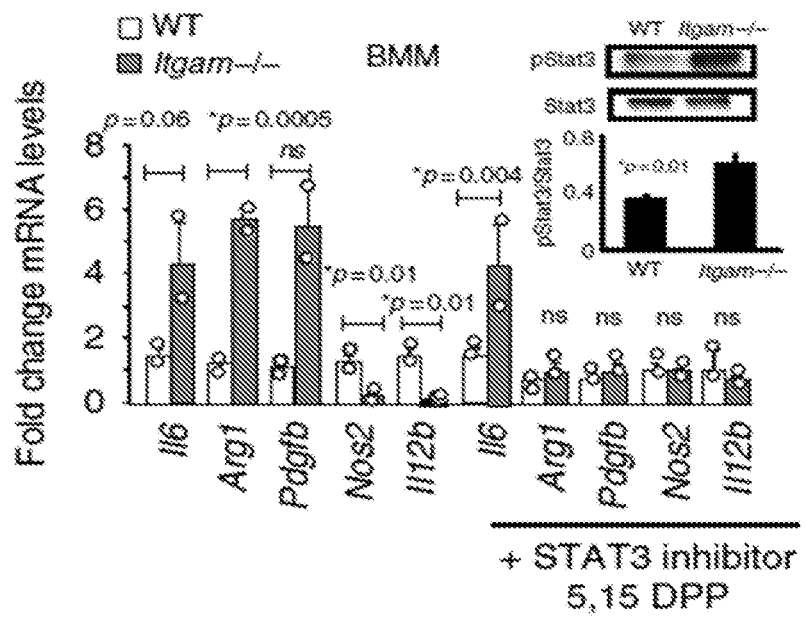
FIGS. 3A-3L are graphical and pictorial diagrams showing that CD11b promotes miR-Let7a mediated immune stimulation.

CD11b may control anti-inflammatory macrophage polarization through the activation of transcription factors such as Stat3, which can promote expression of immune suppressive and pro-angiogenic factors such as Arginase 1, Myc, and VEGF[37-39]. Itgam−/− macrophages exhibit constitutively phosphorylated Stat3 (FIG. 3A, inset); the high levels of immune suppressive factor expression in Itfam−/− macrophages were reduced to WT macrophage levels by treatment with the Stat3 inhibitor 5,15-DPP (FIG. 3A). Surprisingly, Stat3 inhibition did not affect the high levels of Il6 expression observed in Itgam−/− macrophages (FIG. 3A).

Figure 3B:
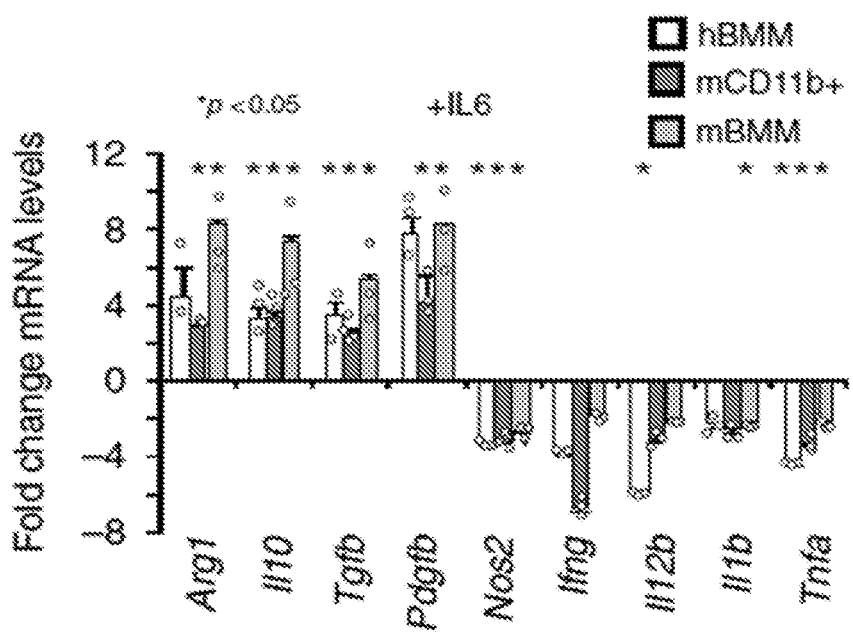
Figure 3C:
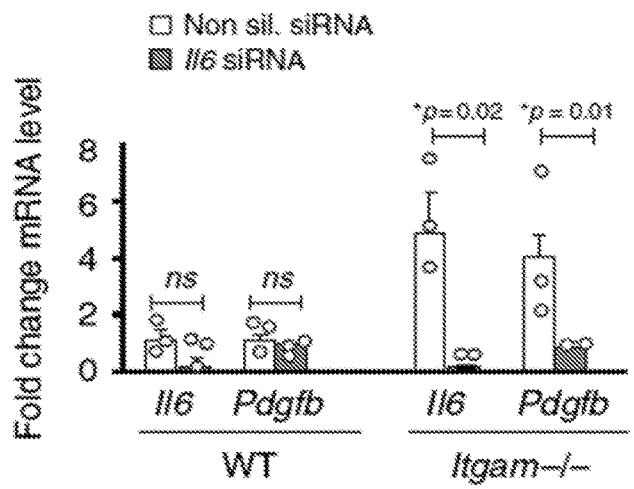

Importantly, IL-6 can directly activate Stat3[38]. It was found that IL-6 promoted the same pattern of immune suppressive polarization in murine and human myeloid cells and macrophages that was observed in Itgam−/− macrophages (FIG. 3B). Together, these results suggested that autocrine IL6 may drive the constitutively immune suppressive polarization observed in Itgam−/− macrophages. In support of this concept, Il6 knockdown decreased expression of constitutive Pdgfb expression in Itgam−/− macrophages (FIG. 3C). As TAMs are a major source of Il6 expression in tumors[15], these results suggest that CD11b serves as a natural brake on immune suppression in part through control of myeloid cell transcription of Il6.

Accordingly, the invention provides a method of treating cancer in a subject. The method includes administering to a subject in need thereof, a therapeutically effective amount of an agonist of CD11b expression, as described herein.

MicroRNAs (miRNAs) are non-coding RNAs that modulate gene expression at the posttranscriptional level by interfering with RNA translation or stability and can dramatically impact tumor immune suppression and angiogenesis[42,43]. The Let7 family of miRNAs has been shown to control Il6 expression in tumor and inflammatory cells[40,41].

Figure 3D:
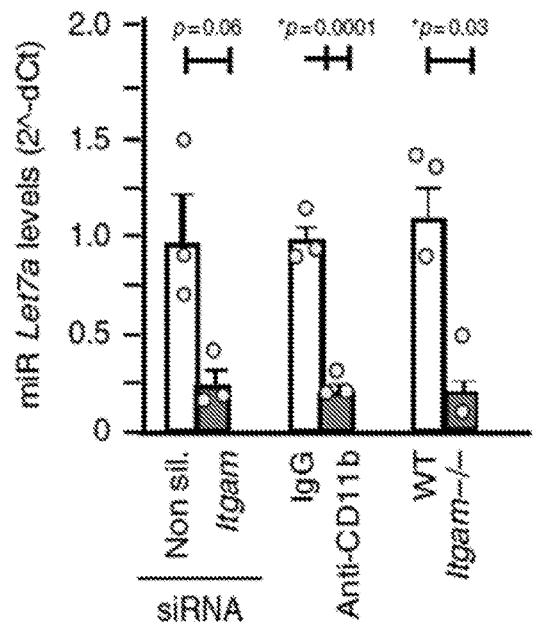
Figure 3E:
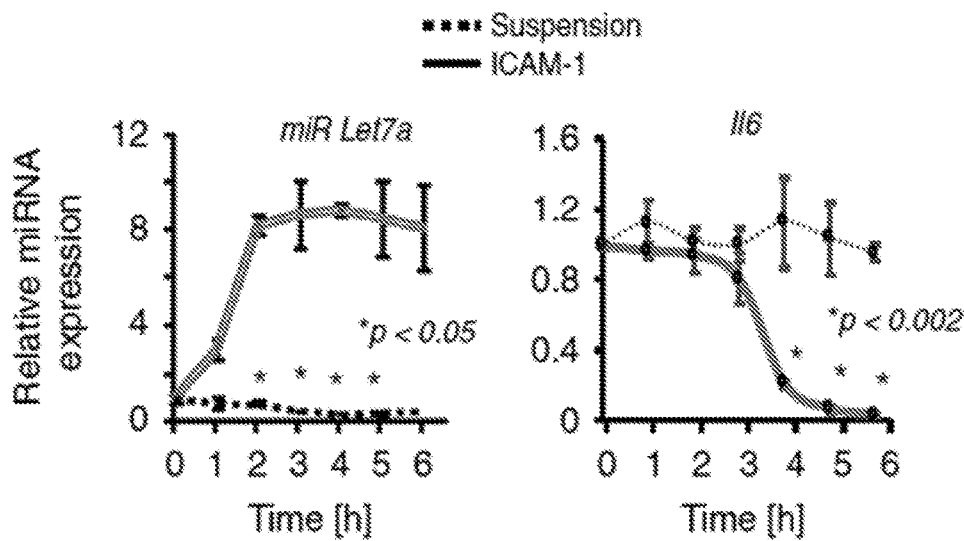
Figure 3F:
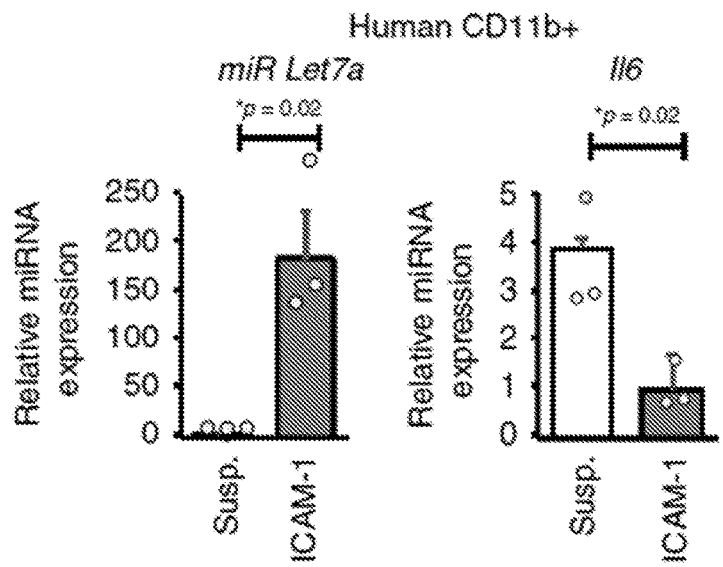
Figure 3G:
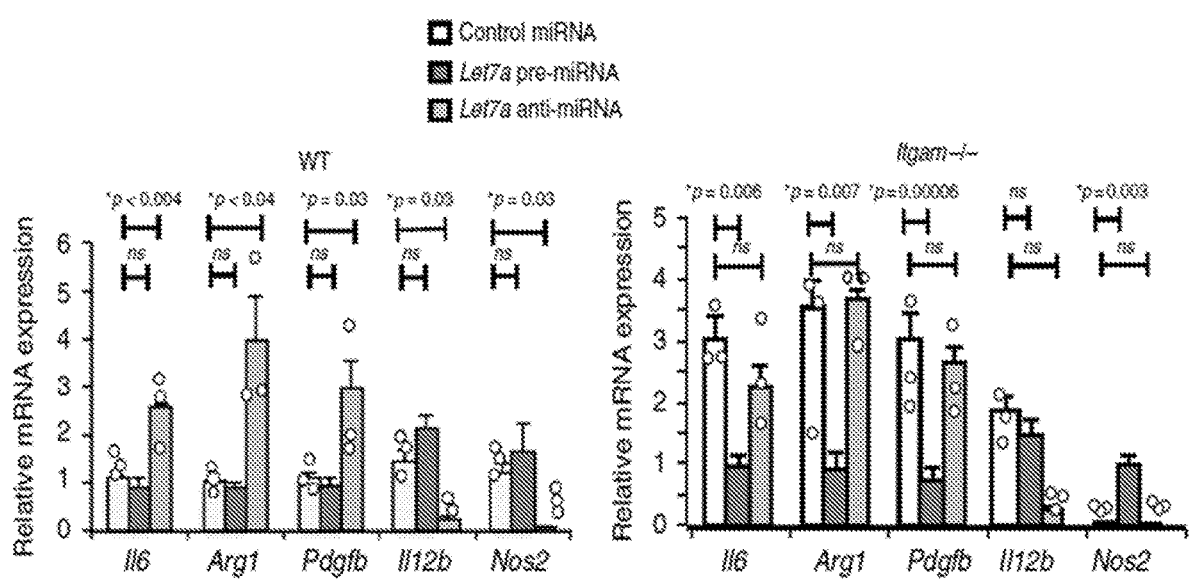
Figure 3H:
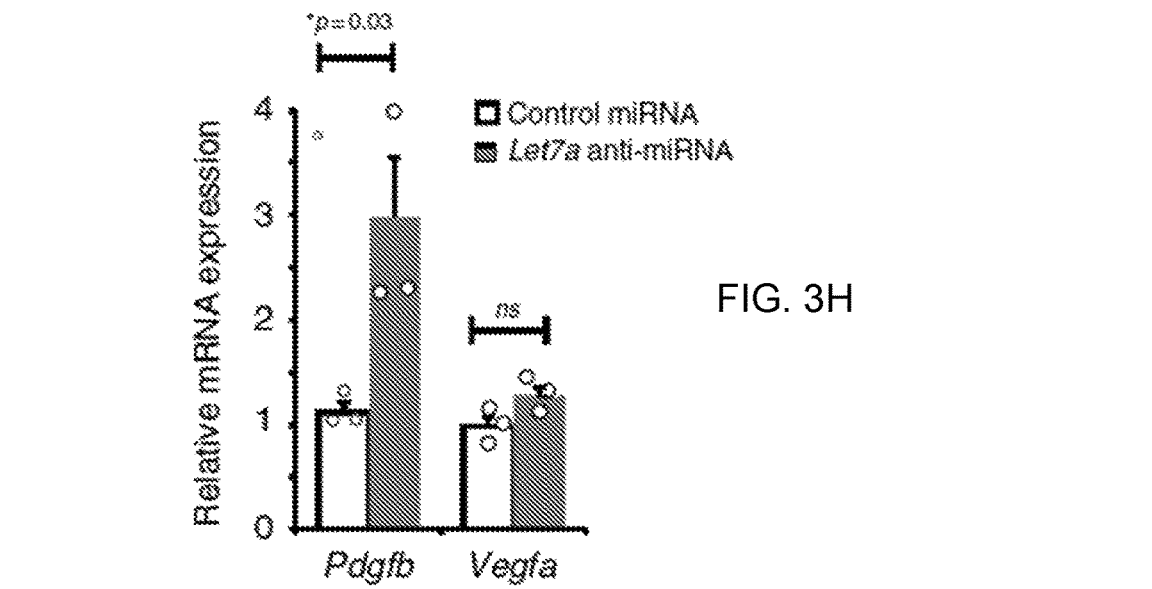
Figure 3I:
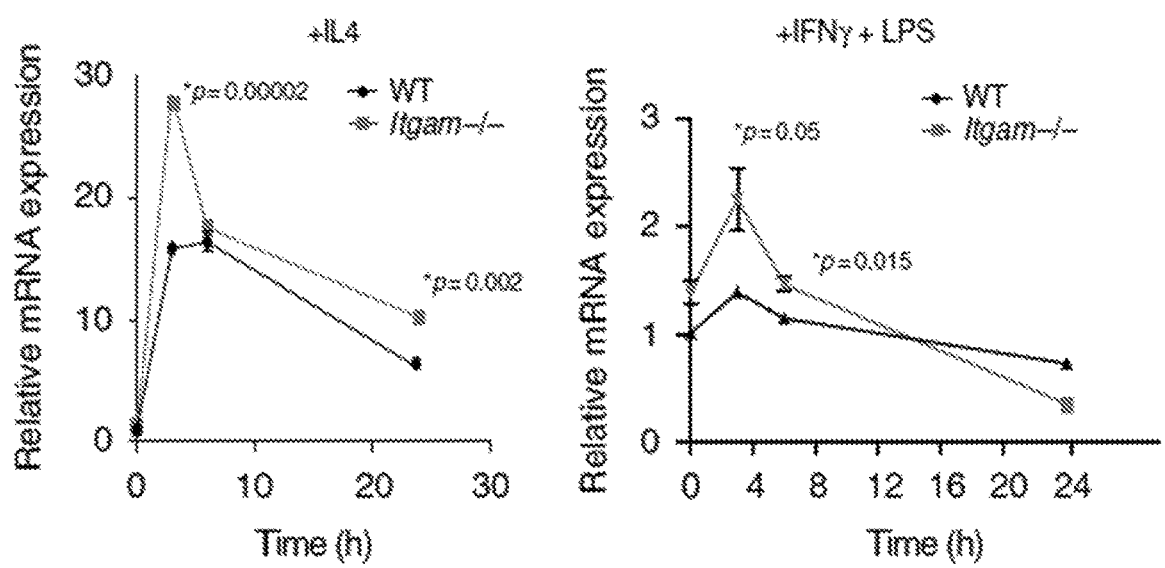
Figure 3J:
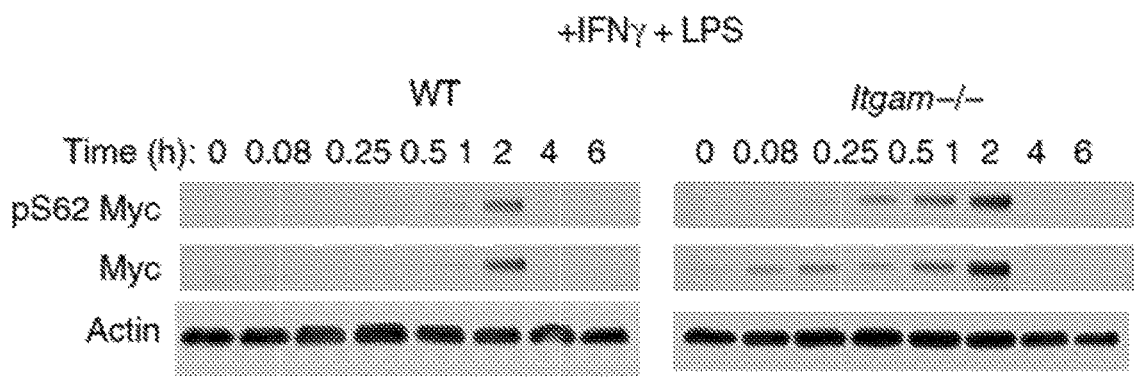
Figure 3K:
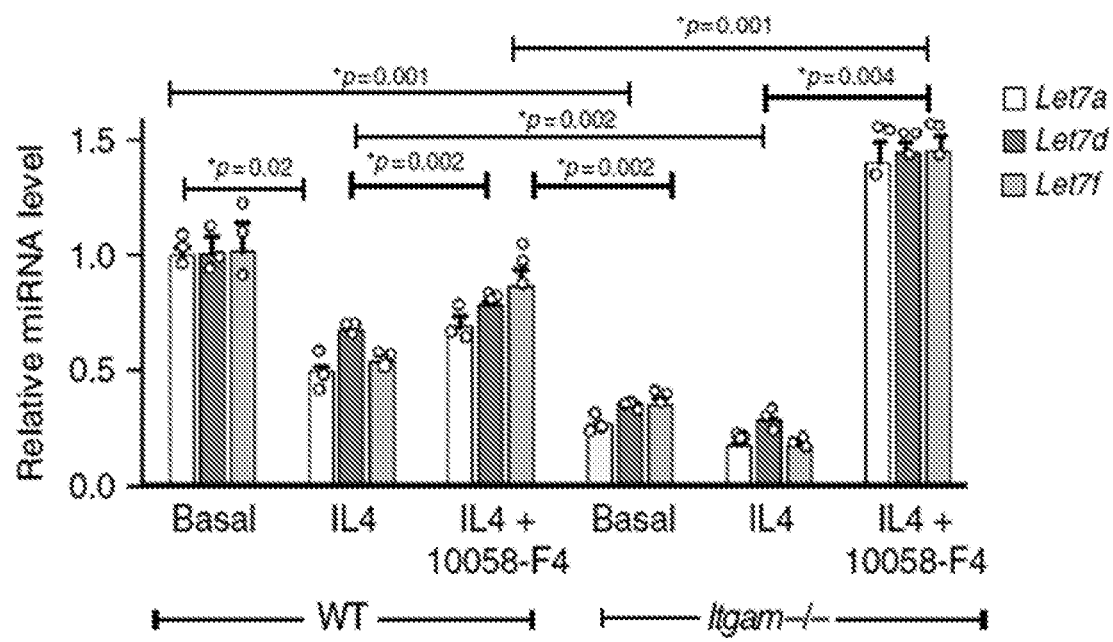
Figure 3L:
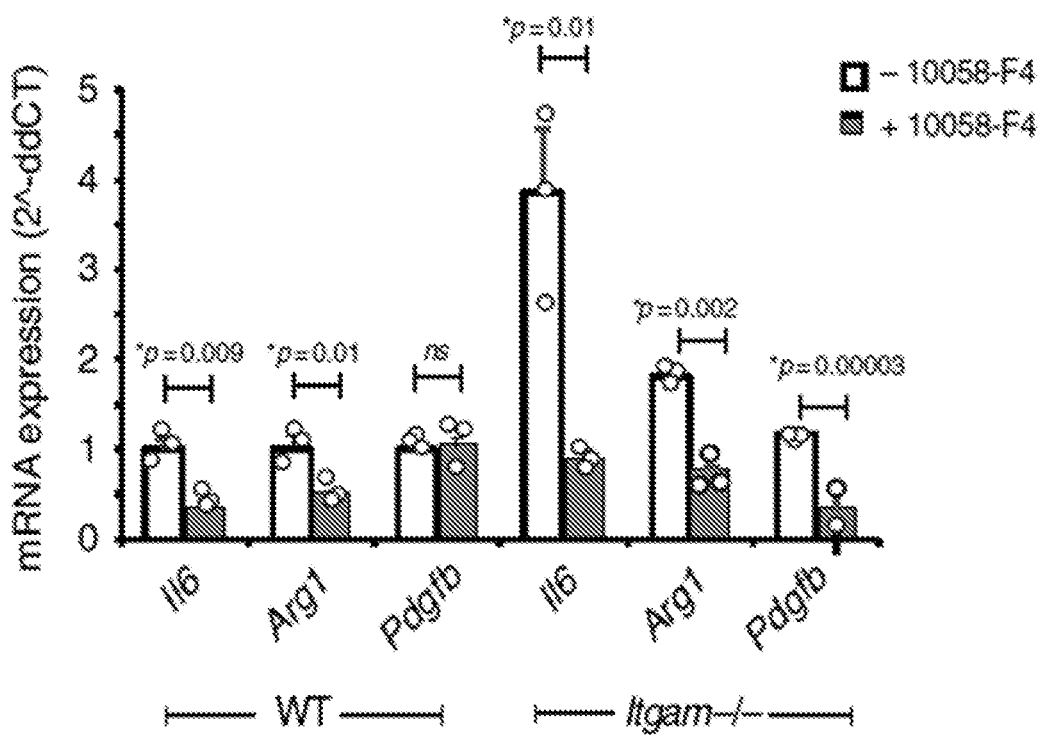
Figure 11D:
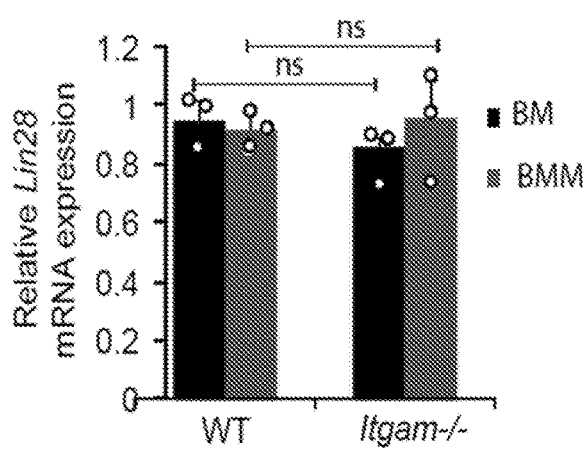
Figure 11E:
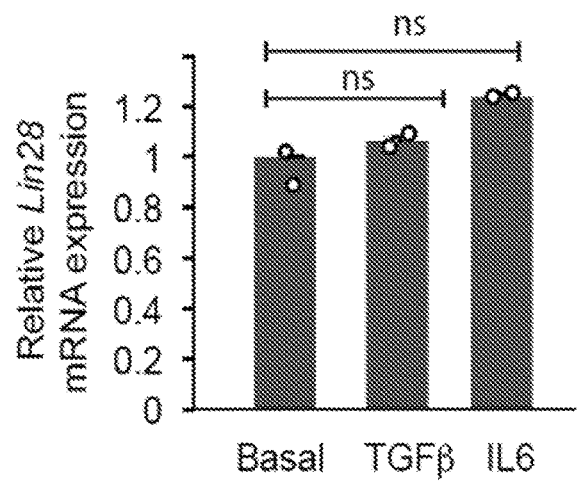

It was found that miRNA Let7a expression inversely correlated with Il6 expression in murine and human macrophages (FIGS. 11A-11B). As such, it was determined whether loss of CD11b expression in macrophages affects Let7a expression. Let7a expression was ablated in Itgam−/− and Itgam siRNA transduced macrophages and in the presence of neutralizing CD11b antibodies (FIGS. 3D and 11C) in a manner that was independent of Lin28, an RNA binding protein that cleaves and inactivates Let7, as Lin28 levels were not affected by CD11b expression or activation (FIGS. 11B, 11D and 11E). CD11b ligation by ICAM-1 promoted time-dependent Let7a expression, while inhibiting Il6 expression; conversely, suppression of adhesion inhibited Let7a expression and promoted Il6 expression in both murine and human macrophages (FIGS. 3E and 3F). Importantly, ectopic expression of Let7a miRNA (pre-miRNA) inhibited immune suppressive gene expression and stimulated pro-inflammatory gene expression in Itgam−/− macrophages, while anti-miRNA Let7a stimulated immune suppressive gene expression and inhibited immune stimulatory gene expression in WT macrophages (FIG. 3G). Similar to CD11b ablation (FIG. 1A), anti-miRNA Let7a stimulated Pdgfb expression, but had no effect on Vegfa expression (FIG. 3H). Together, these results indicate that CD11b activation promotes miRNA Let7a expression, which in turn inhibits immune suppressive macrophage gene expression.

c-Myc, a transcription factor that regulates basal and immune suppressive macrophage metabolism, binds to the Let7 promoter and suppresses Let7 transcription; interestingly, Let7 can also suppress c-Myc expression[44,45]. It was found that c-Myc gene was upregulated in Itgam−/− macrophages compared with WT macrophages (FIG. 3I). c-Myc protein expression and serine 62 phosphorylation, which stabilizes the transcription factor[46], were also upregulated in Itgam−/− macrophages compared with WT macrophages (FIG. 3J). It was then asked whether inhibition of cMyc function could promote Let7 expression and thereby alter macrophage polarization. Importantly, Let7a, Let7d, and Let7f expression was reduced in Itgam−/− macrophages; however, pharmacological inhibition of c-Myc restored Let7 expression in Itgam−/− macrophages and reversed the increased immune suppressive gene expression exhibited by Itgam−/− macrophages (FIGS. 3K and 3L). Together, these data indicate that integrin CD11b functions to suppress Myc expression and immune suppressive macrophage polarization in a Let7 dependent manner.

Figure 4A:
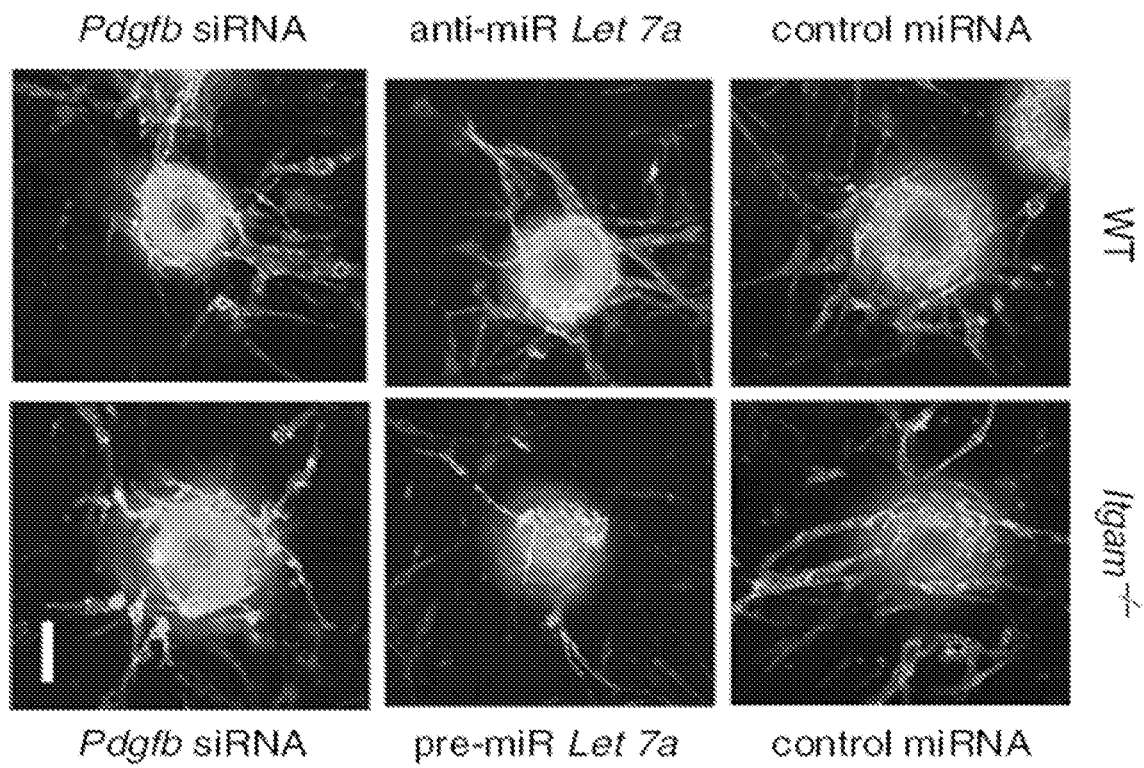
Figure 4C:
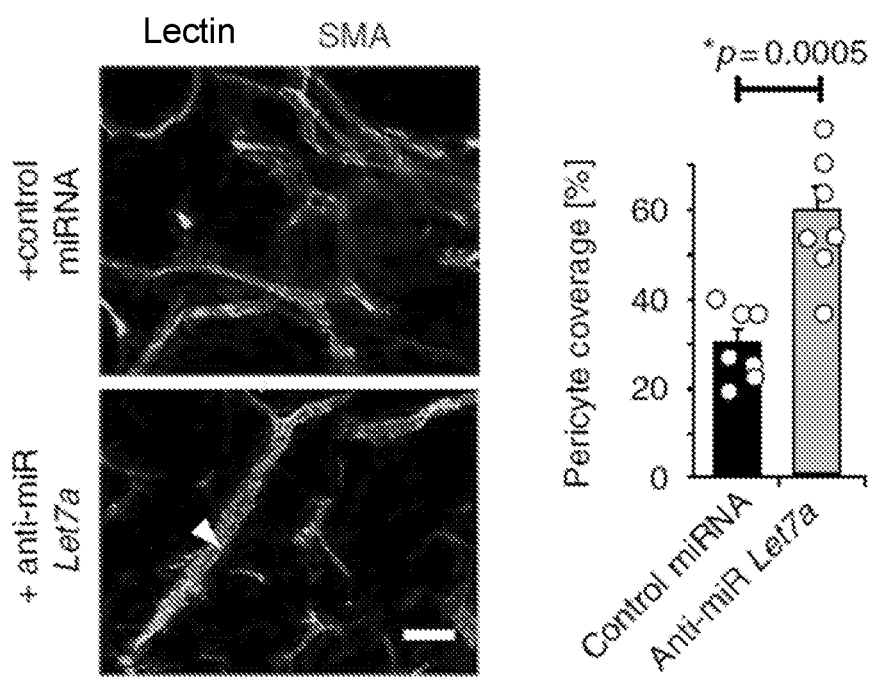
Figure 4B:
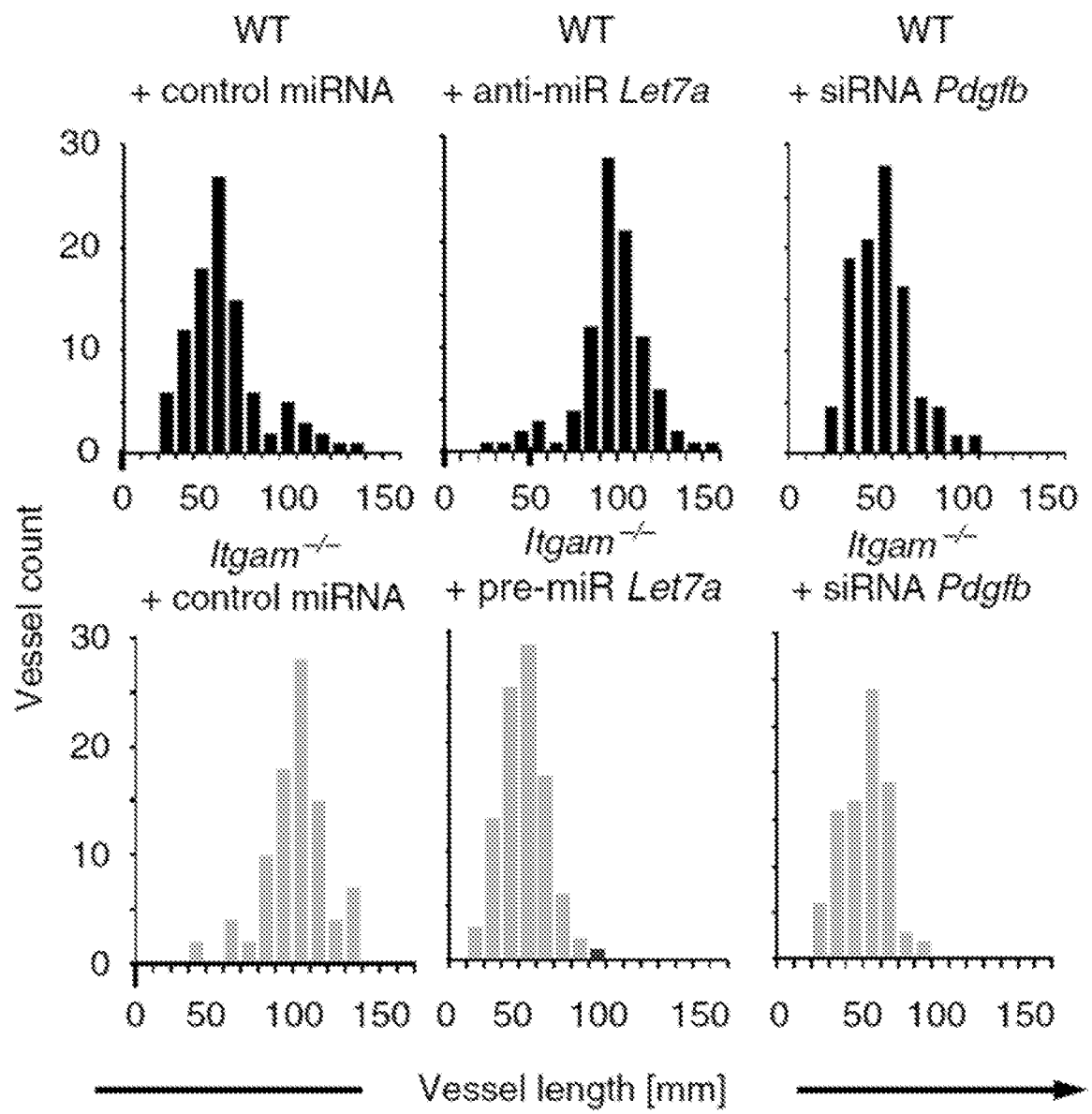
Figure 11F:
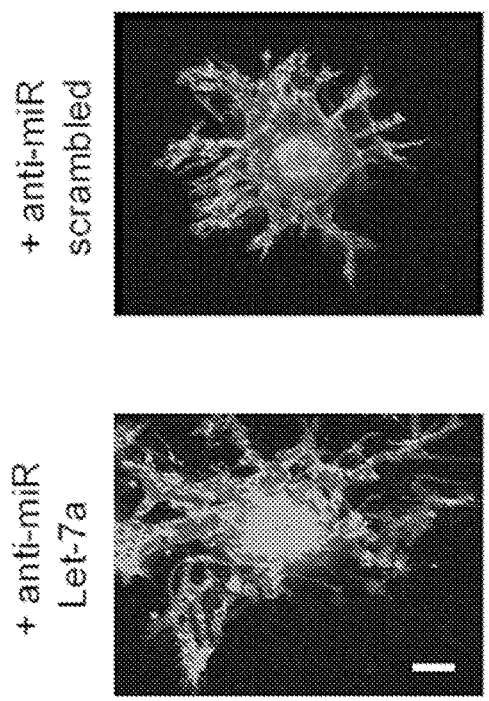
Figure 11F:
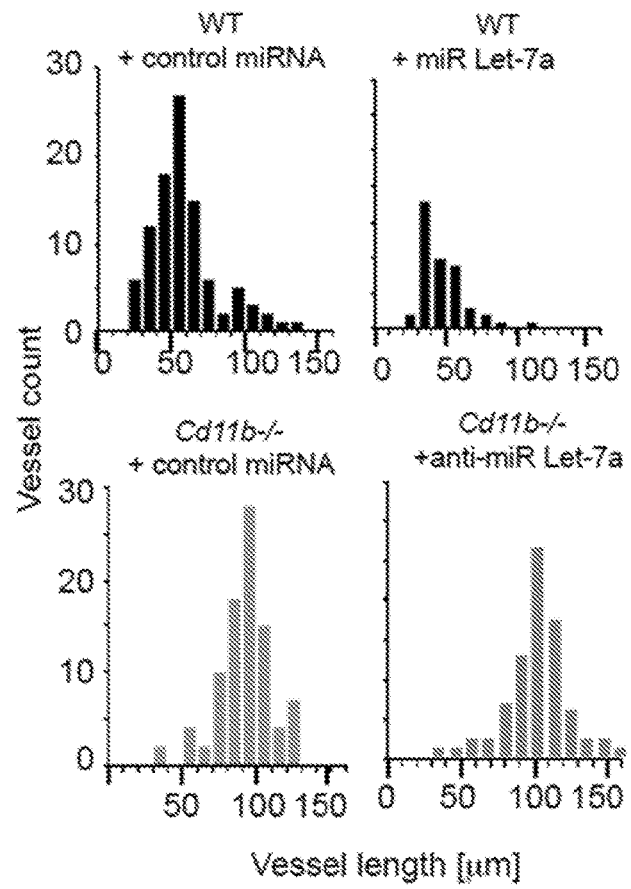
Figure 12A:
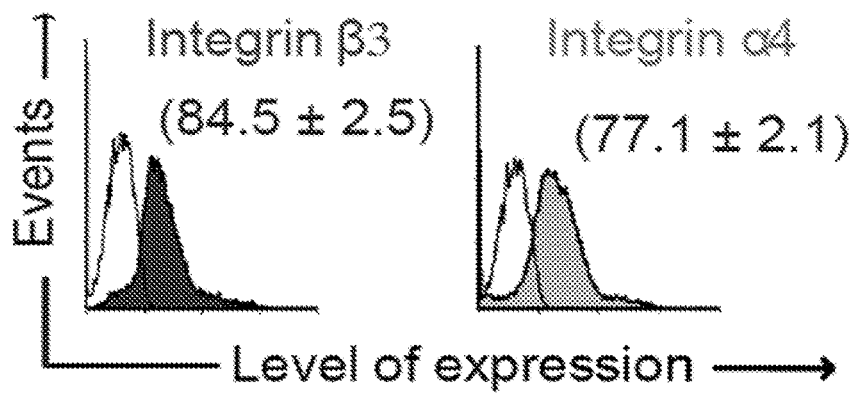
FIGS. 12A-12H are pictorial and graphical diagrams showing RGD-coated nanoparticles target circulating and tumor associated myeloid cells.
Figure 12B:
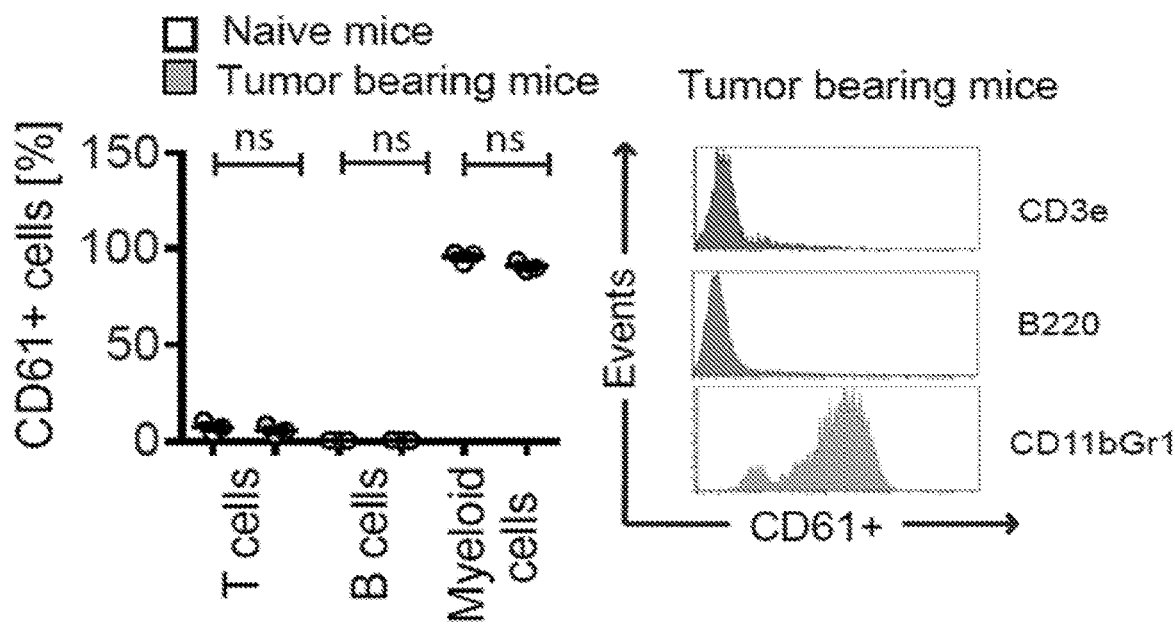
Figure 12C:
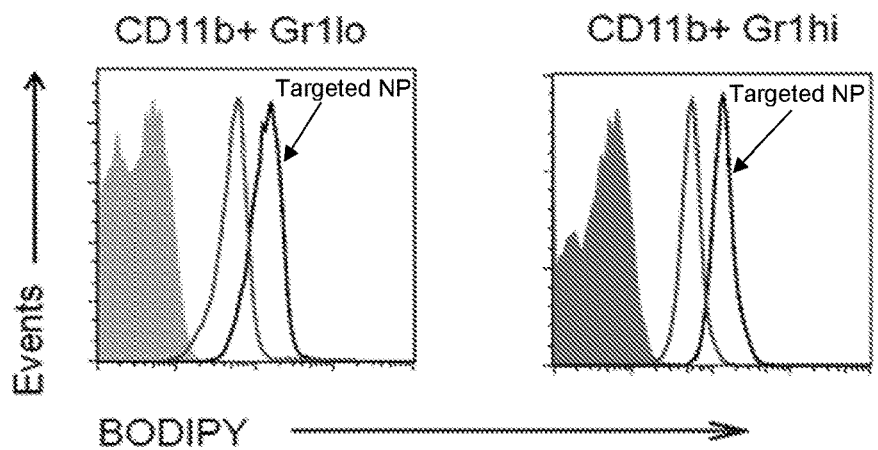
Figure 12D:
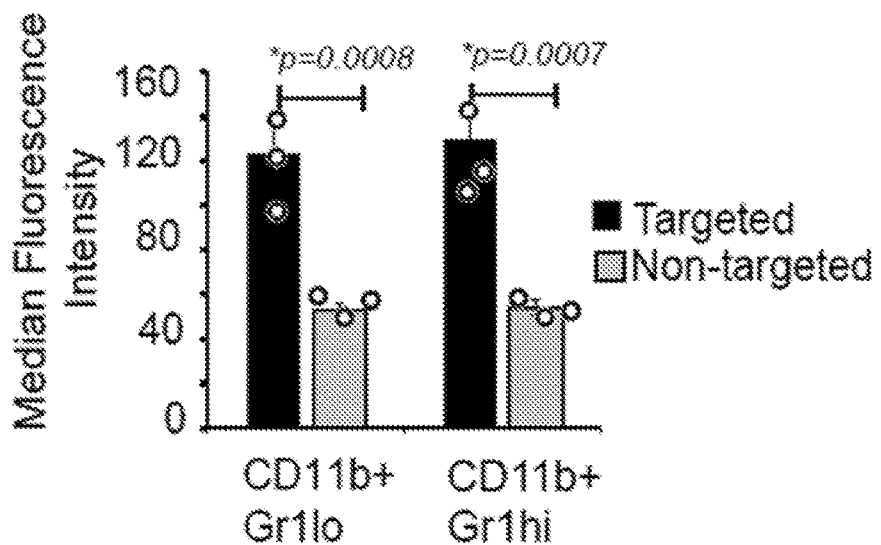
Figure 12E:
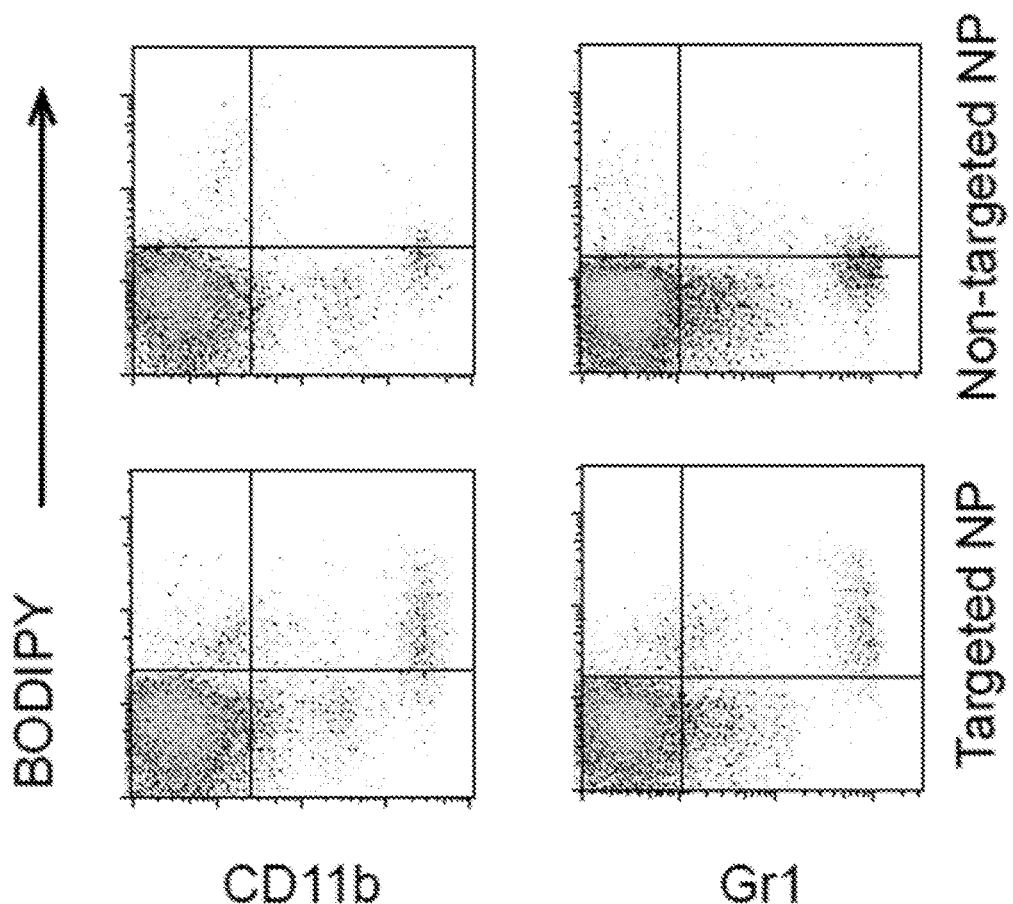
Figure 12F:
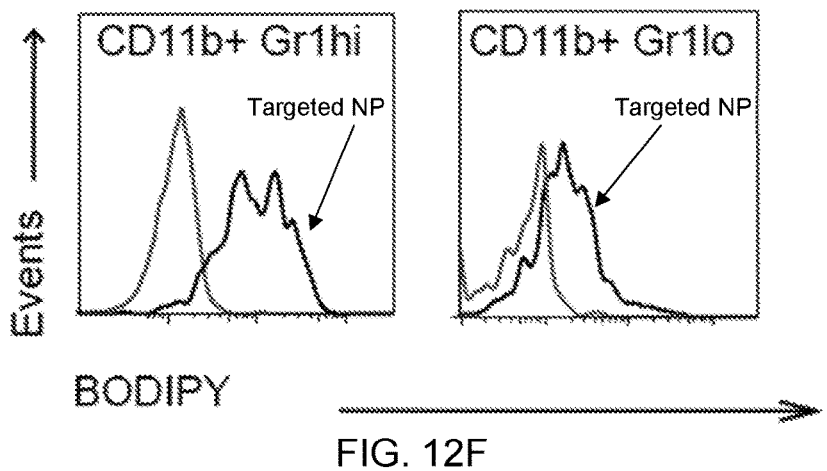
Figure 12G:
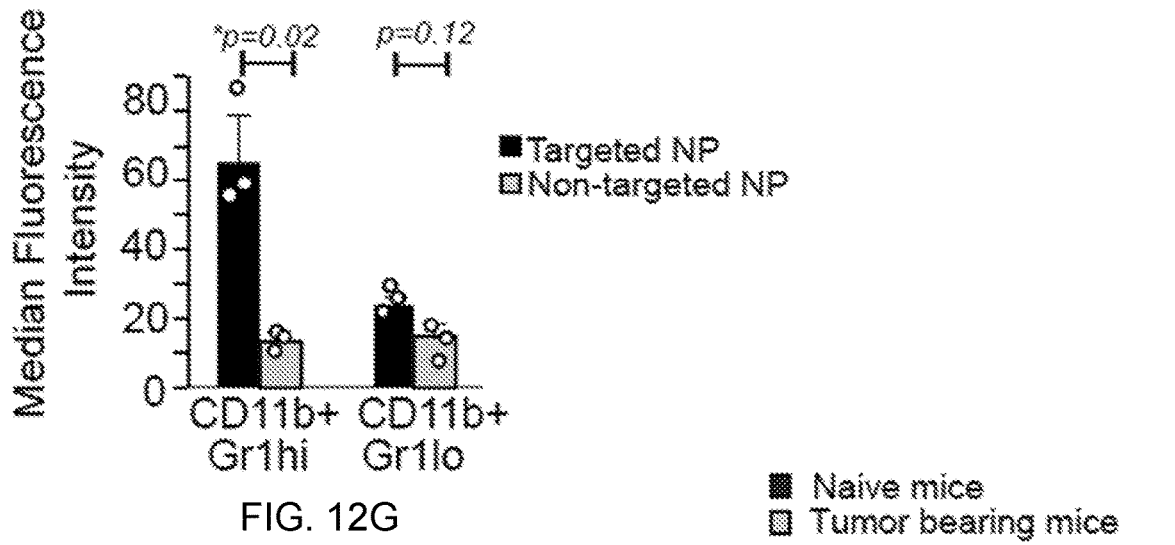
Figure 12H:
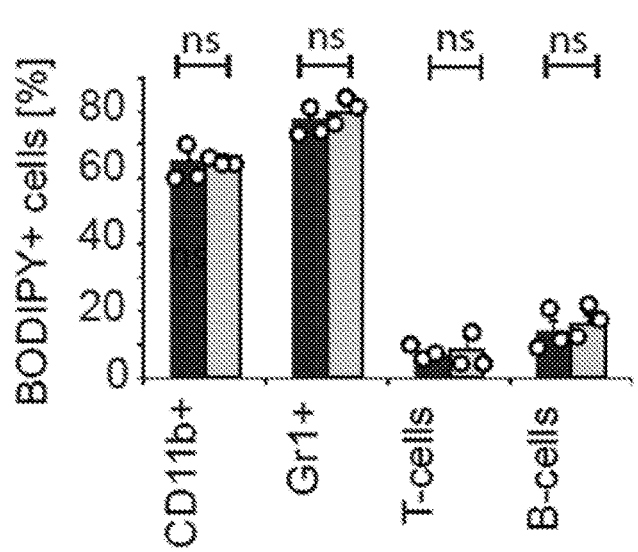

Because Let7a inhibits macrophage-mediated Pdgfb expression, the effect of Let7a expression on neovascularization was investigated in vitro and in vivo. Endothelial cells and vascular smooth muscle cells attached to microcarrier beads were cultured in fibrin gels that contained either WT or Itgam−/− macrophages that were transduced with control miRNA, pre-miRNA Let7a, anti-miRNA Let7a or Pdgf-bb siRNA. Itgam−/− macrophages stimulated sprout elongation that was inhibited by transduction of macrophages with Let7a miRNA or Pdgfb siRNA (FIGS. 4A, 4B and 11F). In contrast, expression of anti-miRNA Let7a in WT but not Itgam−/− macrophages stimulated sprout elongation (FIGS. 4A, 4B and 11F). Additionally, macrophages transduced with anti-miR Let7a stimulated the formation of mature, pericyte-coated blood vessels in bFGF-saturated Matrigel in vivo (FIG. 4C). Together, these studies show that CD11b controls neovascularization through the regulation of Let7a and subsequent PDGF-BB expression.

Figure 4D:
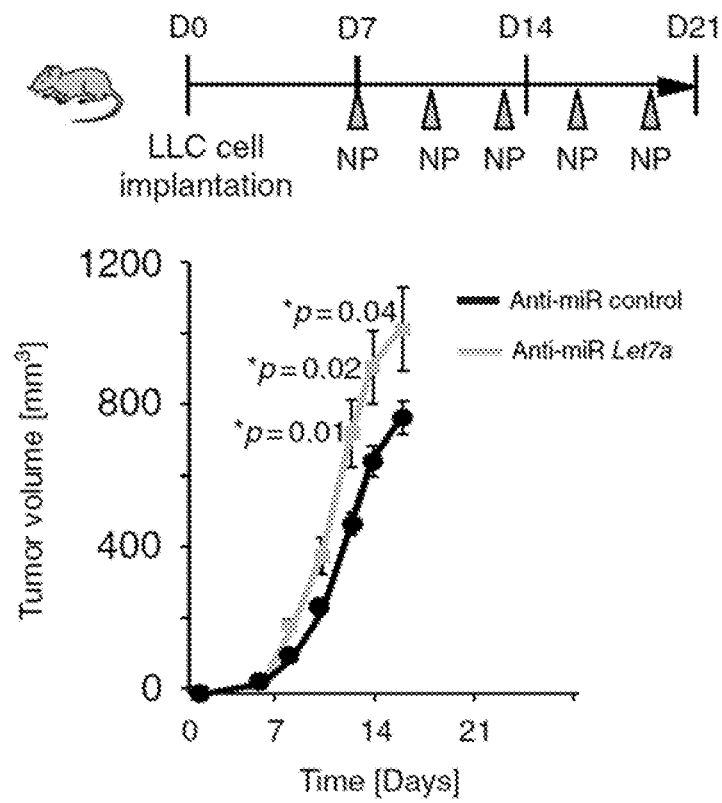
Figure 4E:
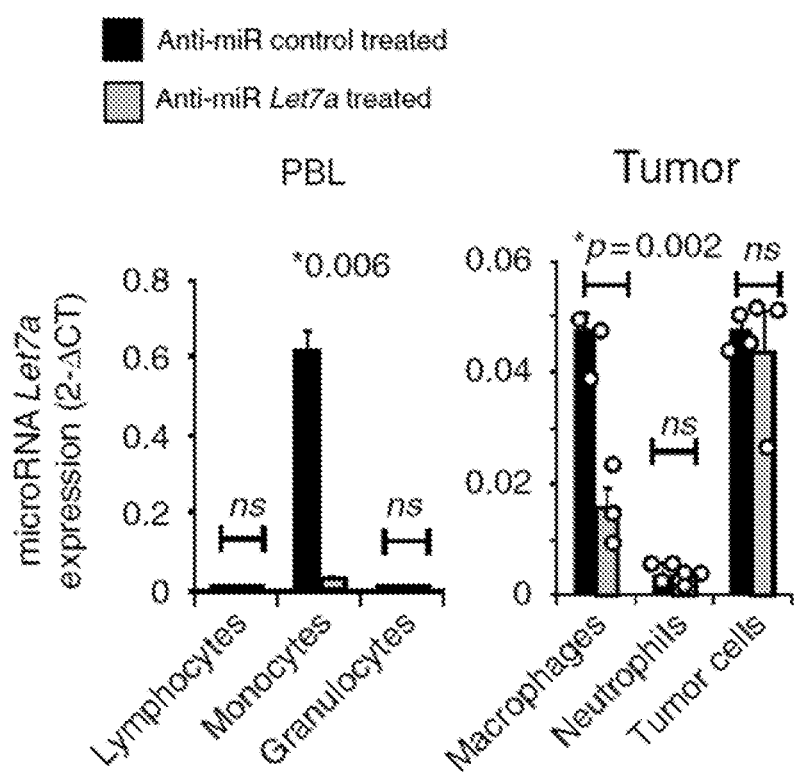
Figure 4F:
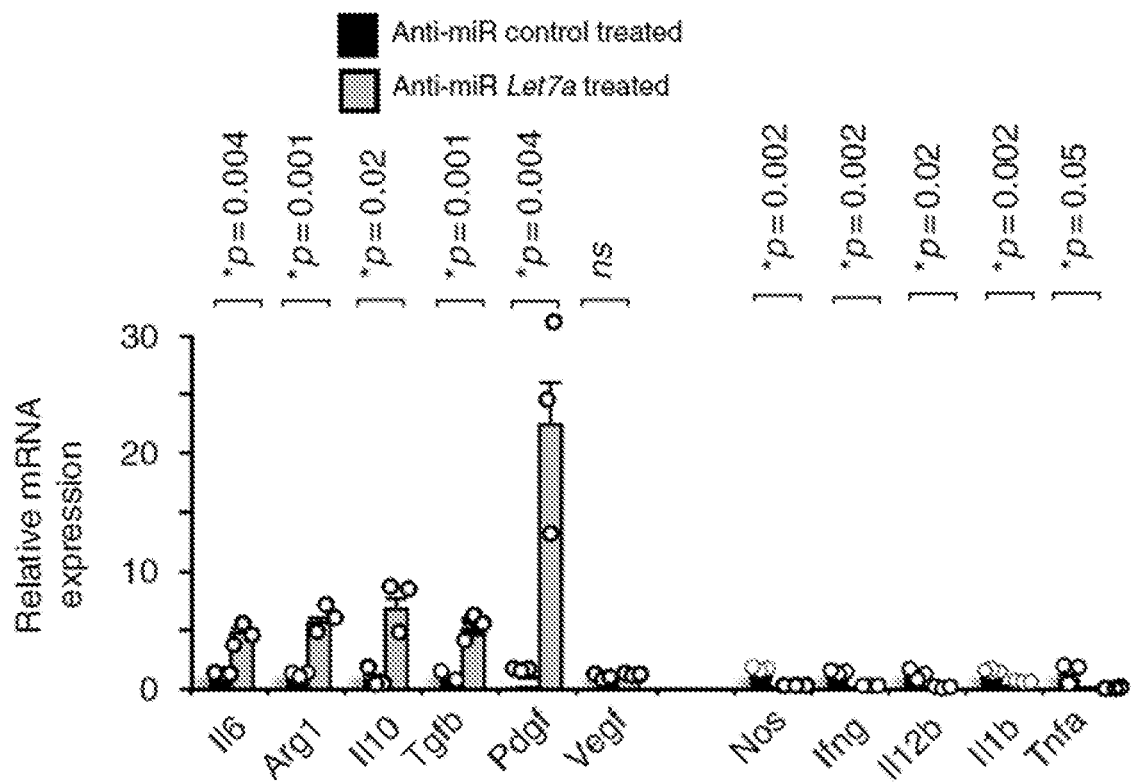
Figure 4G:
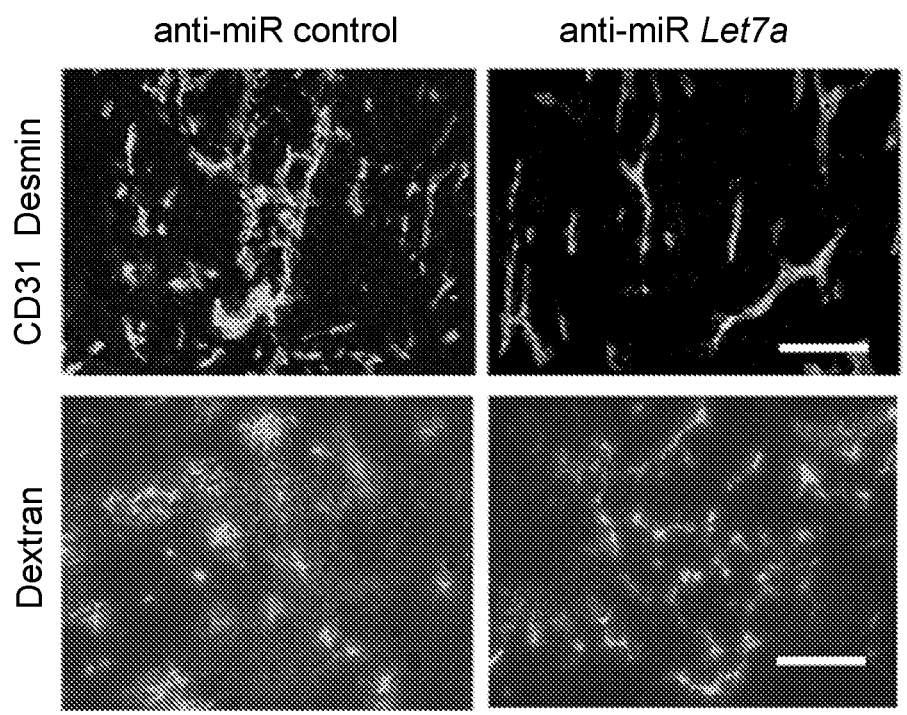
Figure 13A:
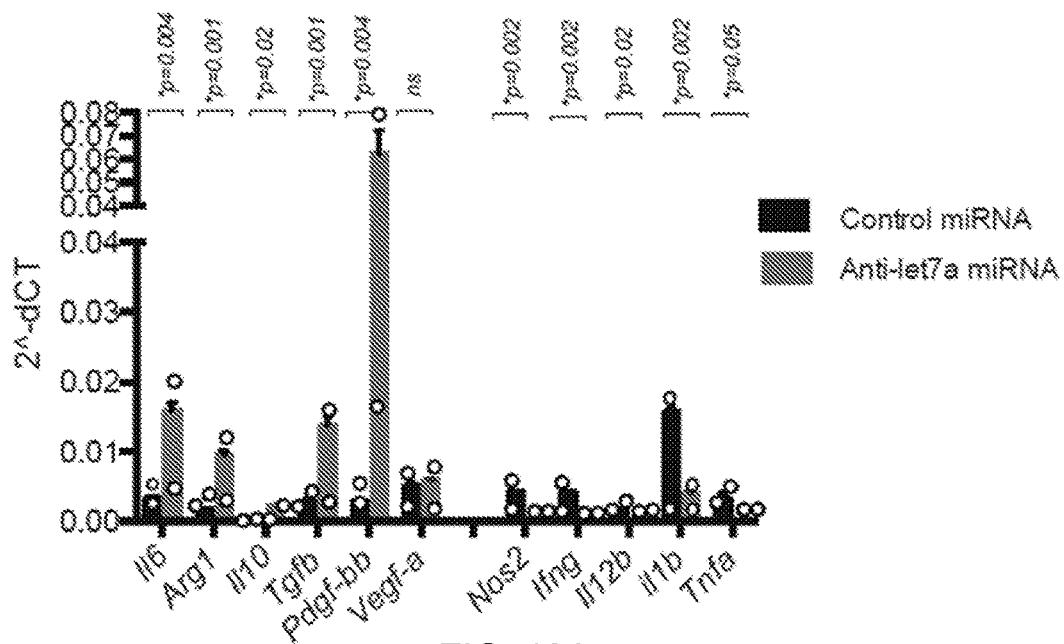
FIGS. 13A-13C are graphical diagrams showing the effect of Let7a and CD11b inhibition on tumors.

To test the role of Let7a in the regulation of tumor immune suppression and neovascularization, anti-miR Let7a was delivered to tumors in targeted nanoparticles in vivo (FIG. 4D). It was found that integrin αvβ3-targeted particles were specifically taken up by circulating myeloid cells in normal and tumor bearing animals (FIGS. 12A-12H). Delivery of anti-miRNA Let7a stimulated LLC tumor growth, comparable to that observed in Itgam−/− mice (FIG. 4D). Although Let7a is expressed in immune and non-immune cells in tumors, it was found that delivery of anti-miR Let7a only inhibited Let7a expression in circulating monocytes and tumor associated macrophages but not in other tumor associated cells (FIG. 4E). Importantly, anti-miRNA Let7a stimulated immune suppressive and pro-angiogenic gene expression and inhibited pro-inflammatory gene expression in tumors compared with controls (FIGS. 4F and 13A). Anti-miRNA Let7a also stimulated blood vessel normalization in transfected tumors, as vessels were longer, less branched, heavily coated with pericytes and less leaky than vessel from control transfected tumors (FIGS. 4G and 4H). Anti-Let7a also suppressed CD8+ T cell recruitment to tumors and enhanced CD4+ T cell recruitment to tumors (FIG. 4I). Together, these results indicate that CD11b restrains immune suppression and vascular maturation through its regulation of miRNA Let7a.

Thus, the methods of treating cancer may include administering to the subject in need thereof, a therapeutically effective amount of miRNA Let7a. It should be understood that such methods may also include administering a therapeutically effective amount of an agonist of CD11b expression in combination with a therapeutically effective amount of miRNA Let7a. Such compounded treatment regimens may include administering the agonist of CD11b expression first, followed by the therapeutically effective amount of miRNA Let7a, or vice versa. In various embodiments, both the agonist of CD11b expression and the miRNA Let7a are administered simultaneously.

Advances in basic, translational, and clinical research have revealed the power of cancer immunotherapy. Immune checkpoint inhibitors such as anti-programmed death (PD)-1, anti-PD ligand l(PD-L1), anti-cytotoxic T lymphocyte-associated antigen (CTLA)4 antibodies, which suppress the functions of T cell inhibitory receptors (immune checkpoints), and chimeric antigen T cell receptor (CAR-T) therapies are therapeutic strategies that can increase the content of activated, tumor-specific cytotoxic T cells (CTLs) in various tumors. Currently, approved checkpoint inhibitors for cancer therapy include pembrolizumab, nivolumab, and cemiplimab (anti-PD-1); atezolizumab, avelumab, and durvalumab (anti-PD-L1); and ipilimumab (anti-CTLA-4). However, many cancer patients have exhibited resistance to immunotherapies, with ongoing research indicating that resistance to checkpoint inhibitors or adoptive T cell immunotherapies can be mediated by abundant tumor-associated myeloid cell infiltrates, including macrophages, monocytes, and granulocytes.

Prior studies have shown that increased vascular normalization in tumors can improve tumor perfusion and promote responsiveness to therapy[23-36]. To determine whether the vascular normalization induced by anti-miRNA Let7a might enhance the efficacy of chemotherapy by increasing tumor perfusion, mice bearing LLC tumors were treated with targeted delivery of anti-miRNA Let7a or control miRNA in combination with chemotherapy (gemcitabine) (FIG. 4J).

Chemically, gemcitabine is a nucleoside analog in which the hydrogen atoms on the 2' carbon of deoxycytidine are replaced by fluorine atoms. As with analogues of pyrimidines, the triphosphate analogue of gemcitabine replaces one of the building blocks of nucleic acids, in this case cytidine, during DNA replication. The process has been shown to arrest tumor growth, as only one additional nucleoside can be attached to the "faulty" nucleoside, resulting in apoptosis.

Figure 4K:
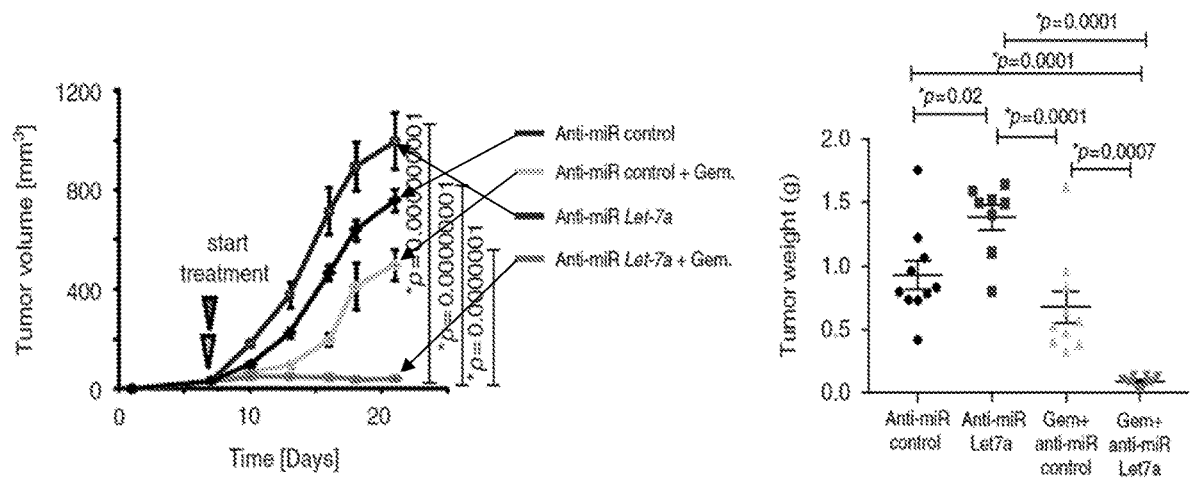
Figure 13B:
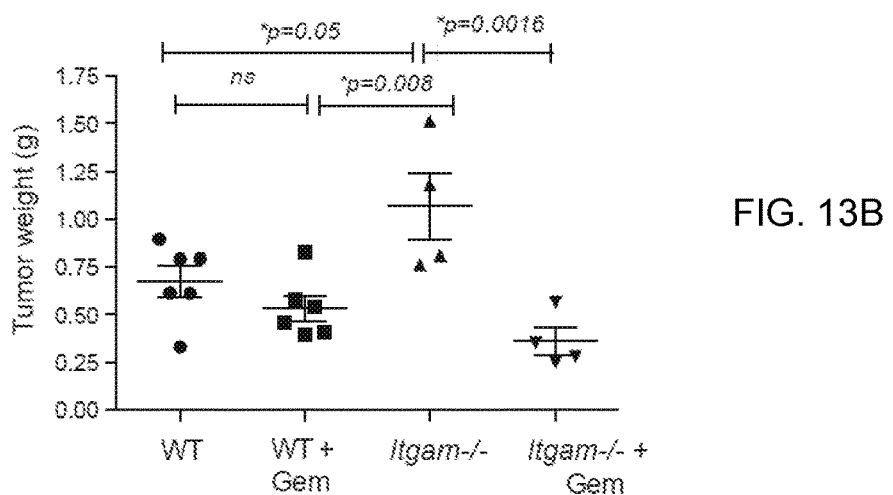
Figure 13C:
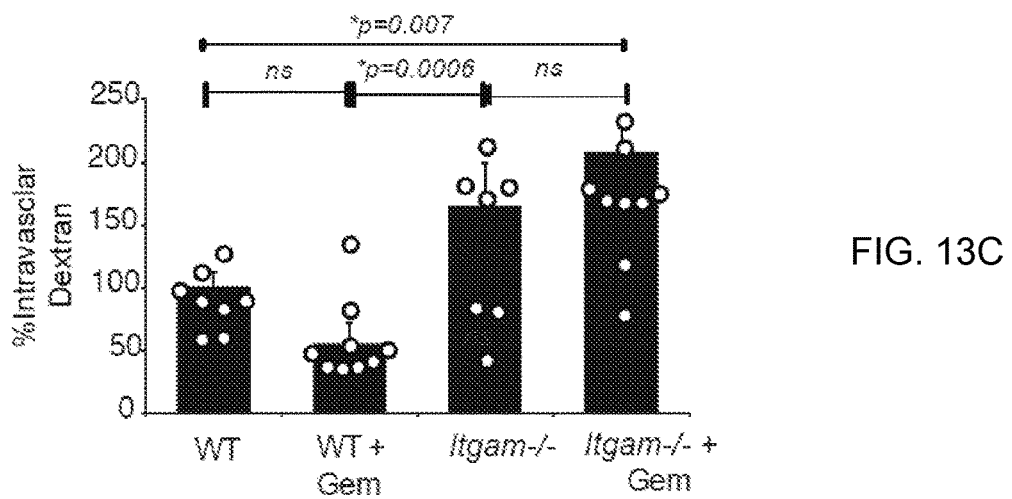

Whereas anti-miRNA Let7a promoted LLC tumor growth, anti-miRNA Let7a combined with gemcitabine substantially reduced tumor growth, consistent with the notion that Let7a inhibition increases accessibility of the tumor to chemotherapy (FIG. 4K). In accordance with these results, it was found that gemcitabine treatment of Itgam−/− mice suppressed tumor growth more profoundly than gemcitabine treatment of WT mice (FIG. 13B). As Itgam−/− exhibited greater perfusion (less vascular leak) than WT mice (FIG. 13C), these studies indicate that CD11b, through its effects on miRNA Let7a, plays a critical role in regulating tumor immune and vascular responses.

Figure 5C:
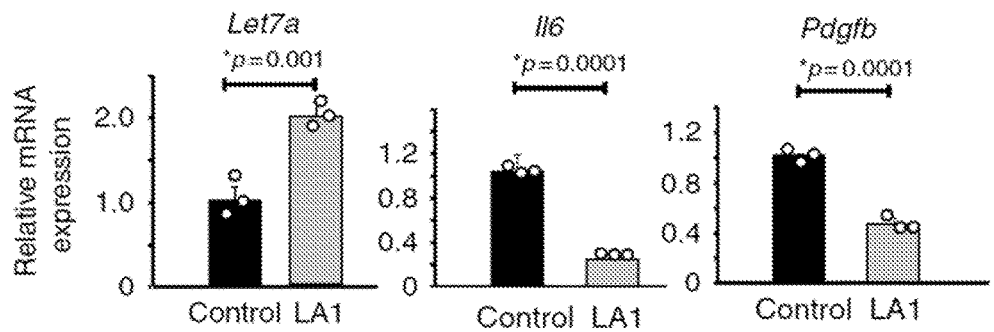
Figure 14A:
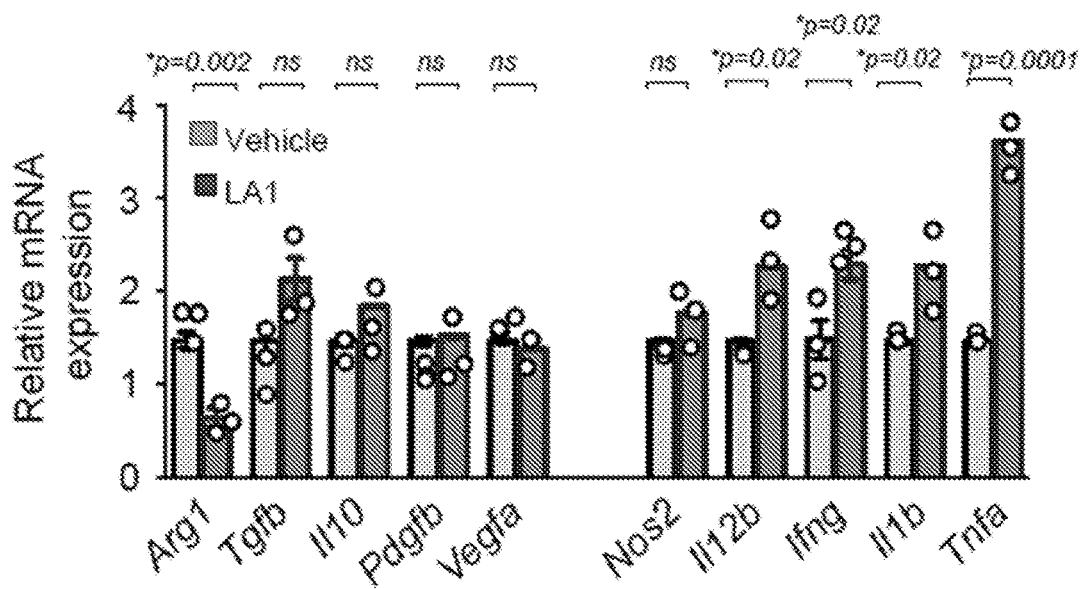
FIGS. 14A-14F are pictorial and graphical diagrams showing effects of LA1 on tumor progression.

The results provided herein suggested that targeted pharmacologic activation of CD11b in vivo can repolarize tumor associated macrophages, with subsequent inhibition of tumor immune suppression and tumor growth. The effects of a small molecule agonist of CD11b, leukadherin 1 (LA1)[47,48] (FIG. 5A) were then investigated on macrophage polarization and tumor growth. LA1 stimulated myeloid cell adhesion to ICAM-1 coated substrates in a manner that is inhibited by anti-CD11b-neutralizing antibodies (FIG. 5B). LA1 stimulated macrophage immune response gene expression, illustrated by increases in expression of Il1b, Tnfa, Il12, Nos2 and Ifng mRNAs (FIG. 14A). As LA1 stimulated Let7a expression and inhibited Pdgfb and Il6 expression (FIG. 5C), these results suggest that LA1 might stimulate pro-inflammatory immune responses that could inhibit tumor growth in vivo.

Thus, in another aspect, the methods of treating cancer in a subject may also include administering a therapeutically effective amount of (i) one or more of an agonist of CD11b activity or expression, such as LA1 and anti-miRNA Let7a, in combination with (ii) one or more chemotherapeutic agents, such as checkpoint inhibitors for cancer therapy.

Figure 5D:
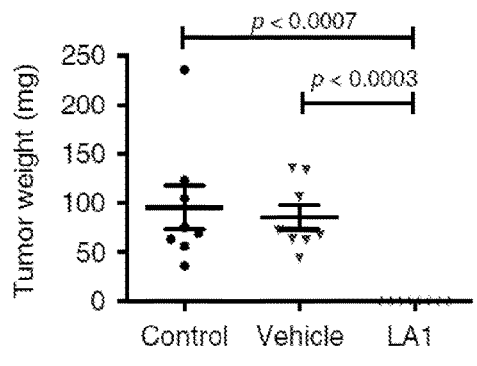
Figure 5E:
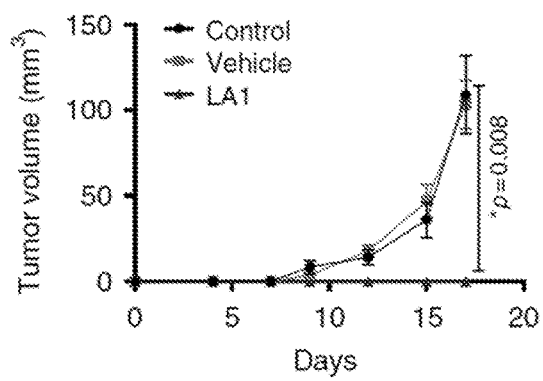
Figure 5F:
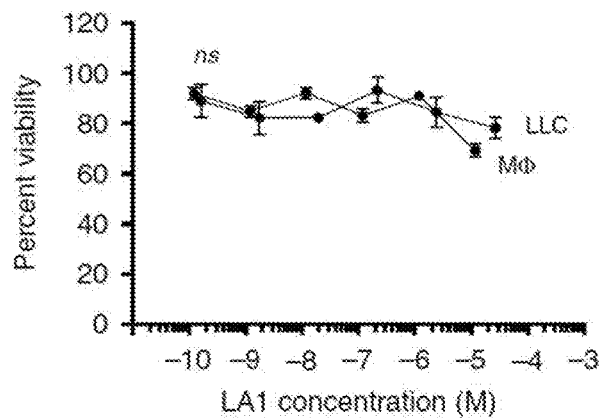
Figure 5H:
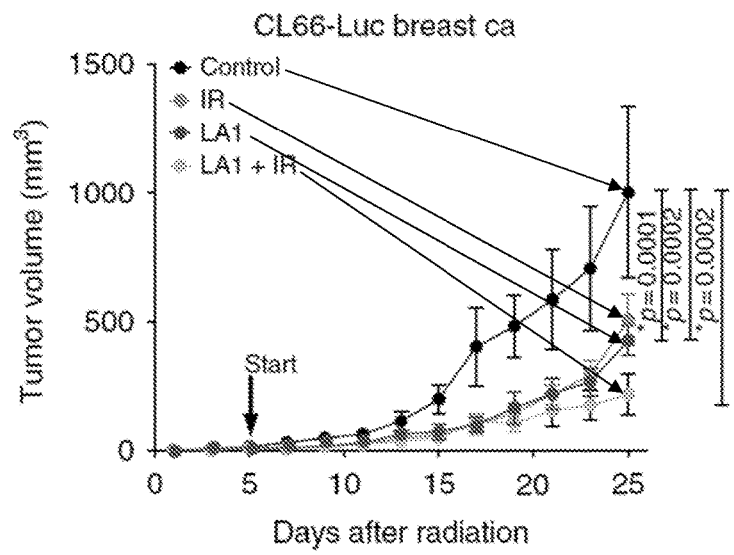
Figure 5G:
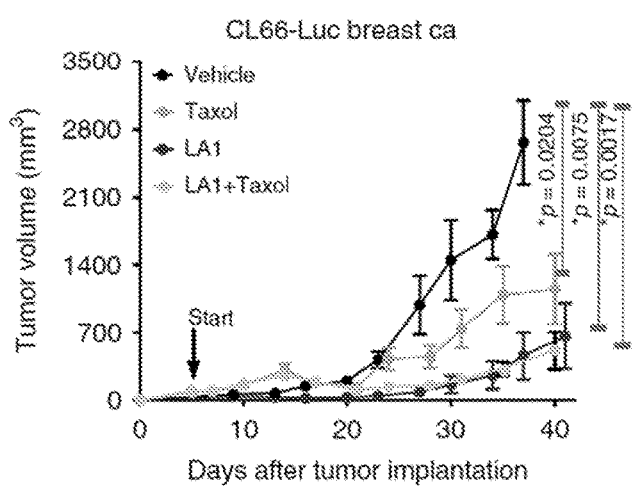
Figure 5J:
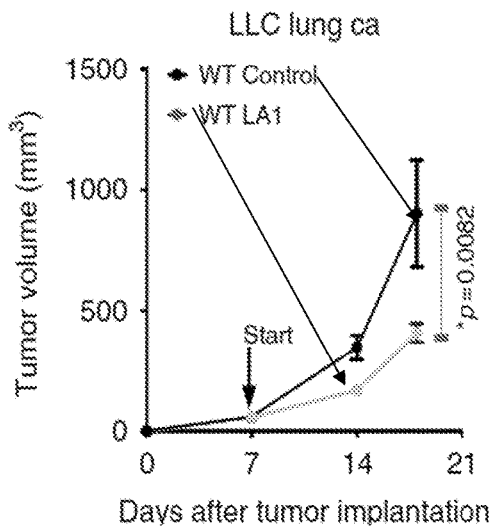
Figure 5I:
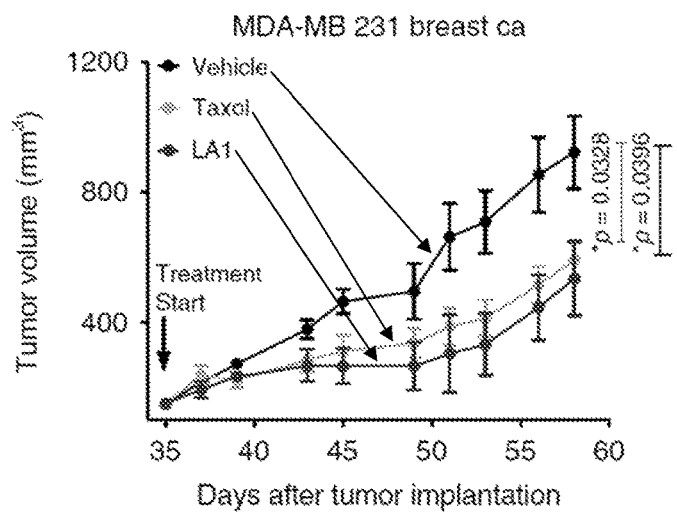
Figure 5K:
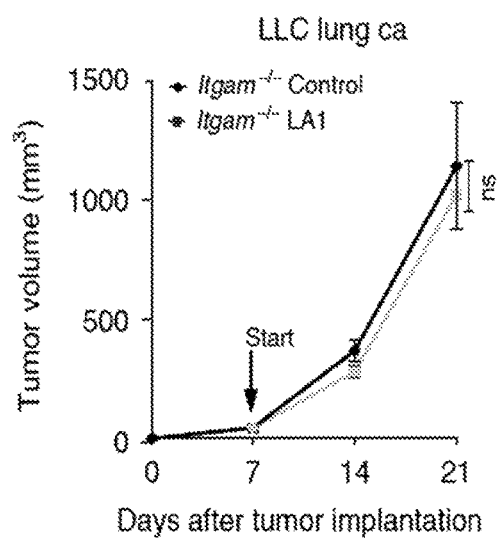
Figure 14B:
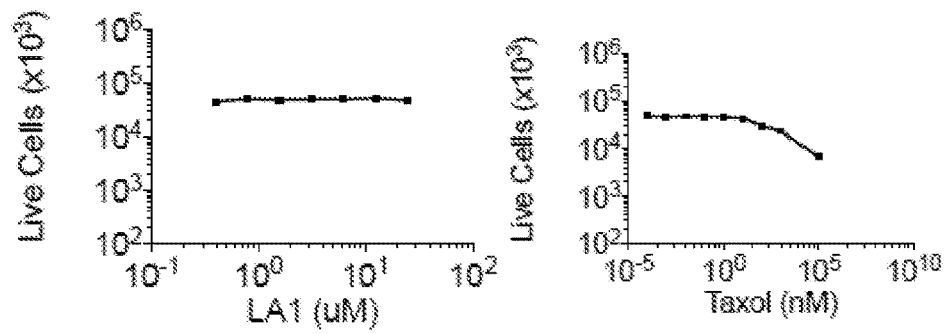

To assess the effects of LA1 on tumor associated macrophages in vivo, tumor associated macrophages were isolated[10], treated with LA1 prior and co-implanted with LLC tumor cells. LA1-treated macrophages completely inhibited tumor growth (FIGS. 5D and 5E) even though LA1 had no direct effect on LLC or macrophage viability (FIGS. 5E and 5F). Although LA1 had no effect on CL66-Luc breast tumor cell growth in vitro (FIG. 14B), LA1 potently reduced tumor growth in syngeneic, orthotopically implanted CL66-Luc breast tumors more effectively than taxol (FIG. 5G). LA1 also synergized with irradiation to suppress CL66-Luc breast tumor growth (FIG. 5H) and suppressed the growth of orthotopic, human MDA-MB-231 mammary xenograft tumors (FIG. 5I). It was observed that LA1 inhibited murine LLC lung tumor growth in WT but not in Itgam−/− mice, indicating that LA1 acts through integrin CD11b to suppress the growth of tumors (FIGS. 5J and 5K).

Figure 5M:
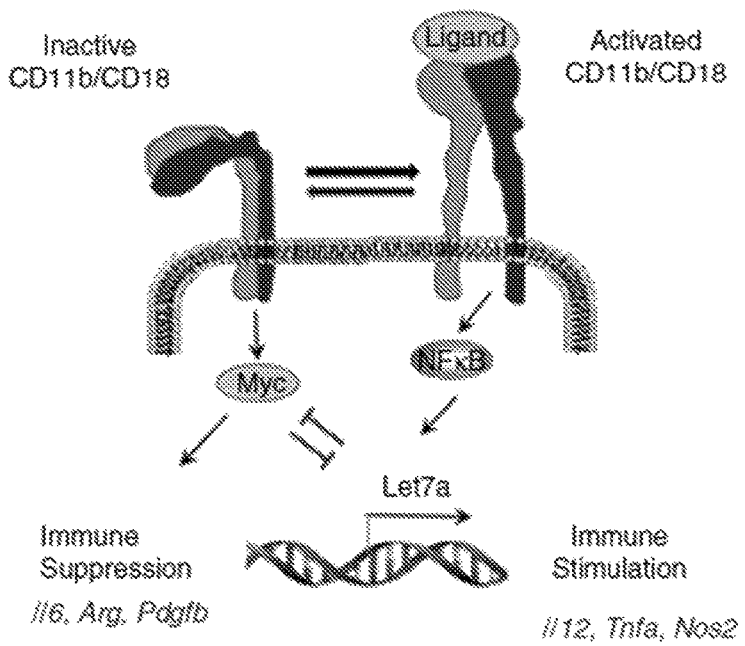
Figure 5L:
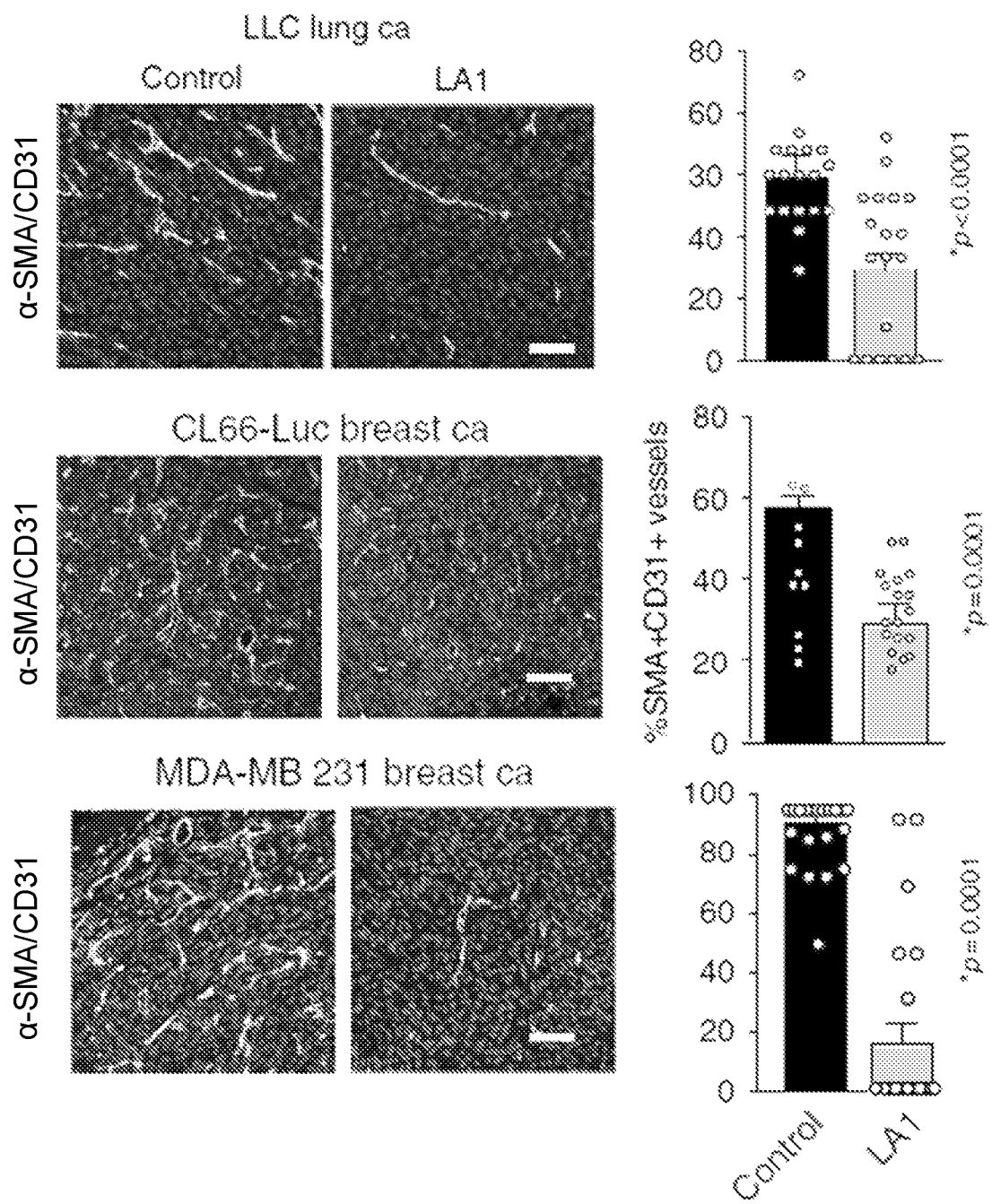
Figure 6:
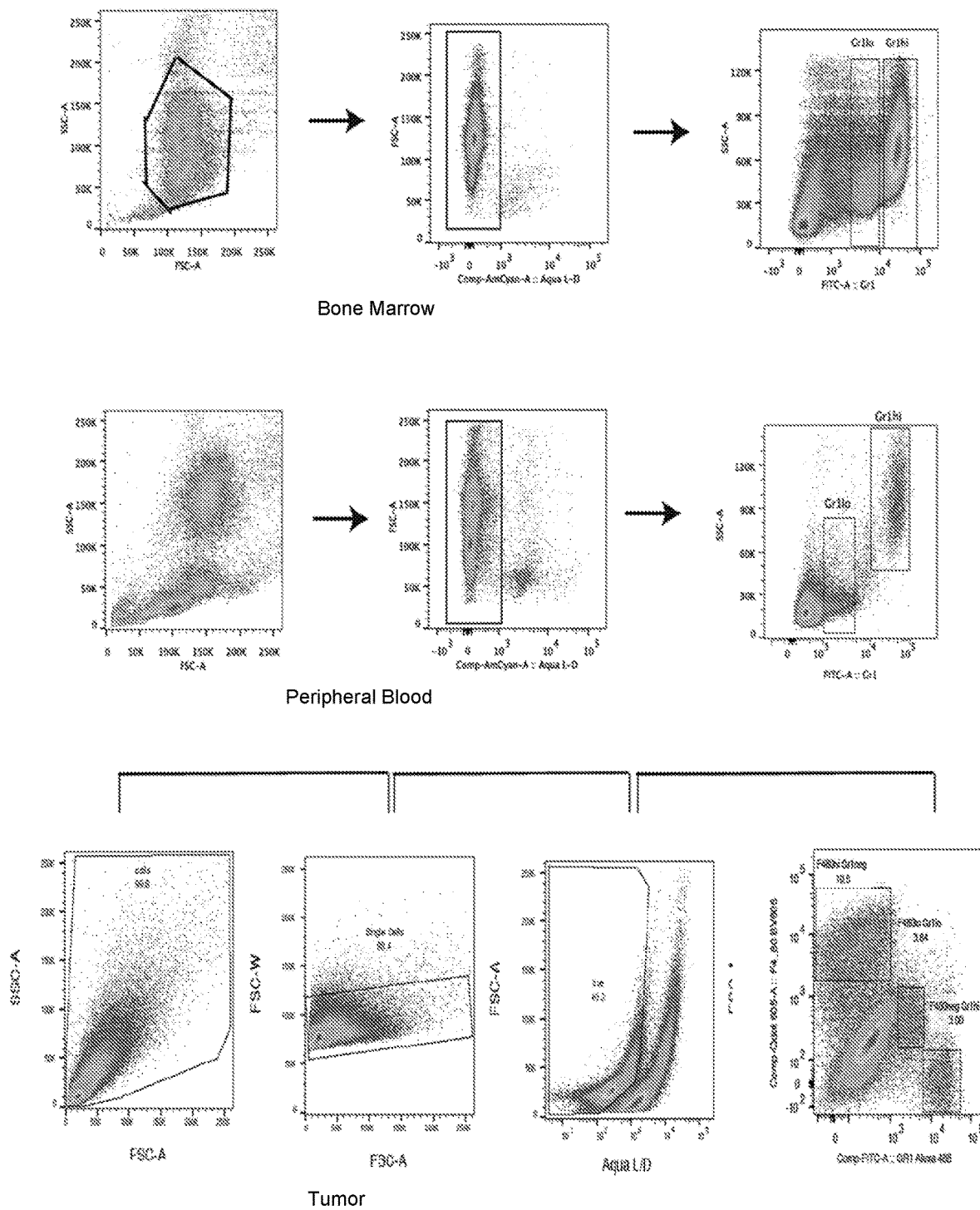
FIG. 6 is a series of graphical diagrams showing flow cytometry analysis schematics for myeloid cells in bone marrow, peripheral blood and tumor from WT and Itgam−/− mice.
Figure 14C:
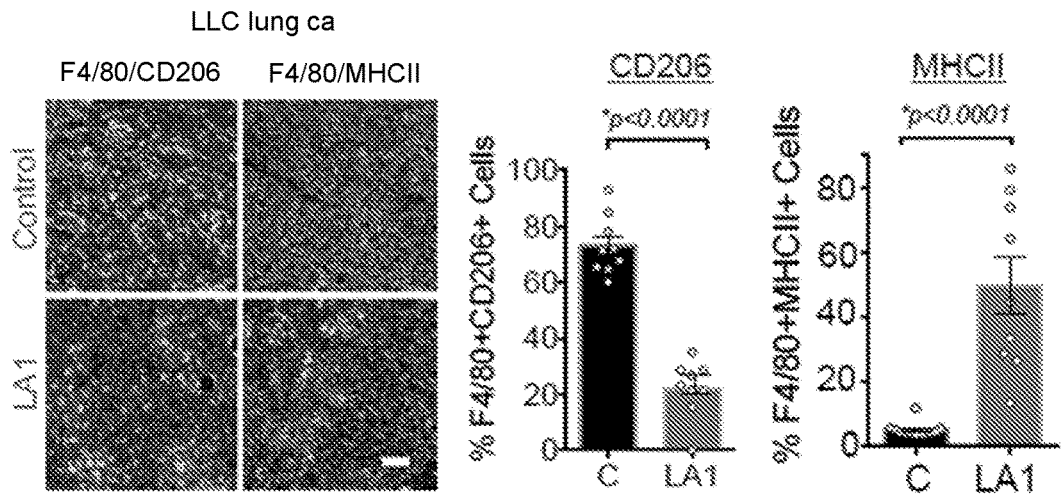
Figure 14D:
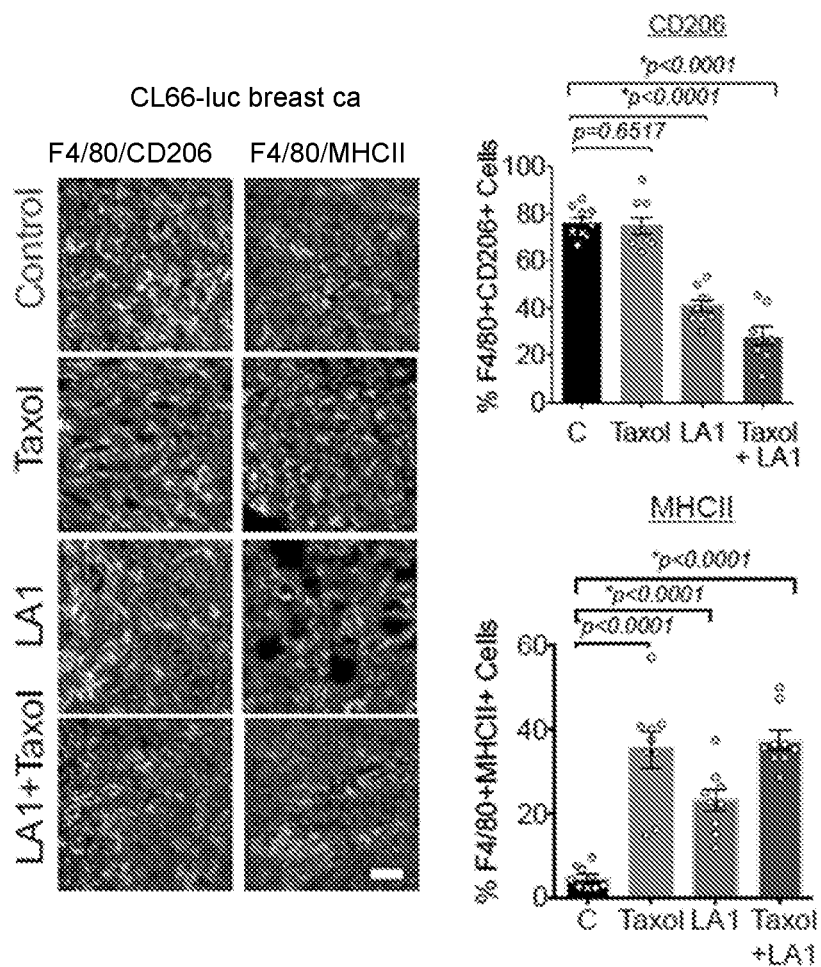
Figure 14E:
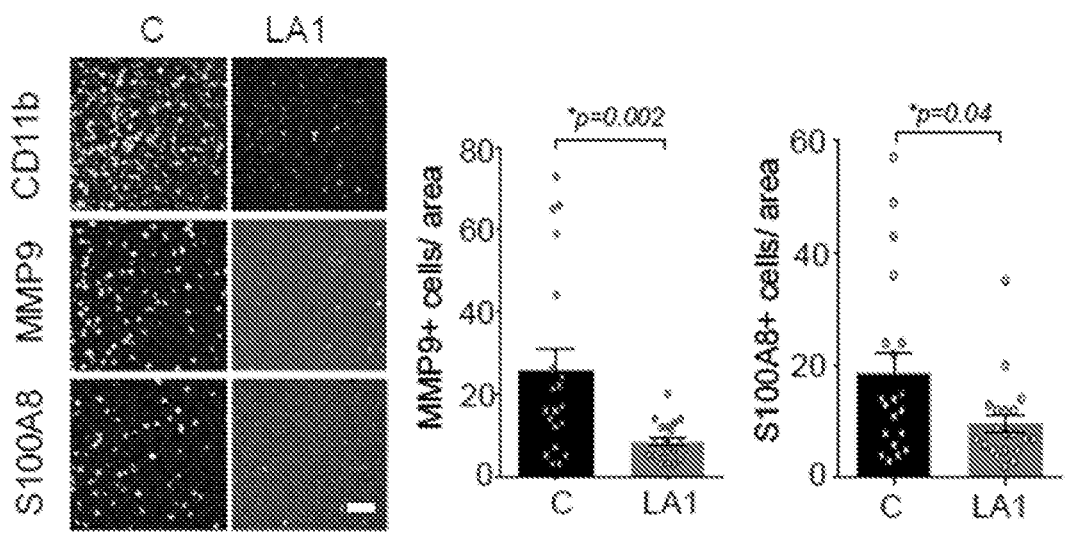
Figure 14F:
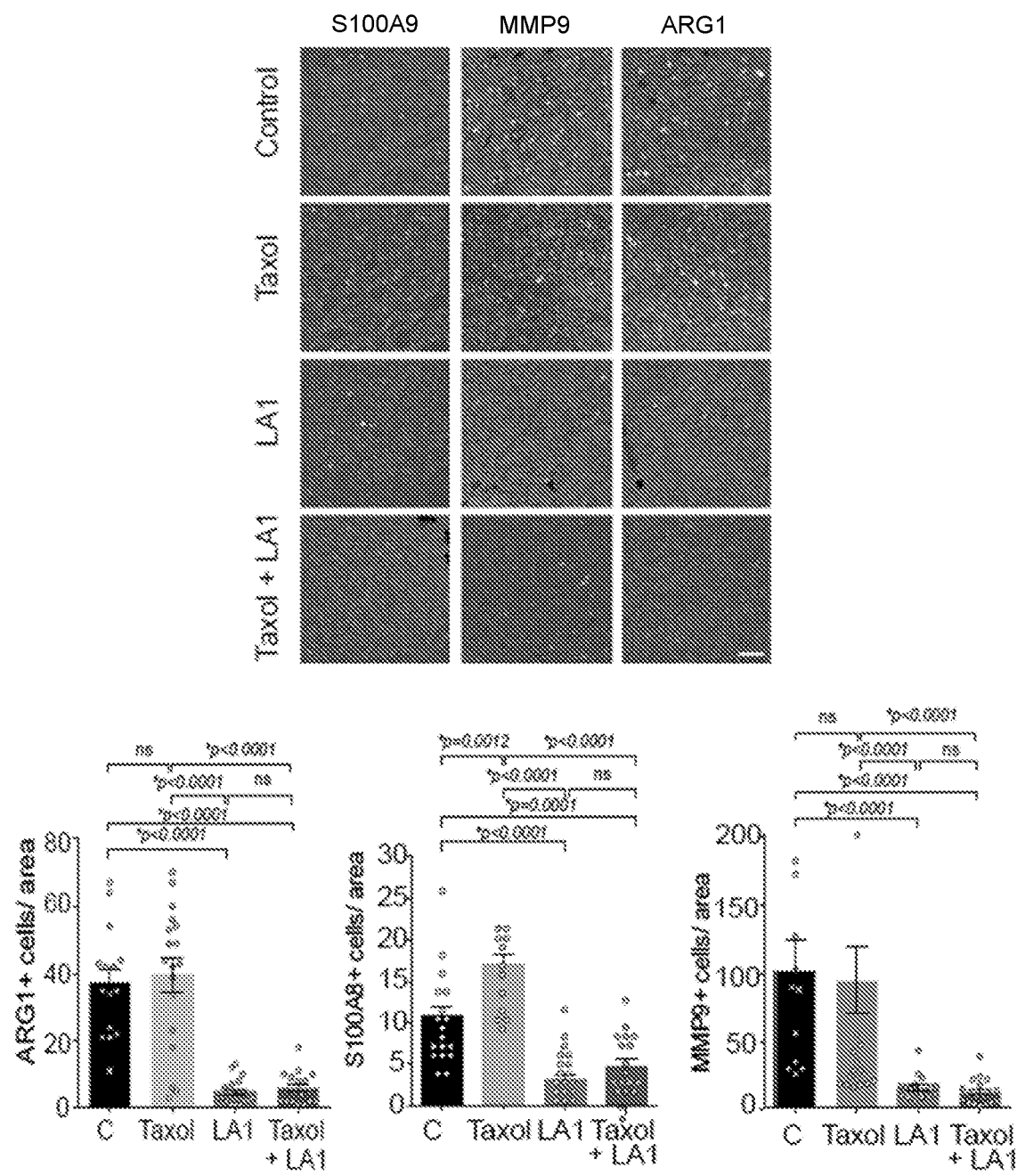
Figure 15A:
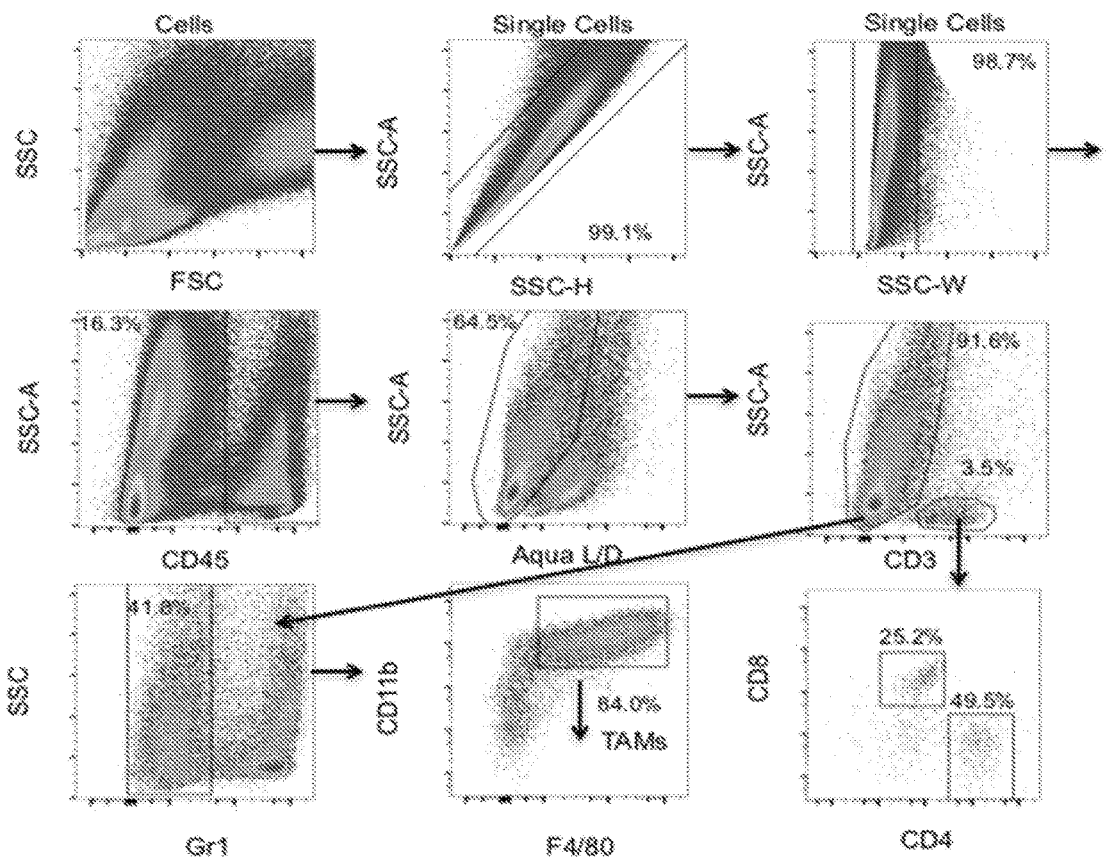
FIGS. 15A-15C are pictorial and graphical diagrams showing effects of LA1 on breast tumor progression.
Figure 15B:
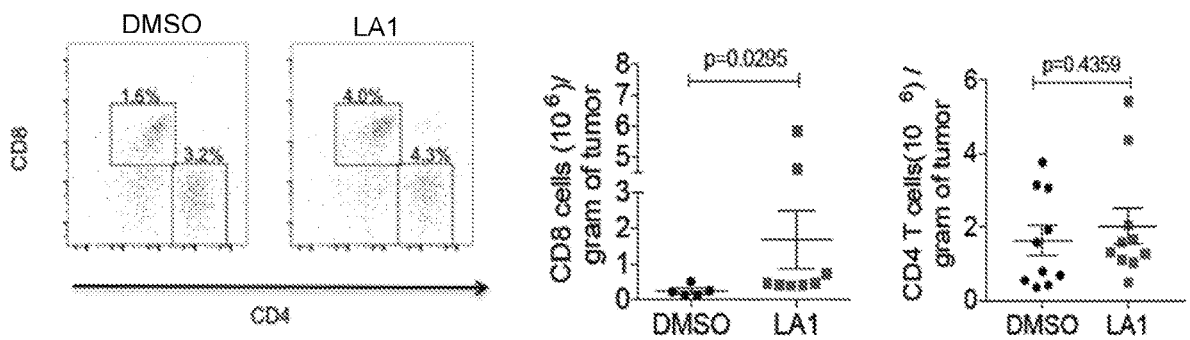
Figure 15C:
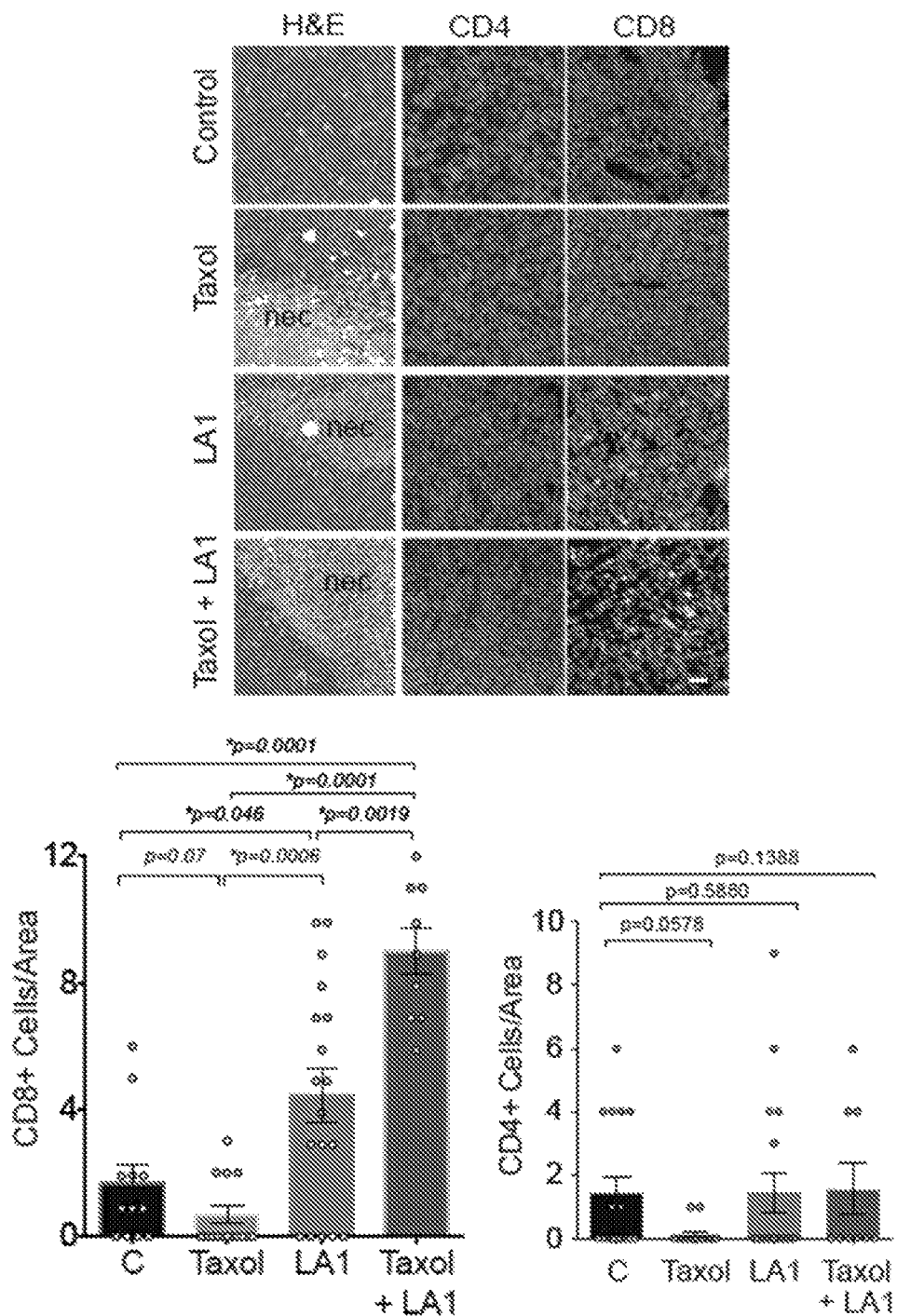

As LA1 treatment increased the presence of MHCII+ macrophages, typically considered immune suppressive, in LLC and CL66-Luc tumors (FIGS. 14C-14D), these studies suggest that LA1 repolarizes tumor associated macrophages. It was found that LA1 inhibited expression of S100A8 and MMP9 in CD11b+ cells in LLC tumors and also inhibited expression of Arginase1, S100A8 and MMP9 in CL66-Luc tumors (FIGS. 14E-14F). As these proteins are markers of pro-tumoral macrophages, together these studies indicate that LA1 likely inhibits tumor growth by repolarizing tumor associated macrophages. Indeed, LA1 treatment increased the presence of CD8+ T cells in both LLC and CL66-Luc tumors (FIGS. 15A-15C). It was also observed that LA1 treatment altered neovascularization in tumors by decreasing the numbers of SMA+blood vessels (FIG. 5L). By enhancing the pro-inflammatory immune profile of tumors and inhibiting vascular normalization in tumors, the small molecule CD11b agonist LA1 significantly altered macrophage polarization, increased CD8+ T cell recruitment to tumors and inhibited tumor progression in mouse models of murine and human cancer.

As described above, macrophage integrin CD11b was identified as a critical regulator of pro-inflammatory immune responses that prevent cancer progression. These studies demonstrate that CD11b ligation/activation inhibits the immune suppressive transcriptional signature of tumor-derived macrophages, stimulates accumulation of CD8+ T cells in tumors and suppresses tumor growth. Loss of CD11b expression or function promotes immune suppressive gene expression in macrophages in vitro and TAMs in vivo, increases FoxP3+CD4+ T cells and decreases CD8+ T cell recruitment to tumors and increases tumor growth. In contrast, activation of CD11b with the small molecule agonist LA1 stimulates macrophage pro-inflammatory transcription and anti-tumor immunity to inhibit tumor progression in animal models of cancer.

Using Itgam−/− mice, as well as knockdown and neutralizing antibody approaches, the data presented herein demonstrates that integrin CD11b is not required for myeloid cell trafficking during tumor growth, although other studies have shown CD11b regulates myeloid cell recruitment under conditions of acute inflammation.[17,18] These differences may arise from the unique microenvironmental cues and alterations in blood vessel biology observed in tumors versus inflamed tissue. Recent studies have shown that signaling pathways regulated by TLRs, CSF1R, PI3Kγ and BTK control macrophage polarization. Here, CD11b has been shown to promote miRNA Let7a and inhibit Myc expression to control macrophage polarization and tumor immune responses (FIG. 5M). Taken together, these studies demonstrate that agonists of macrophage integrin CD11b could provide benefit in the treatment of cancer.

Improved vascular perfusion in CD11b−/− animals was observed. Compared to non-pathological tissue, tumors display disorganized, and immature blood vessel structures. Tumor blood vessels often consist only of a single fenestrated endothelial layer and lack the additional coverage of mesenchymal cells, such as pericytes and smooth muscle cells, which provide blood vessels with a stable and more mature structure that promotes tumor perfusion and better access to chemotherapy[23-36]. In these studies, tumor blood vessels from CD11b−/− mice displayed increased pericyte coverage and increased vascular flow compared to WT. Indeed, deletion of CD11b or Let7a suppression increased the PDGF-BB/VEGF-A ratio, resulting in tumors with normalized vessels that stimulate tumor growth but are susceptible to cancer chemotherapy.

Integrin CD11b−/− macrophages expressed increased levels of IL-6 that induced the expression of STAT3-dependent immunosuppressive cytokines. Decreased integrin CD11b expression or activation negatively regulated the expression of miRNA Let-7a in macrophages, thereby upregulating intracellular Il6 levels in macrophages. Reduced Let-7a expression is associated with malignant transformation of cancer cells and poor prognosis in cancer[40,41]. It was found that loss of CD11b down-regulates Let7a, leading to elevated Il6 levels and increased activation of STAT3, which were critical for the expression of M2-related cytokines. In contrast, recent studies showed that miRNA Let 7d-5p and DICER promote the M2 phenotype[42]. Together, these studies demonstrate the critical roles that miRNA species play in the polarization of macrophages and cancer growth.

As demonstrated herein, loss of Let7 expression in CD11b−/− macrophages induces Myc expression; Myc then drives immune suppressive transcription and inhibition of immune stimulatory transcription. Although both Myc and NFκB are transiently activated in WT IFNγ/LPS stimulated macrophages, NFκB activation is inhibited and Myc is activated in IFNγ/LPS stimulated Itgam−/− macrophages, leading to blockade of immune stimulatory transcription. These results suggest that Myc may inactivate NFκB in macrophages, thereby contributing to immune suppression and enhanced tumor growth.

As discussed above, it was found that LA1, a potent activator of integrin CD11b/CD18 in vitro and in vivo[42], could significantly alter macrophage polarization, increase CD8+ T cell recruitment to tumors, inhibit tumor progression and prolong survival in mouse models of cancer. To determine the role of macrophage CD11b activation in tumor growth, adoptive transfer of LA1 treated macrophages was performed; LA1 treated macrophages directly and robustly inhibited tumor growth. LA1 effects were lost in Itgam−/− mice, indicating that the effects of LA1 on tumor growth depend on intact CD11b. These results indicate that LA1 acts on myeloid cells to effect changes in macrophage polarization, vasculogenesis and T cell recruitment. As LA1 has also been shown to inhibit bone marrow derived cell trafficking to tissues by promoting stable adhesion to endothelium. It is possible that LA1 may inhibit immune suppressive myeloid cell trafficking to tumors[49]. By slowing tumor progression, LA1 may also be useful to suppress the spread of cancer through metastasis.

LA1 was shown to stimulate a pro-inflammatory phenotype in macrophages in vitro and in vitro. To address the direct impact of LA1 treated TAMs on tumor growth, we performed adoptive transfer of LA1 treated TAMs with tumor cells. It was found that LA1 treatment of TAMs robustly and rapidly abolished tumor growth. In this model, it was previously shown that adoptive transfer of immune suppressive macrophages (IL-4 stimulated) or TAMs promotes tumor growth, while adoptive transfer of immune stimulatory macrophages (IFNγ/LPS stimulated) and repolarized TAMs) recruited CD8+ T cells to tumors and rapidly abolished tumor growth[10]. It was further shown that this tumor suppression by adoptively transferred macrophages required IL-12, a pro-inflammatory factor that recruits and stimulates CD8+ T cell proliferation[10]. Thus, this evidence supports that LA1 repolarizes TAMs, leading to recruitment and activation of CD8+ T cells. As systemic delivery of LA1 also recruits CD8+ T cells and repolarizes TAMs in tumor models, these studies indicate that CD11b agonism by LA1 repolarizes macrophages and stimulates an adaptive immune response.

The role of T cell depletion was tested in the response to LA1 treatment by implanting MDA-MB-231 breast tumor cells in SCID mice, which lack T cells. By comparison, CL66 Luc breast tumor cells were implanted in syngeneic, immune competent mice. Interestingly, LA1 inhibited MDA-MB-231 tumor growth to 50% of that of control treated animals. In contrast, LA1 inhibited CL66 Luc tumor growth to 25% of that of control tumors. LA1 also repolarized macrophages by stimulating MHCII expression and reducing CD206, Arg1, MMP9 and S100A8 expression in TAMs and promoted CD8+ T cell recruitment in this model. Together, these results indicate that LA1 acts on myeloid cells to change tumor associated macrophage polarization leading to increased T cell recruitment, and T cell dependent tumor suppression.

However, the partial effect of LA1 on MDA-MB-231 tumors indicates that LA1 (and hence CD11b) also affects T cell independent processes to suppress tumor growth. It was shown that LA1 reduced inhibiting vascular normalization (as detected by pericyte coated blood vessel density) in all tumor models. These studies indicate that CD11b controls innate immune cell polarization and that these cells regulate vascular as well as adaptive immune responses in the tumor microenvironment. Together, these results indicate that CD11 activation controls tumor macrophage polarization, vasculogenesis and T cell recruitment.

In yet another aspect, the invention provides a method of identifying cancer cells amenable to treatment with a chemotherapeutic agent. The method includes detecting expression levels of CD11b or Let7a, alone or in combination with one or more of Il1b, Tnfa, Il12, Nos2 and Ifng in a sample comprising cancer cells from the subject, contacting the sample with an agonist of CD11b or Let7a activity or expression, and detecting increased levels of CD11b or Let7a, thereby identifying the cancer cells as being amenable to treatment with a chemotherapeutic agent. The method may further include detecting increases in expression of Il1b, Tnfa, Il12, Nos2 and Ifng to further support the finding that the cancer cells as being amenable to treatment with a chemotherapeutic agent. In various embodiments, the method may further include detecting expression levels of one or more of Pdgfb and Il6 prior to the contacting, where inhibited Pdgfb and Il6 expression after the contacting is indicative of the cancer cells are amenable to treatment with a chemotherapeutic agent.

In yet another aspect, the invention provides a method of rendering a cancer cell susceptible to a cancer therapeutic treatment regimen. The method includes contacting the cancer cell with an agonist of CD11b or Let7a activity or expression, thereby rendering the cancer cell susceptible to the cancer therapeutic treatment regimen.

In another aspect, the invention provides a composition comprising the agonist of CD11b or Let7a activity or expression of the invention, which can be prepared for administration to a subject by mixing the agonist with physiologically acceptable carriers or excipients. Such carriers will be nontoxic to recipients at the dosages and concentrations employed. Ordinarily, the preparation of such compositions entails combining the particular antibody with saline, buffers, antioxidants such as ascorbic acid, low molecular weight (less than about 10 residues) polypeptides, proteins, amino acids, carbohydrates including glucose or dextrans, or chelating agents such as EDTA, glutathione and other stabilizers and excipients. Such compositions can be in suspension, emulsion or lyophilized form and are formulated under conditions such that they are suitably prepared and approved for use in the desired application.

A physiologically acceptable carrier or excipient can be any material that, when combined with the agonist of CD11b or Let7a activity or expression of the invention, allows the ingredient to retain biological activity and does not undesirably disrupt a reaction with the subject's immune system. Examples include, but are not limited to, any of the standard physiologically acceptable carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, Chapter 43, 14th Ed., Mack Publishing Co., Easton Pa. 18042, USA).

For administration to a subject, a peptide, or an encoding polynucleotide, generally is formulated as a composition. Accordingly, the present invention provides a composition, which generally contains, in addition to the peptide or polynucleotide of the invention, a carrier into which the peptide or polynucleotide can be conveniently formulated for administration. For example, the carrier can be an aqueous solution such as physiologically buffered saline or other solvent or vehicle such as a glycol, glycerol, an oil such as olive oil or an injectable organic ester. A carrier also can include a physiologically acceptable compound that acts, for example, to stabilize the peptide or encoding polynucleotide or to increase its absorption. Physiologically acceptable compounds include, for example, carbohydrates, such as glucose, sucrose or dextrans, antioxidants, such as ascorbic acid or glutathione, chelating agents, low molecular weight proteins or other stabilizers or excipients. Similarly, a cell that has been treated in culture for purposes of the practicing the methods of the invention also can be formulated in a composition when the cells are to be administered to a subject.

In another aspect, the invention provides a method of screening for a therapeutic/test/candidate agent for treating cancer or for promoting tumor perfusion and better access to chemotherapy. The method includes administering a test agent to the transgenic non-human mammal described herein and evaluating the effect of the test agent on at least one of expression levels of CD11b or Let7a, alone, or in combination with one or more of Il1b, Tnfa, Il12, Nos2 and Ifng in at least one disease-relevant tissue of the transgenic non-human mammal, wherein at least one of: an increase in the amount of CD11b expression or an increase in the amount of Let7a expression, alone, or in combination with increases in expression of Il1b, Tnfa, Il12, Nos2 and Ifng in at least one disease-relevant tissue relative to a similar transgenic non-human mammal that does not receive the test agent indicates the test agent is therapeutic for the cancer and/or promotes tumor perfusion and better access to chemotherapy.

A "test agent" or "candidate agent" refers to an agent that is to be screened in one or more of the assays described herein. The agent can be virtually any chemical compound. It can exist as a single isolated compound or can be a member of a chemical (e.g., combinatorial) library. In one embodiment, the test agent is a small organic molecule. The term small organic molecules refers to molecules of a size comparable to those organic molecules generally used in pharmaceuticals.

Conventionally, new chemical entities with useful properties are generated by identifying a chemical compound (called a "lead compound") with some desirable property or activity, creating variants of the lead compound, and evaluating the property and activity of those variant compounds.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the plasma expander used to treat blood loss in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The following examples are intended to illustrate but not limit the invention.

EXAMPLE 1

Materials and Methods

Cell lines—C57BL/6 LLC, B16 melanoma, CL66 breast and MDA-MB-231 breast tumor cells were obtained from the American Type Culture Collection (ATCC). Cells were cultured in antibiotic- and fungizide-free DMEM or RPMI media containing 10% serum and tested negative for mycoplasma using the Mycoplasma Plus PCR primer set from Stratagene (La Jolla, Calif.). All cell lines were authenticated by tumor cell and tumor histology and by RNA or DNA sequencing.

Mice—C57BL/6 and CD11b deficient (Itgam$^{-/-}$) mice in the C57BL/6 background were from Jackson Laboratories. For the spontaneous breast cancer model, male PyMT+ mice on a C57BL/6 background were crossed with wild type (WT) or Itgam$^{-/-}$ C57BL/6 at the University of California, San Diego to generate WT and Itgam$^{-/-}$ P+ females. Wild type and CD11b$^{-/-}$ female mice heterozygous for the PyMT transgene were compared to each other. All PyMT+ females exhibit adenomas/early carcinomas by 16 weeks of age and late carcinomas by 25 weeks of age.

Generation of the ITGAM I332G knock-in mouse was accomplished by replacing exon 9 of the ITGAM gene using a targeting construct in which the Ile332 codon was substituted with Gly using a site-directed mutagenesis kit. The mutation led to the loss of the Exon-9 Bgl II restriction site. C57BL/6 ES cells with the heterozygous ITGAM I332G mutant allele were generated. G418-resistant clones were characterized by PCR, sequencing and southern blot analysis. The heterozygous mutant mice were generated using the blastocyst injection method. Mice heterozygous for the ITGAM I332G mutation were normal, fertile and phenotypically indistinguishable from wild-type (WT) littermates. The heterozygous mice were bred with ROSA26::FLPe knockin (JAX Stock No: 003946) mice to remove the selection cassette. The N2 offspring were backcrossed with C57BL/6N for six generations. The C57BL/6N N6 mice were crossed to obtain mice homozygous for the ITGAM I332G mutation that were also indistinguishable from wild-type (WT) littermates. Female nude and Balb/cJ mice at 6-8 weeks of age were from Jackson Laboratories and housed under pathogen-free conditions in the animal facility at Rush University Medical Center.

Tumor Studies—Subcutaneous tumor studies: 5×10$^5$ LLC or B16 cells were injected subcutaneously into syngeneic (C57BL/6) 6- to 8-week old WT or Itgam$^{-/-}$ mice (n=18). Tumors were excised at 7, 14 or 21 days, cryopreserved in OCT, lysed for RNA purification or collagenase-digested for flow cytometric analysis of CD11b+, F4/80+ and Gr1+ expression. Tumor volumes were calculated using the equation (l$^2$×w)/2. CL66-luc cells (0.5×10$^6$ cells) were suspended in 50 µL of basement membrane extract Matrigel (BD Pharmingen) in PBS (1:1) and inoculated orthotopically in the fourth mammary fat pad of female Balb/cJ mice. Tumor dimensions were measured every 2 days, and tumor volume was calculated using the equation: V (mm$^3$)=n/6 (length)* (width), where length is the longest diameter of the tumor and width is the shorter diameter.

Mice were divided into four cohorts: vehicle control treated, LA1 only treated, Taxol only treated, LA1 and Taxol treated. LA1 (2 mg/kg) was dissolved in 2% DMSO and 1% Tween-20 in saline and Taxol (2.5 mg/kg) was dissolved in a 1:1:6 ratio of Cremophor EL: Ethanol:Saline. LA1 was administered by intraperitoneal injection (i.p.) daily, while Taxol was administered every other day by i.p. injection until end-point. LA1+Taxol treated mice received LA1 i.p. in the morning followed by Taxol i.p. within 4 hours. Tumor burden was evaluated every other day by caliper measurements. Prior to tissue collection, mice were anesthetized by ketamine/xylazine and the lungs were perfused with PBS followed by 10% formalin and harvested for fixation. Mammary tumor tissue was harvested and divided for fixation (10% formalin or OCT), snap frozen, or made into single-cell suspensions and analyzed by flow cytometric analysis. For survival studies, Balb/c mice bearing CL66-derived tumors were treated for 6 weeks after the first treatment and monitored thereafter. End point was considered when the tumor reached 2 mm in diameter (n=10-15).

Alternatively, 5 million MDA-MB 231 human breast cancer cells were injected orthotopically in the 4th mammary fat pad of 6-week old female nude mice. The tumors were allowed to establish for 35 days (at least 0.5 cm in diameter) and the tumor bearing mice were divided into three treatment groups including, vehicle, LA1 only (i.p.; 2.0 mg/kg; daily) and Taxol only (i.p.; 2.5 mg/kg every other day). Treatment was initiated on day 35 and continued until the end-point at day 58 post-tumor when all the mice were sacrificed and tumor tissue was harvested for histological analysis. Palpable tumors were measured using digital calipers 3 times weekly during the entire experiment to develop tumor growth curves.

LA1 treatment of LLC: 7.5×10$^5$ LLC cells were injected subcutaneously (s.c.) into the right flank of syngeneic 6- to 8-week old WT or CD11b$^{-/-}$ mice. At 5-8 days post tumor inoculation, tumor-bearing mice were divided into the following treatment groups: Vehicle (6% DMSO, 1% Tween-20 in saline), LA1 (6 mg/kg dissolved in vehicle). Vehicle and LA1 was administered by intraperitoneal injection (i.p.) daily. Tumor burden was evaluated 2-3 times a week by caliper measurements and tumor volumes were calculated using the equation (l$^2$×w)/2. Tumors were harvested at 3 weeks post-tumor inoculation, formalin fixed, cryopreserved in OCT, or collagenase-digested for flow cytometric analysis.

PyMT Studies: The growth of spontaneous mammary tumors in PyMT+(n=10) and Itgam$^{-/-}$; PyMT+(n=14) animals in the C57Bl6 background was evaluated over the course of 0-25 weeks. All PyMT+ females exhibited adenomas/early carcinomas by 16 weeks of age and late carcinomas by 25 weeks of age. Total tumor burden at endpoint was determined by subtracting the total mammary gland mass in PyMT-animals from the total mammary gland mass in PyMT+ animals.

ITGAM I332G knock-in mouse tumor studies: $7.5 \times 10^5$ LLC cells were injected subcutaneously (s.c.) into the right flank of syngeneic 6- to 8-week old WT or CD11b KI mice. Palpable tumors were established at 5-8 days post-tumor inoculation. Tumor burden was evaluated 2-3 times a week by caliper measurements and tumor volumes were calculated using the equation $v=(l^2 \times w)/2$. Tumors and spleens were harvested at 4 weeks post-tumor inoculation, weighed, formalin fixed or cryopreserved in OCT for histological analysis.

Immunohistochemistry—Tumor samples were collected and cryopreserved in O.C.T. Sections (5 μm) were fixed in 100% cold acetone, blocked with 8% normal goat serum for 2 hours, and incubated with primary antibodies at 1-5 μm/ml for 2 hours at room temperature. Sections were washed 3 times with PBS and incubated with fluorescent secondary antibodies. Primary antibodies where: F4/80 (BM8, eBioscience), CD4 (H129.19, BD Bioscience), CD8 (53-6.7, BD Bioscience), CD31 (MEC13.1, BD Bioscience), desmin (RB0914-P1, LabVision, Thermo Scientific), and anti-smooth muscle actin (SMA) (1A4, Sigma-Aldrich). Slides were counterstained with 4',6-diamidino-2-phenylindole (DAPI) to identify nuclei. Immunofluorescence images were collected on a Nikon microscope (Eclipse TE2000-U) and analyzed using Metamorph image capture and analysis software (Version 6.3r5, Molecular Devices). Pixels/field or cell number/field were quantified in five 100× fields from 5 biological replicates. For LA1 studies, immunohistochemical staining was quantified by counting marker positive cells in 3 different areas analyzed at 40× using a light microscope for each tumor tissue (n=4-6). Tissues that were stained with fluorochrome conjugated secondary antibodies were counter stained with DAPI and analyzed using the Zeiss 700 LSM confocal microscope and Zen software (Carl Zeiss Group, Hartford, Conn.).

Alternatively, immunostaining was performed on formalin fixed, paraffin-embedded tumor tissues. Deparaffinized tissue sections (5 μm) were either stained with hemotoxylin-eosin or were subjected to antigen retrieval by steam heating in an acidic pH solution (Citrate-based, Vector Laboratories) prior to immune staining for α-SMA (clone 1A4, Fisher Scientific), MMP9 (polyclonal rabbit, Abcam), S100A8 (goat polyclonal (M-19), Santa Cruz), CD31 (clone RM0032-1D12, Abcam), or ARG1 (sc-18351, Santa Cruz) at 4° C. overnight. Sections were washed and incubated with the appropriate fluorochrome conjugated secondary antibody (Invitrogen Life Technologies, Grand Island, N.Y.) or biotinylated secondary antibodies diluted in blocking buffer for 1 hr. at RT. For sections that were stained with biotinylated secondary antibodies, signal development was accomplished by using the DAB Substrate Kit (Vector Laboratories).

Quantification of Murine Peripheral Blood Cells—To quantify myeloid cells in murine peripheral blood, blood was collected from naïve or tumor bearing mice by retro-orbital bleeding into heparin-coated Vacutainer tubes (BD Bioscience), incubated in red blood cell lysis buffer. Cells were washed twice in PBS and stained for flow cytometric sorting.

Cytotoxicity Assay—Taxol and LA1 cytotoxicity towards the CL66-luc tumor cell was determined by measuring luciferase activity in the tumor cells after exposure to LA1 or Taxol. CL66-luc cells (1,000 cells/well) were seeded into 96-well plates overnight at 37° C. prior to treatment with titrating concentrations of LA1 or Taxol dissolved in 1% DMSO in IDMEM for 24, 48 and 72 hrs. Cells treated with vehicle (1% DMSO in IDMEM) were a negative control. Media was aspirated from the cultured cells and 100 μL of a 150 μg/mL working solution of D-Luciferin in pre-warmed DMEM (10% FBS) was added to each well. The plates were incubated at 37° C. for 5 mins prior to reading luminescence using the EnSpire Plate Reader (PerkinElmer).

Isolation of Single Cells from Murine Tumors—Tumors were isolated, minced in a petri dish on ice and then enzymatically dissociated in Hanks Balanced Salt Solution containing 0.5 mg/ml Collagenase IV (Sigma), 0.1 mg/ml Hyaluronidase V (Sigma), and 0.005 MU/ml DNAse I (Sigma) at 37° C. for 5-30 min. The duration of enzymatic treatment was optimized for greatest yield of live CD11b+ cells per tumor type. Cell suspensions were filtered through a 70 μm cell strainer. Red blood cells were solubilized with red cell lysis buffer (Pharm Lyse, BD Biosciences, San Jose, Calif.), and the resulting suspension was filtered through a cell strainer to produce a single cell suspension. Cells were washed one time with PBS prior to use in flow cytometry analysis or sorting.

Flow Cytometry Staining and Analysis—Single cell suspensions ($10^6$ cells in 100 μL total volume) were incubated with Aqua Live Dead fixable stain (Life Technologies, Carlsbad, Calif.), FcR-blocking reagent (BD Biosciences, San Jose, Calif.) and fluorescently labeled antibodies and incubated at 4° C. for 1 h. Primary antibodies were: BV605-F4/80 (clone BM8, Biolegend #123133, 1.25 μg/ml), Alexa 700-CD45 (clone 30-F11, eBioscience #56-0451, ×0.6 μg/ml), CD11b-APC (clone M1/70, eBioscience #17-0012, 0.3 μg/ml), FITC-Gr1 (clone RB6-8C5, eBioscience #11-5931, 3 μg/ml), eF780-CD3 (clone 145-2C11, eBioscience #47-0031, 5 μg/ml), PE-Dazzle-CD4 (clone RM4-5, Biolegend #100565, 0.4 μg/ml), and BV605-CD8 (clone 53-6.7, Biolegend #100743, 1.75 μg/ml). Multicolor FACS Analysis was performed on a BD Canto RUO 11 Color Analyzer. All data analysis was performed using the flow cytometry analysis program FloJo (Treestar).

Human Macrophage Differentiation and Culture—Human leukocytes concentrated by from apheresis were obtained from the San Diego Blood Bank. Cells were diluted in phosphate buffered saline (PBS), 0.5% BSA, 2 mM EDTA, incubated in red cell lysis buffer (155 mM $NH_4Cl$, 10 mM $NaHCO_3$ and 0.1 mM EDTA) and centrifuged over Histopaque 1077 to purify mononuclear cells. Approximately $10^9$ cells were purified by gradient centrifugation from one apheresis sample. Purified mononuclear cells were cultured in RPMI+20% serum+50 ng/ml Human M-CSF (PeproTech). Non-adherent cells were removed after 2 hours by washing, and adherent cells were cultured for 6 days to differentiate macrophages fully.

Murine macrophage differentiation and culture—Bone marrow derived cells (BMDC) were aseptically harvested from 6-8 week-old female mice by flushing leg bones of euthanized mice with phosphate buffered saline (PBS), 0.5% BSA, 2 mM EDTA, incubating in red cell lysis buffer (155 mM $NH_4Cl$, 10 mM $NaHCO_3$ and 0.1 mM EDTA) and centrifuging over Histopaque 1083 to purify the mononuclear cells. Approximately $5 \times 10^7$ BMDC were purified by gradient centrifugation from the femurs and tibias of a single mouse. Purified mononuclear cells were cultured in RPMI+ 20% serum+50 ng/ml M-CSF (PeproTech).

Macrophage Polarization—Bone marrow derived macrophages were polarized with either IFNγ (20 ng/ml, Peprotech) plus LPS (100 ng/ml, Sigma) or LPS alone for 24 h or IL-4 (20 ng/ml, Peprotech) for 24-48 h. In some cases, macrophages were incubated with inhibitors of Stat3 (STAT4 VIII) or cMyc (10058-F4, Selleck). In other experiments, BMM were treated with LLC tumor conditioned media (TCM) or 100 ng/ml TGF-β (PeproTech) for 6 h to analyze changes in protein and gene expression levels. TCM was obtained by culturing LLC in serum free media for 18 h followed by collecting the supernatant and sterile filtering prior to use. In some experiments TGF-β signaling was inhibited using SB5253324 added 30 min prior and during the 6 h stimulation. Total RNA was harvested from macrophages using the RNeasy Mini Kit (Qiagen) according to the manufacturer's instructions. Secreted protein was measured in culture supernatants by ELISA assays.

Cell Adhesion Assay— PBMCs were extracted from human whole blood using the vendor instructions for Sep Mate-50 tubes (#15450, Stem Cell). Human CD14+ monocytes were isolated from the PBMCs using the vendor instructions for the EasySep™ Human Monocyte Isolation Kit (Catalog #19359, Stem Cell). Briefly, 384-well plates (#3700, Corning) were coated with recombinant human ICAM1 (750 ng/mL, #720-IC, R&D Systems), or M1/70 (10 ug/mL, #101202, Biolegend) or IB4 (10 µg/mL, #167-020, Ancell) overnight at 4° C. Wells were blocked with 1% milk dissolved in TBS for 1 hr at room temperature. All wells received $Ca^{2+}/Mg^{2+}$ ions (1 mM each physiological concentration, baseline control) except for the positive control wells that received 1 mM $Mn^{2+}$ ions. A stock solution of LA1 agonist was prepared by dissolving the compound in DMSO at a concentration of 2 mM and final dilution of LA1 in wells was 20 µM. The final concentration of DMSO in all wells was 1%. 45,000 human monocytes were seeded in each well. Some wells received human monocytes cells that were pre-blocked with anti-human CD11b (M1/70) for 15 min at 4° C. The plates were incubated at 37° C. for 30 min followed by 30 min of inversion at room temperature to remove non-adherent cells. Cells were fixed, stained with DAPI and counted using the Opera High Content Screening System (Perkin Elmer). Assays were performed in six replicate wells.

Lentiviral Transduction of Bone Marrow Derived Macrophages—Self-inactivating pLenti vectors containing CD11b WT, CD11b I332G active and CD11b E336A inactive variants were obtained. Expression of CD11b in these vectors is driven by CMV promoter. HEK 293T cells were used as packaging cells to produce VSV-G pseudotyped lentiviral particles. Viral titer was assessed by qPCR for p24 viral RNA and was in the order of $1\times10^8$ IU/ml. $2\times10^6$ bone marrow derived mononuclear cells were plated per well in 6-well non-tissue culture treated plates in DMEM media supplemented with 20% FBS, 1% Pen Strep and 50 ng/ml M-CSF, in the presence of various lentivirus. On day 2 and day 4, fresh DMEM containing 20% FBS, 1% Pen Strep and 50 ng/ml M-CSF was added to the cells. On day 7, the cells were lifted from the plate using 5 mM EDTA in PBS and stained for flow cytometry using Aqua-live/dead, F4/80-APC and CD11b-PE antibodies or used in further studies.

Analysis of Gene Expression—Total RNA was isolated from cells using RNeasy Mini Kit (Qiagen). cDNA was prepared using 1 µg RNA with the qScript cDNA Synthesis Kit (Quanta Biosciences) or the SuperScript III First-Strand Synthesis Kit (Invitrogen). Sybr green-based qPCR was performed using primers to murine Gapdh (Mm_Gapdh_1_SG), Arg1 (Mm_Arg_1_SG_QT00134288) Tgfb (Mm_Tgfb_1_SG Qiagen QT00145250), 1110 (Mm_Il10_1_SG Qiagen QT00106169), Il6 (Mm_Il6_1_SG Qiagen QT00098875), Nos2 (Mm_Nos2_1_SG Qiagen QT00100275), Il12b (Mm_Il12b_1_SG Qiagen QT00153643), Ifng (Mm_Ifng 1_SG Qiagen QT01038821), Il1b (Mm_Il1b_2_SG Qiagen QT01048355), Tnfa (Mm_Tnfa_1_SG Qiagen QT00104006), Vegfa (Mm_Vegfa_1_SG Qiagen QT00160769), Pdgfb (Mm_Pdgfb_1_SG Qiagen QT00266910) and human GAPDH (Hs_GAPDH_1_SG Qiagen QT00079247), ARG1 (Hs_Arginase_1_SG Qiagen QT00068446, IL6 (Hs_Il6_1_SG Qiagen QT00083720), NOS2 (Hs_NOS2_1_SG Qiagen QT00068740), IL12B (Hs_IL12B_1_SG Qiagen QT00000364), and PDGFB (Hs_PDGFB_1_SG Qiagen QT00001260) (Qiagen QuantiTect Primer Assay). mRNA levels were normalized to Gapdh or GAPDH (ΔCt=Ct gene of interest—Ct Gapdh) and reported as relative mRNA expression (ΔΔCt= $2^{-(\Delta Ct\ sample - \Delta Ct\ control)}$) or fold change.

Immunoblotting—IL-4 and LPS macrophage cultures were solubilized in RIPA buffer containing protease and phosphatase inhibitors. 30 µg protein was electrophoresed on Biorad precast gradient gels and electroblotted onto PVDF membranes. Proteins were detected by incubation with 1:1000 dilutions of primary antibodies, washed and incubated with Goat anti-rabbit-HRP antibodies and detected after incubation with a chemiluminescent substrate. Primary antibodies directed against NFκBp65 (D14E12, #8242 Cell Signaling Technology, 1:1000), pSer536NFκBp65 (93H1, #3033 Cell Signaling Technology, 1:1000), cMyc (D3N8F, #13987 Cell Signaling Technology, 1:1000) or pSer62 cMyc (E1J4K, #13748 Cell Signaling Technology, 1:1000). Anti-actin (#A2103 Sigma-Aldrich, 1:1000).

ELISA Assays—Macrophage supernatants (100 µl) were used in ELISAs to detect CCLS, TNFα, and IL-6 (Ready Set Go ELISA, ThermoFisher). Protein expression was normalized to total volume (supernatants).

In vivo Macrophage Adoptive Transfer Experiments—F4/80+ cells were isolated from single cell suspensions of 700-800 mg LLC tumors from donor WT or Itgam-/- mice by FACS sorting. Primary bone marrow derived macrophages from WT or Itgam-/- mice were polarized and harvested into a single cell suspension. Alternatively, WT tumor derived macrophages were incubated with LA1 or saline. Purified macrophages were admixed 1:1 with LLC tumor cells and $5\times10^5$ total cells were injected subcutaneously into syngeneic host WT or Itgam-/- mice. Tumors were excised and weights were determined 14 days after inoculation.

Integrin CD11b Ligation Experiments—Differentiated bone marrow derived macrophages were cultured on 5 µg/ml VCAM-1 or ICAM-1 (R&D Systems) coated culture plates or maintained in suspension. To inhibit integrin CD11b ligation, macrophages were cultured on 5 µg/ml ICAM-1 in the presence of 25 µg/ml anti-CD11b antibody (M1/70, BD Bioscience) or in suspension culture on BSA coated culture plates. As a control, macrophages were cultured in the presence of IgG control antibody.

siRNA Mediated Knockdown—Differentiated macrophages were transfected (AMAXA, Mouse Macrophage Nucleofection Kit) using 100 nM of siRNA against Itgam (Mm_Itgam_01 or Mm_Itgam-5), Il6 (Mm_Il6_01 or Mm_Il6_03) or non-silencing siRNA (Ctrl_AllStars_1) from Qiagen. After transfection, cells were cultured for 36-48 h in DMEM containing 10% serum and 10 ng/ml M-CSF (PeproTech). Efficiency of Itgam knockdown of each oligo was confirmed by quantitative RT-PCR Quanti-Tect Primer Assay) and flow cytometry.

MicroRNA and Anti-microRNA—Control miRNA, control anti-miRNA, Pre-miR-Let7a (PM10050) and Anti-miR-Let7a (AM10050) for in vitro studies were from Applied Biosystems. MicroRNA was delivered using siPORT (Ambion). To evaluate microRNA expression levels, total RNA was extracted with Trizol (Invitrogen), and RT-PCR was performed to detect let-7a(Mm_let-7a-1_2), let 7d (Mm_let-7d_1), or let7f (Mm_let7f-1_1) miScript Primer Assay. Data were normalized to the internal control small RNA snoRNA202 (Applied Biosystems). For in vivo studies, oligomers were purchased from Sigma:

```
Anti-miR scrambled control:
5'-[mG][mU][mC][mA][mA][mG][mG][mC][mA][mU][mC]
[mC][mG][mG][mA][mU][mC][mA][mU][mC][mA][mA]-3'

Anti-miR-Let7a:
5'-[mA][mC][mU][mC][mC][mA][mU][mC][mA][mU][mC]
[mC][mA][mA][mC][mA][mU][mA][mU][mC][mA][mA]-3'
```

Nanoparticle Preparation and Administration—The cyclic peptides, cRGDfK and cRADfK, were synthesized by using standard Fmoc solid-phase chemistry. Peptides were purified by reverse-phase HPLC, and mass was confirmed by mass spectroscopy. Peptides were conjugated to succinimidyl ester-(PEO)$_4$-maleimide (Pierce). DSPE was reacted with iminothiolane (Sigma-Aldrich) to produce a free thiol. The DSPE containing the free thiol group was reacted with the cRGDfK-(PEO)$_4$-maleimide or cRADfK-(PEO)$_4$-maleimide to produce peptide-lipid conjugates.

Cholesterol/DOPE/DSPC/DSPE-(PEO)$_4$-cRGDfK/DSPE-mPEG2000 (6:6:6:1:1 molar ratio) in chloroform was evaporated under argon gas and then hydrated in sterile 300 mM ammonium phosphate buffer (pH 7.4) at a total lipid concentration of 3.32 mM for 1 h. Liposomes were vortexed for 2-3 min and sonicated in ULTRAsonik 28×for 2-3 min at room temperature to produce multilamellar vesicles (MLVs). MLVs were then sonicated with a Ti-probe (Branson 450 sonifier) for 1-2 min to produce small unilamellar vesicles (SUVs). Stepwise extrusion was performed with the final step being extrusion through a polycarbonate filter with 100-nm pore size (Whatman). Liposomes incorporating cyclic peptides were used to form lipid-RNA complexes. These complexes were formulated with a molar ratio of 4:1 calculated based on the N-[1-(2,3-dioleoyloxy)]-N,N,N-trimethylammonium propane (DOTAP) content of the liposomes. Nucleic acids (anti-miRNAs) and lipids were separately diluted in 100 µl RNase-free water. The RNA solution was added to the liposomes, mixed gently and the mixture was incubated at 25° C. for 5 min before injection into mice. Mice were treated with 5 µg of scrambled anti-miRNA or anti-miR-Let7a (Sigma) in RGD-nanoparticles intravenously every 3d starting from day 7 until the end of the experiment.

Statistics—For studies evaluating mutations or drug treatments on tumor size, tumor volumes were computed and mice were randomly assigned to groups so that the mean volume +/−s.e.m. of each group was identical. A sample size of 10 mice/group provided 80% power to detect mean difference of 2.25 standard deviation (SD) between two groups (based on a two-sample t-test with 2-sided 5% significance level). Significance testing was performed by one-way Anova with Tukey's posthoc testing for multiple pairwise testing or by parametric or nonparametric Student's t test as appropriate. A two-sample t-test (two groups) and ANOVA (multiple groups) were used when data were normally distributed, a Wilcoxon rank sum test (two groups) when data were not and Fisher's exact test when appropriate. All mouse studies were randomized and blinded; assignment of mice to treatment groups, tumor measurement and tumor analysis was performed by coding mice with randomly assigned mouse number, with the key unknown to operators until experiments were completed. In tumor studies for which tumor size was the outcome, animals removed from the study due to health concerns were not included in endpoint analyses.

References: the following references are hereby incorporated by reference in their entireties.

1. Quail, et al. Microenvironmental regulation of tumor progression and metastasis. Nat. Med. 19, 1423-1437 (2013).
2. Schmid, et al. Myeloid cells in tumor inflammation. Vasc. Cell 4, 14 (2012).
3. Sica, A. & Mantovani, A. Macrophage plasticity and polarization: in vivo veritas. J. Clin. Invest. 122, 787-795 (2012).
4. Gabrilovich, D.I. Myeloid-Derived Suppressor Cells. Cancer Immunol Res. 5, 3-8 (2017).
5. Cotechini, et al. Myeloid Cells as Targets for Therapy in Solid Tumors. Cancer J 21, 343-350 (2015).
6. Ruffell, B. & Coussens, L. M. Macrophages and therapeutic resistance in cancer. Cancer Cell 27, 462-472 (2015).
7. Chittezhath, M. et al. Molecular profiling reveals a tumor-promoting phenotype of monocytes and macrophages in human cancer progression. Immunity 41, 815-829 (2014).
8. Gunderson, A. J. et al. Bruton tyrosine kinase-dependent immune cell crosstalk drives pancreas cancer. Cancer Discov. 6, 270-285 (2016).
9. Kaneda, M. M. et al. Macrophage PI3Kgamma drives pancreatic ductal adenocarcinoma progression. Cancer Discov. 6, 870-885 (2016).
10. Kaneda, M. M. et al. PI3Kγ is a molecular switch that controls immune suppression. Nature 539, 437-442 (2016).
11. Pyonteck, S. M. et al. CSF-1R inhibition alters macrophage polarization and blocks glioma progression. Nat. Med. 19, 1264-1272 (2013).
12. Quail, D. F. et al. The tumor microenvironment underlies acquired resistance to CSF-1R inhibition in gliomas. Science 352, aad3018 (2016).
13. Schmid, M. C. et al. Combined blockade of integrin-alpha4beta1 plus cytokines SDF-1alpha or IL-1beta potently inhibits tumor inflammation and growth. Cancer Res. 71, 6965-6975 (2011).
14. Schmid, M. C. et al. PI3-kinase gamma promotes Rap1a-mediated activation of myeloid cell integrin alpha4beta1, leading to tumor inflammation and growth. PLoS One 8, e60226 (2013).
15. Schmid, M. C. et al. Receptor tyrosine kinases and TLR/IL1Rs unexpectedly activate myeloid cell PI3kγ, a single convergent point promoting tumor inflammation and progression. Cancer Cell 19, 715-727 (2011).
16. Coxon, A. et al. A novel role for the beta 2 integrin CD11b/CD18 in neutrophil apoptosis: a homeostatic mechanism in inflammation. Immunity 5, 653-666 (1996).
17. Jaeschke, H. et al. Functional inactivation of neutrophils with a Mac-1 (CD11b/CD18) monoclonal antibody protects against ischemia-reperfusion injury in rat liver. Hepatology 17, 915-923 (1993).

18. Rosetti, F. & Mayadas, T. N. The many faces of Mac-1 in autoimmune disease. Immunol. Rev. 269, 175-193 (2016).
19. Gilmore, T. D. Introduction to NF-kappaB: players, pathways, perspectives. Oncogene 25, 6680-6684 (2006).
20. Fan, S. T. & Edgington, T. S. Integrin regulation of leukocyte inflammatory functions. CD11b/CD18 enhancement of the tumor necrosis factor-alpha responses of monocytes. J. Immunol. 150, 2972-2980 (1993).
21. Ling, G. S. et al. Integrin CD11b positively regulates TLR4-induced signaling pathways in dendritic cells but not in macrophages. Nat. Commun. 5, 3039 (2014).
22. Xiong, J. P., Li, R., Essafi, M., Stehle, T. & Arnaout, M. A. An isoleucine-based allosteric switch controls affinity and shape shifting in integrin CD11b Adomain. J. Biol. Chem. 275, 8762-38767 (2000).
23. Abramsson, A., Lindblom, P. & Betsholtz, C. Endothelial and nonendothelial sources of PDGF-B regulate pericyte recruitment and influence vascular pattern formation in tumors. J. Clin. Invest. 112, 1142-1151 (2003).
24. Carmeliet, P. & Jain, R. K. Principles and mechanisms of vessel normalization for cancer and other angiogenic diseases. Nat. Rev. Drug Discov. 10, 417-427 (2011).
25. Greenberg, J. I. et al. A role for VEGF as a negative regulator of pericyte function and vessel maturation. Nature 456, 809-813 (2008).
26. Hellstrom, M. et al. Lack of pericytes leads to endothelial hyperplasia and abnormal vascular morphogenesis. J. Cell. Biol. 153, 543-553 (2001).
27. Lindahl, P., Johansson, B. R., Leveen, P. & Betsholtz, C. Pericyte loss and microaneurysm formation in PDGF-B-deficient mice. Science 277, 242-245 (1997).
28. Stockmann, C. et al. Deletion of vascular endothelial growth factor in myeloid cells accelerates tumorigenesis. Nature 456, 814-818 (2008).
29. Tong, R. T. et al. Vascular normalization by vascular endothelial growth factor receptor 2 blockade induces a pressure gradient across the vasculature and improves drug penetration in tumors. Cancer Res. 64, 3731-3736 (2004).
30. Zhou, K. et al. Apatinib, a selective VEGFR2 inhibitor, improves the delivery of chemotherapeutic agents to tumors by normalizing tumor vessels in LoVo colon cancer xenograft mice. Acta Pharmacol. Sin. doi.org/10.1038/s41401-018-0058-y (2018).
31. Pazos, M. C. et al. PDGFB as a vascular normalization agent in an ovarian cancer model treated with a gamma-secretase inhibitor. J. Cell. Physiol. 233, 5949-5961 (2018).
32. Chen, Q. et al. Tumor vasculature normalization by orally fed erlotinib to modulate the tumor microenvironment for enhanced cancer nanomedicine and immunotherapy. Biomaterials 148, 69-80 (2017).
33. Kim, S. J. et al. Tumor vessel normalization by the PI3K inhibitor HS-173 enhances drug delivery. Cancer Lett. 403, 339-353 (2017).
34. Ganss, R. Tumour vessel normalization and immune checkpoint blockade: a new synergism. Immunol. Cell Biol. 95, 497-498 (2017).
35. De Palma, M. & Jain, R. K. CD4(+) T cell activation and vascular normalization: two sides of the same coin? Immunity 46, 773-775 (2017).
36. Tian, L. et al. Mutual regulation of tumour vessel normalization and immunostimulatory reprogramming. Nature 544, 250-254 (2017).
37. Kiuchi, N. et al. STAT3 is required for the gp130-mediated full activation of the c-myc gene. J. Exp. Med. 189, 63-73 (1999).
38. Niu, G. et al. Constitutive Stat3 activity up-regulates VEGF expression and tumor angiogenesis. Oncogene 21, 2000-2008 (2002).
39. Yu, H., Kortylewski, M. & Pardoll, D. Crosstalk between cancer and immune cells: role of STAT3 in the tumour microenvironment. Nat. Rev. Immunol. 7, 41-51 (2007).
40. Roush, S. & Slack, F. J. The let-7 family of microRNAs. Trends Cell Biol. 18, 505-516 (2008).
41. Iliopoulos, D. et al. An epigenetic switch involving NF-kappaB, Lin28, Let-7 MicroRNA, and IL6 links inflammation to cell transformation. Cell 139, 693-706 (2009).
42. Baer, C. et al. Suppression of microRNA activity amplifies IFN-γ-induced macrophage activation and promotes anti-tumour immunity. Nat. Cell Biol. 18, 790-802 (2016).
43. Anand, S. et al. MicroRNA-132-mediated loss of p120RasGAP activates the endothelium to facilitate pathological angiogenesis. Nat. Med. 16, 909-914 (2010).
44. Pello, O. M. et al. Role of c-MYC in alternative activation of human macrophages and tumor-associated macrophage biology. Blood 119, 411-421 (2012).
45. Sampson, V. B. et al. MicroRNA let-7a down-regulates MYC and reverts MYC-induced growth in Burkitt lymphoma cells. Cancer Res. 67, 9762-9770 (2007).
46. Sears, R. C. The life cycle of C-myc: from synthesis to degradation. Cell Cycle 3, 1133-1137 (2004).
47. Faridi, M. H. et al. High-throughput screening based identification of small molecule antagonists of integrin CD11b/CD18 ligand binding. Biochem. Biophys. Res. Commun. 394, 194-199 (2010).
48. Maiguel, D. et al. Small molecule-mediated activatin of the integrin CD11b/CD18 reduced inflammatory disease. Sci. Signal. 4, a57 (2011).
49. Faridi, M. H. et al. CD11b activation suppresses TLR-dependent inflammation and autoimmunity in systemic lupus erythematosus. J. Clin. Invest. 127, 1271-1283 (2017).

Although the invention has been described with reference to the above description, it will be understood that modifications and variations are encompassed within the spirit and scope of the invention. Accordingly, the invention is limited only by the following claims.

What is claimed is:

1. A method of identifying a cancer amenable to treatment with an agonist of CD11b or a Let7a miRNA comprising detecting expression levels of CD11b or Let7a miRNA in a sample comprising cancer associated myeloid cells from a subject, contacting the sample with an agonist of CD11b or a Let7a miRNA and detecting increased levels of CD11b or a Let7a miRNA, thereby identifying the cancer as being amenable to treatment with the agonist of CD11b or a Let7a miRNA.

2. The method of claim 1, further comprising detecting an increase in expression of one or more of Arg1, Tgfb, Il10, Il6 or Pdgfb after contacting with the inhibitor, as compared to expression prior to contacting.

3. The method of claim 1, further comprising detecting a decrease in expression of one or more of Il12, Ifng, Nos2, or Tnfa after contacting with the inhibitor, as compared to expression prior to contacting.

4. A method of increasing susceptibility of a cancer cell of a subject to chemotherapeutic treatment comprising contacting cancer associated myeloid cells obtained from the subject with Let7a miRNA or leukadherin 1 (LA1), thereby increasing susceptibility of the cancer cell to chemotherapeutic treatment.

5. The method of claim 4, wherein the chemotherapeutic treatment is administration of an agent selected from the group consisting of gemcitabine, pembrolizumab, nivolumab, cemiplimab, atezolizumab, avelumab, durvalumab, and ipilimumab.

6. A method of screening for a therapeutic agent for treating cancer, comprising administering a test agent to a transgenic non-human mammal whose genome comprises a mutation at Ile332 of exon 9 of the ITGAM gene, wherein the transgenic non-human mammal has the phenotype of loss of an Exon-9 Bgl II restriction site, and evaluating the effect of the test agent on at least one of expression levels of CD11b or Let7a in at least one disease-relevant tissue of the transgenic non-human mammal, wherein at least one of: an increase in the amount of CD11b expression, an increase in the amount of Let7a expression, or increase in the amount of CD11b expression and an increase in the amount of Let7a expression in at least one disease-relevant tissue relative to a similar transgenic non-human mammal that does not receive the test agent indicates the test agent is therapeutic for the cancer.

7. The method of claim 6, further comprising detecting increases in expression of one or more of Il1b, Tnfa, Il12, Nos2 and Ifng in at least one disease-relevant tissue relative to a similar transgenic non-human mammal that does not receive the test agent, thereby confirming that the test agent is therapeutic for the cancer.

8. The method of claim 6, wherein the Ile332 is substituted with Gly.

9. The method of claim 6, wherein the mammal is a mouse.

* * * * *

UNITED STATES PATENT AND TRADEMARK OFFICE
CERTIFICATE OF CORRECTION

| | |
|---|---|
| PATENT NO. | : 11,679,100 B2 |
| APPLICATION NO. | : 17/058605 |
| DATED | : June 20, 2023 |
| INVENTOR(S) | : Judith Varner and Michael C. Schmid |

It is certified that error appears in the above-identified patent and that said Letters Patent is hereby corrected as shown below:

In the Specification

At Column 1, Line 15, after "under" insert --DE027325,--

At Column 1, Line 16, after "CA167426" insert --, and CA226909--

In the Claims

Column 41, Line 67, In Claim 2, "1110" should be replaced with "I110"

Column 42, Line 55, In Claim 2, "116" should be replaced with "I16"

Signed and Sealed this
Twelfth Day of September, 2023

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 1153
<212> TYPE: PRT
<213> ORGANISM: Mus musculus

```
<400> SEQUENCE: 1

Met Thr Leu Lys Ala Leu Leu Val Thr Ala Leu Ala Leu Cys His Gly
1               5                   10                  15

Phe Asn Leu Asp Thr Glu His Pro Met Thr Phe Gln Glu Asn Ala Lys
            20                  25                  30

Gly Phe Gly Gln Asn Val Val Gln Leu Gly Gly Thr Ser Val Val Val
        35                  40                  45

Ala Ala Pro Gln Glu Ala Lys Ala Val Asn Gln Thr Gly Ala Leu Tyr
    50                  55                  60

Gln Cys Asp Tyr Ser Thr Ser Arg Cys His Pro Ile Pro Leu Gln Val
65              70                  75                  80

Pro Pro Glu Ala Val Asn Met Ser Leu Gly Leu Ser Leu Ala Val Ser
                85                  90                  95

Thr Val Pro Gln Gln Leu Leu Ala Cys Gly Pro Thr Val His Gln Asn
            100                 105                 110

Cys Lys Glu Asn Thr Tyr Val Asn Gly Leu Cys Tyr Leu Phe Gly Ser
        115                 120                 125

Asn Leu Leu Arg Pro Pro Gln Gln Phe Pro Glu Ala Leu Arg Glu Cys
    130                 135                 140

Pro Gln Gln Glu Ser Asp Ile Val Phe Leu Ile Asp Gly Ser Gly Ser
145                 150                 155                 160

Ile Asn Asn Ile Asp Phe Gln Lys Met Lys Glu Phe Val Ser Thr Val
                165                 170                 175

Met Glu Gln Phe Lys Lys Ser Lys Thr Leu Phe Ser Leu Met Gln Tyr
            180                 185                 190

Ser Asp Glu Phe Arg Ile His Phe Thr Phe Asn Asp Phe Lys Arg Asn
        195                 200                 205

Pro Ser Pro Arg Ser His Val Ser Pro Ile Lys Gln Leu Asn Gly Arg
    210                 215                 220

Thr Lys Thr Ala Ser Gly Ile Arg Lys Val Val Arg Glu Leu Phe His
225                 230                 235                 240

Lys Thr Asn Gly Ala Arg Glu Asn Ala Ala Lys Ile Leu Val Val Ile
                245                 250                 255

Thr Asp Gly Glu Lys Phe Gly Asp Pro Leu Asp Tyr Lys Asp Val Ile
            260                 265                 270

Pro Glu Ala Asp Arg Ala Gly Val Ile Arg Tyr Val Ile Gly Val Gly
        275                 280                 285

Asn Ala Phe Asn Lys Pro Gln Ser Arg Arg Glu Leu Asp Thr Ile Ala
    290                 295                 300

Ser Lys Pro Ala Gly Glu His Val Phe Gln Val Asp Asn Phe Glu Ala
305                 310                 315                 320

Leu Asn Thr Ile Gln Asn Gln Leu Gln Glu Lys Ile Phe Ala Ile Glu
                325                 330                 335

Gly Thr Gln Thr Gly Ser Thr Ser Ser Phe Glu His Glu Met Ser Gln
            340                 345                 350

Glu Gly Phe Ser Ala Ser Ile Thr Ser Asn Gly Pro Leu Leu Gly Ser
        355                 360                 365

Val Gly Ser Phe Asp Trp Ala Gly Gly Ala Phe Leu Tyr Thr Ser Lys
    370                 375                 380

Asp Lys Val Thr Phe Ile Asn Thr Thr Arg Val Asp Ser Asp Met Asn
385                 390                 395                 400

Asp Ala Tyr Leu Gly Tyr Ala Ser Ala Val Ile Leu Arg Asn Arg Val
                405                 410                 415
```

-continued

Gln Ser Leu Val Leu Gly Ala Pro Arg Tyr Gln His Ile Gly Leu Val
            420                 425                 430

Val Met Phe Arg Glu Asn Phe Gly Thr Trp Glu Pro His Thr Ser Ile
        435                 440                 445

Lys Gly Ser Gln Ile Gly Ser Tyr Phe Gly Ala Ser Leu Cys Ser Val
        450                 455                 460

Asp Met Asp Ala Asp Gly Asn Thr Asn Leu Ile Leu Ile Gly Ala Pro
465                 470                 475                 480

His Tyr Tyr Glu Lys Thr Arg Gly Gly Gln Val Ser Val Cys Pro Leu
                485                 490                 495

Pro Arg Gly Arg Ala Arg Trp Gln Cys Glu Ala Leu Leu His Gly Asp
            500                 505                 510

Gln Gly His Pro Trp Gly Arg Phe Gly Ala Ala Leu Thr Val Leu Gly
        515                 520                 525

Asp Val Asn Gly Asp Lys Leu Thr Asp Val Ala Ile Gly Ala Pro Gly
        530                 535                 540

Glu Gln Glu Asn Gln Gly Ala Val Tyr Ile Phe Tyr Gly Ala Ser Ile
545                 550                 555                 560

Ala Ser Leu Ser Ala Ser His Ser His Arg Ile Ile Gly Ala His Phe
                565                 570                 575

Ser Pro Gly Leu Gln Tyr Phe Gly Gln Ser Leu Ser Gly Gly Lys Asp
            580                 585                 590

Leu Thr Met Asp Gly Leu Met Asp Leu Ala Val Gly Ala Gln Gly His
        595                 600                 605

Leu Leu Leu Leu Arg Ala Gln Pro Val Leu Arg Leu Glu Ala Thr Met
        610                 615                 620

Glu Phe Ser Pro Lys Lys Val Ala Arg Ser Val Phe Ala Cys Gln Glu
625                 630                 635                 640

Gln Val Leu Lys Asn Lys Asp Ala Gly Glu Val Arg Val Cys Leu Arg
                645                 650                 655

Val Arg Lys Asn Thr Lys Asp Arg Leu Arg Glu Gly Asp Ile Gln Ser
            660                 665                 670

Thr Val Thr Tyr Asp Leu Ala Leu Asp Pro Val Arg Ser Arg Ile Arg
        675                 680                 685

Ala Phe Phe Asp Glu Thr Lys Asn Asn Thr Arg Arg Thr Gln Val
        690                 695                 700

Phe Gly Leu Met Gln Lys Cys Glu Thr Leu Lys Leu Ile Leu Pro Asp
705                 710                 715                 720

Cys Val Asp Asp Ser Val Ser Pro Ile Ile Leu Arg Leu Asn Tyr Thr
                725                 730                 735

Leu Val Gly Glu Pro Leu Arg Ser Phe Gly Asn Leu Arg Pro Val Leu
            740                 745                 750

Ala Met Asp Ala Gln Arg Phe Phe Thr Ala Met Phe Pro Phe Glu Lys
        755                 760                 765

Asn Cys Gly Asn Asp Ser Ile Cys Gln Asp Asp Leu Ser Ile Thr Met
        770                 775                 780

Ser Ala Met Gly Leu Asp Thr Leu Val Val Gly Gly Pro Gln Asp Phe
785                 790                 795                 800

Asn Met Ser Val Thr Leu Arg Asn Asp Gly Glu Asp Ser Tyr Gly Thr
                805                 810                 815

Gln Val Thr Val Tyr Tyr Pro Ser Gly Leu Ser Tyr Arg Lys Asp Ser
            820                 825                 830

```
Ala Ser Gln Asn Pro Leu Thr Lys Lys Pro Trp Phe Val Lys Pro Ala
            835                 840                 845

Glu Ser Ser Ser Ser Glu Gly His Gly Ala Leu Lys Ser Thr Thr
850                 855                 860

Trp Asn Ile Asn His Pro Ile Phe Pro Ala Asn Ser Glu Val Thr Phe
865             870                 875                 880

Asn Val Thr Phe Asp Val Asp Ser His Ala Ser Phe Gly Asn Lys Leu
                885                 890                 895

Leu Leu Lys Ala Ile Val Ala Ser Glu Asn Asn Met Ser Arg Thr His
            900                 905                 910

Lys Thr Lys Phe Gln Leu Glu Leu Pro Val Lys Tyr Ala Ile Tyr Met
            915                 920                 925

Ile Val Thr Ser Asp Glu Ser Ser Ile Arg Tyr Leu Asn Phe Thr Ala
            930                 935                 940

Ser Glu Met Thr Ser Lys Val Ile Gln His Gln Tyr Gln Phe Asn Asn
945                 950                 955                 960

Leu Gly Gln Arg Ser Leu Pro Val Ser Val Val Phe Trp Ile Pro Val
                965                 970                 975

Gln Ile Asn Asn Val Thr Val Trp Asp His Pro Gln Val Ile Phe Ser
                980                 985                 990

Gln Asn Leu Ser Ser Ala Cys His Thr Glu Gln Lys Ser Pro Pro His
            995                 1000                1005

Ser Asn Phe Arg Asp Gln Leu Glu Arg Thr Pro Val Leu Asn Cys
    1010                1015                1020

Ser Val Ala Val Cys Lys Arg Ile Gln Cys Asp Leu Pro Ser Phe
    1025                1030                1035

Asn Thr Gln Glu Ile Phe Asn Val Thr Leu Lys Gly Asn Leu Ser
    1040                1045                1050

Phe Asp Trp Tyr Ile Lys Thr Ser His Gly His Leu Leu Leu Val
    1055                1060                1065

Ser Ser Thr Glu Ile Leu Phe Asn Asp Ser Ala Phe Ala Leu Leu
    1070                1075                1080

Pro Gly Gln Glu Ser Tyr Val Arg Ser Lys Thr Glu Thr Lys Val
    1085                1090                1095

Glu Pro Tyr Glu Val His Asn Pro Val Pro Leu Ile Val Gly Ser
    1100                1105                1110

Ser Ile Gly Gly Leu Val Leu Leu Ala Leu Ile Thr Ala Gly Leu
    1115                1120                1125

Tyr Lys Leu Gly Phe Phe Lys Arg Gln Tyr Lys Asp Met Met Asn
    1130                1135                1140

Glu Ala Ala Pro Gln Asp Ala Pro Pro Gln
    1145                1150
```